US012590070B2

(12) United States Patent
Ki et al.

(10) Patent No.: US 12,590,070 B2
(45) Date of Patent: Mar. 31, 2026

(54) ADAMANTANE DERIVATIVES AS INHIBITORS OF FOCAL ADHESION KINASE

(71) Applicants: SAMJIN PHARMACEUTICAL CO., LTD., Seoul (KR); INCHEON NATIONAL UNIVERSITY RESEARCH & BUSINESS FOUNDATION, Yeonsu-gu (KR); BAMICHEM CO., LTD., Yeonsu-gu (KR)

(72) Inventors: Min Hyo Ki, Seongnam-si (KR); Ho Seok Kwon, Suwon-si (KR); Young Hun Lee, Seoul (KR); Eunsun Song, Seongnam-si (KR); Yong Bin Park, Anyang-si (KR); Kug Hwa Lee, Yongin-si (KR); Hyoung Min Cho, Seongnam-si (KR); Soon Kil Ahn, Seoul (KR); Sung Pyo Hong, Yeonsu-gu (KR); Sung Hye Kim, Yeonsu-gu (KR)

(73) Assignees: SAMJIN PHARMACEUTICAL CO., LTD., Seoul (KR); INCHEON NATIONAL UNIVERSITY RESEARCH & BUSINESS FOUNDATION, Incheon (KR); BAMICHEM CO., LTD., Incheon (KR)

( * ) Notice: Subject to any disclaimer, the term of this patent is extended or adjusted under 35 U.S.C. 154(b) by 891 days.

(21) Appl. No.: 17/782,117

(22) PCT Filed: Dec. 2, 2020

(86) PCT No.: PCT/IB2020/061350
§ 371 (c)(1),
(2) Date: Jun. 2, 2022

(87) PCT Pub. No.: WO2021/111311
PCT Pub. Date: Jun. 10, 2021

(65) Prior Publication Data

US 2023/0049557 A1 Feb. 16, 2023

(30) Foreign Application Priority Data

Dec. 3, 2019 (KR) ........................ 10-2019-0159011

(51) Int. Cl.
*C07D 239/48* (2006.01)
*A61P 35/00* (2006.01)
*C07D 401/12* (2006.01)

(52) U.S. Cl.
CPC ............ *C07D 239/48* (2013.01); *A61P 35/00* (2018.01); *C07D 401/12* (2013.01)

(58) Field of Classification Search
CPC ...... C07D 239/48; C07D 401/12; A61P 35/00
See application file for complete search history.

(56) References Cited

U.S. PATENT DOCUMENTS

| | | | |
|---|---|---|---|
| 2019/0276426 A1 | 9/2019 | Gray et al. | |
| 2019/0300533 A1 | 10/2019 | Wang et al. | |

FOREIGN PATENT DOCUMENTS

| | | | | | |
|---|---|---|---|---|---|
| CN | 1788001 | A | | 6/2006 | |
| CN | 101921236 | A | | 12/2010 | |
| CN | 103641833 | A | | 3/2014 | |
| CN | 106905303 | | | 6/2017 | |
| EP | 3392245 | | | 10/2018 | |
| JP | 2003519130 | A | | 6/2003 | |
| JP | 2005501860 | A | | 1/2005 | |
| JP | 2007502260 | A | | 2/2007 | |
| JP | 2009525337 | A | | 7/2009 | |
| KR | 10-2020-0046952 | A | | 5/2020 | |
| WO | 01/47897 | | | 7/2001 | |
| WO | 03/018022 | | | 3/2003 | |
| WO | 03/026666 | | | 4/2003 | |
| WO | 2004080980 | A1 | | 9/2004 | |
| WO | 2005/016894 | | | 2/2005 | |
| WO | 2007089768 | A2 | | 8/2007 | |
| WO | 2008073687 | A2 | | 6/2008 | |
| WO | 2012120051 | A1 | | 9/2012 | |
| WO | WO-2013170147 | A1 | * | 11/2013 | ........... A61K 47/545 |
| WO | 2018215795 | A2 | | 11/2018 | |
| WO | 2020085742 | A1 | | 4/2020 | |
| WO | WO-2020069117 | A1 | * | 4/2020 | ............ A61K 47/55 |

OTHER PUBLICATIONS

Blackadar, World Journal of Clinical Oncology, Feb. 10, 2016; 7(1): 54-86 (Year: 2016).*
Hassanpour, Journal of Cancer Research and Practice, 4, 2017, 127-129 (Year: 2017).*
The American Cancer Society, cancer.org, Can Acute Lymphocytic Leukemia Be Prevented?, https://web.archive.org/web/20241209175137/https://www.cancer.org/cancer/types/acute-lymphocytic-leukemia/causes-risks-prevention/prevention.html, Last updated Oct. 17, 2018 (Year: 2018).*
The American Cancer Society, cancer.org, Can Hodgkin Lymphoma be Prevented?, https://web.archive.org/web/20231211145704/https://www.cancer.org/cancer/types/hodgkin-lymphoma/causes-risks-prevention/prevention.html, Last updated May 1, 2018 (Year: 2018).*
Hu, Frontiers in Pharmacology, Feb. 12, 2024, 15:1274209 (Year: 2024).*
Chinese Office Action and Search Report issued in CN Application No. 2020800827643 dated May 29, 2023, 17 pages.
Chen Ying, et al., "Research and Development of Focal-Adhesion Kinase(FAK) and the Inhibitors", Chin J Mod Appl Pharm, Feb. 2016, vol. 33 No. 2, 6 pages.

(Continued)

*Primary Examiner* — Andrew D Kosar
*Assistant Examiner* — Phillip Matthew Rzeczycki
(74) *Attorney, Agent, or Firm* — NIXON & VANDERHYE, PC

(57) ABSTRACT

The present invention provides novel adamantane derivatives as inhibitors of a focal adhesion kinase, pharmaceutically acceptable salts thereof, stereoisomers thereof, hydrates or solvates thereof, and a pharmaceutical composition comprising same.

17 Claims, 2 Drawing Sheets

(56) References Cited

OTHER PUBLICATIONS

Toshio Shimizu, et al., "A first in Asian phase 1 study to evaluate safety, pharmacokinetics and clinical activity of VS 6063, a focal adhesion kinase (FAK) inhibitor in Japanese patients with advanced solid tumors", Cancer Chemother Pharmacol, 2016, 77, 7 pages.
Extended European Search Report in related EP Application No. 20895884.3 dated Dec. 5, 2023, 7 pages.
Japanese Office Action and Search Report issued in JP Application No. 2022-532125 dated Jul. 12, 2023, 6 pages.
Korean Notice of Allowance dated Nov. 14, 2022 for Korean Application No. 10-2020-0166369 with English machine translation (6 pages).
Jyotsnabaran Halder, et al., "Therapeutic Efficacy of a Novel Focal Adhesion Kinase Inhibitor TAE226 in Ovarian Carcinoma", Cancer Res., vol. 67, No. 22, Nov. 15, 2007, pp. 10976-10983 (8 pages).
Alexander Schultze, et al., "Therapeutic potential and limitations of new FAK inhibitors in the treatment of cancer", Expert Opinion on Investigational Drugs, vol. 19, No. 6, published online May 13, 2010, pp. 777-788 (13 pages).
International Search Report for PCT/IB2020/061350 dated Mar. 17, 2021, 13 pages.
Written Opinion of the ISA for PCT/IB2020/061350 dated Mar. 17, 2021, 4 pages.

* cited by examiner

ADAMANTANE DERIVATIVES AS INHIBITORS OF FOCAL ADHESION KINASE

CROSS-REFERENCE TO RELATED APPLICATIONS

This application is the U.S. national phase of International Application No. PCT/IB2020/061350 filed Dec. 2, 2020 which designated the U.S. and claims priority to KR Patent Application No. 10-2019-0159011 filed Dec. 3, 2019, the entire contents of each of which are hereby incorporated by reference.

TECHNICAL FIELD

The present invention relates to novel adamantane derivatives as inhibitors of a focal adhesion kinase, pharmaceutically acceptable salts thereof, stereoisomers thereof, hydrates or solvates thereof, and a pharmaceutical composition including the same.

BACKGROUND ART

Cancer is known as the most dreaded incurable disease, for which an appropriate treatment method has not been yet developed in modern medicine despite an increasing incidence of cancer as a disease with high mortality worldwide. Currently developed anticancer drugs are mainly related to the mechanism of inhibiting cell growth or inducing apoptosis, but have side effects such as cytotoxicity, etc., by affecting not only cancer cells but also normal cells. With the recent development of medical biology and molecular biological technology, unique properties of cancer cells have been revealed, and many new molecular-level targets involved in these properties have been discovered through a genome sequence analysis, thus resulting in the development of anticancer drugs with such targets.

In general, signal transduction systems present in cells are organically linked to each other to form a complex mechanism, thereby regulating cell proliferation, growth, metastasis, and death. In the signal transduction systems, a protein tyrosine kinase plays an important role in intracellular regulatory functions. Many diseases are associated with abnormal cellular responses triggered by the protein tyrosine kinase.

These diseases include autoimmune disease, inflammatory disease, bone disease, metabolic disease, neurological and neurodegenerative disease, cancer, cardiovascular disease, allergy and asthma, Alzheimer's disease, viral disease and hormone-associated disease. In particular, the abnormal expression and mutation of the protein tyrosine kinase are often observed in cancer cells, and thus many studies are being conducted in medicinal chemistry to develop an effective protein tyrosine kinase inhibitor as anticancer therapeutics.

Focal adhesion kinase (FAK), which is a protein encoded by PTK2 gene and a non-receptor tyrosine kinase present in the cytoplasm, is known to receive signals from integrin and growth factor receptors and play an important role in the regulation of cell growth, proliferation, adhesion, migration, invasion and self-reproduction of cancer stem cells. The FAK is regulated and activated through autophosphorylation of Y397 and binds to autophosphorylated Y397 through an SH2 domain of Src protein, which is another tyrosine kinase, and the Src protein phosphorylates Y925 of the FAK, thus attracting adapter protein Grb2 and inducing the activation of ras and MAP kinase pathways involved in regulating cell proliferation.

In normal cells, signal transduction via the FAK is very tightly regulated, but in cells transformed into tumors, the FAK is overexpressed and activated, thus causing various properties of malignant tumors. It is known that the overexpression of the FAK plays a pivotal role in an oncogenic process (tumor formation, invasion, metastasis, etc.) by promoting tumor cell proliferation, invasion and metastasis, inhibiting cancer cell death, and increasing angiogenesis. As a result of the study confirming the association of the FAK in such process, it was observed that normal cell adhesion is inhibited in tumor cells in which an FAK activity is inhibited with FAK antisense oligonucleotides, thus undergoing an apoptosis process. In fibroblasts deficient in FAK expression, it was reported that a cell shape is changed from a spindle shape to a circular shape compared to normal cells and cell migration is inhibited in response to a chemotactic signal, and it was also confirmed that such phenomenon is returned to an original state through the reexpression of the FAK.

It was confirmed that FAK protein and mRNA are overexpressed in various solid cancers such as breast cancer, colorectal cancer, lung cancer, ovarian cancer, prostate cancer, etc., as well as blood cancers such as acute myeloid leukemia, and phosphorylated FAK showing activity is increased in malignant tissues than in normal tissues. In particular, the higher the FAK activity, the poorer the prognosis in cancer patients. Accordingly, it is considered that the activity of the FAK is importantly involved in the progression or metastasis of human cancer.

In addition, proline-rich tyrosine kinase 2 (PYK2), the only subtype of the FAK, is most widely distributed in neurons, and has been recently confirmed to have a value as a molecular target for the development of anticancer drugs for small cell lung cancer, prostate cancer, hepatocellular carcinoma, glioma, etc.

As such, anti-cancer effects through inhibition of FAK activity are expected, and thus about 20 types of low-molecular compounds that inhibit the FAK activity are being developed worldwide. Among them, TAE226 has showed excellent efficacy in reducing a tumor size by 87 to 90% through a single administration or a combined administration with docetaxel in three types of breast cancer animal models formed with a taxane-sensitive cell line (HeyA8, SKOV3ip) and a taxane-resistant cell line (HeyA8-MDR), but has been found to inhibit an insuline receptor and cause serious side effects such as unexpected inhibition of glucose metabolism, a decrease in blood concentration and the like, thus failing in a preclinical study. Instead, PF-04554878 and GSK2256098 are in clinical phase studies.

Related Art References (Non-Patent Document 1) Cancer Res. 2007, 67: 10976-10983

(Non-Patent Document 2) Expert Opin. Investing. Drugs, 2010, 19: 777-788

DETAILED DESCRIPTION OF THE INVENTION

Technical Problem

In order to solve the above problems, one object of the present invention is to provide novel adamantane derivatives as inhibitors of a focal adhesion kinase, pharmaceutically acceptable salts thereof, stereoisomers thereof, hydrates or solvates thereof.

Another object of the present invention is to provide a pharmaceutical composition including the novel adamantane derivatives as inhibitors of a focal adhesion kinase, pharmaceutically acceptable salts thereof, stereoisomers thereof, hydrates or solvates thereof as active ingredients.

Another object of the present invention is to provide a pharmaceutical composition for preventing or treating FAK-associated diseases, including the novel adamantane derivatives as inhibitors of a focal adhesion kinase, pharmaceutically acceptable salts thereof, stereoisomers thereof, hydrates or solvates thereof as active ingredients.

Another object of the present invention is to provide a method for preventing or treating FAK activity-associated diseases, including administering a therapeutically effective amount of the novel adamantane derivatives as inhibitors of a focal adhesion kinase, pharmaceutically acceptable salts thereof, stereoisomers thereof, hydrates or solvates thereof into an individual.

Another object of the present invention is to provide a use of the novel adamantane derivatives as inhibitors of a focal adhesion kinase, pharmaceutically acceptable salts thereof, stereoisomers thereof, hydrates or solvates thereof for preventing or treating FAK activity-associated diseases.

Another object of the present invention is to provide a use of the novel adamantane derivatives as inhibitors of a focal adhesion kinase, pharmaceutically acceptable salts thereof, stereoisomers thereof, hydrates or solvates thereof for manufacture of a medicament for preventing or treating FAK activity-associated diseases.

Technical Solution

According to the present invention, novel adamantane derivatives as inhibitors of a focal adhesion kinase, pharmaceutically acceptable salts thereof, stereoisomers thereof, hydrates or solvates thereof are represented by formula 1 below:

[Formula 1]

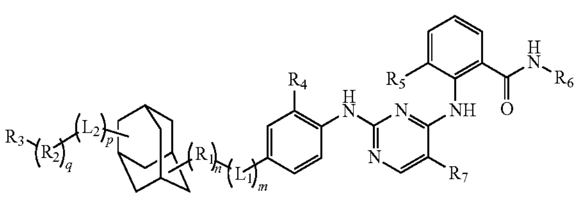

wherein in above formula 1, $L_1$ and $L_2$ are each independently a single bond, $C_{1-10}$ alkylene, $C_{2-10}$ alkenylene, $C_{2-10}$ alkynylene, —N(Ra)—, —C(=O)—N(Ra)—, —N(Ra)—C(=O)—, —C(=O)—, —O—, —C(=O)—O—, —N(Ra)—C(=O)—O—, —N(Ra)—S(=O)—, —N(Ra)—S(=O)$_2$—, —S(=O)(=N—Ra)—, or —S—;

$R_1$ and $R_2$ are each independently $C_{1-10}$ heterocycloalkylene, $C_{3-10}$ cycloalkylene, $C_{5-16}$ arylene or $C_{4-10}$ heteroarylene;

$R_3$ is H, $C_{1-10}$ alkyl, $C_{2-10}$ alkenyl, —O—Ra, =O, —NH—Ra, —NH(C=O)—Ra or $C_{1-10}$ heterocycloalkyl;

$R_4$ is —O—Ra;

$R_5$ and $R_6$ are each independently H or $C_{1-10}$ alkyl;

$R_7$ is —$CF_3$ or a halogen atom;

Ra is H, —$CF_3$ or $C_{1-10}$ alkyl; and m, n, p and q are each independently 0 or 1.

In one embodiment, $R_1$ and $R_2$ of above formula 1 may be each independently

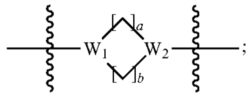

;

$R_3$ may be H, $C_{1-10}$ alkyl, $C_{2-10}$ alkenyl, —O—Ra, =O, —NH—Ra, —NH(C=O)—Ra or

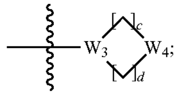

;

$W_1$, $W_2$ and $W_3$ may be each independently CH or N;

$W_4$ may be $CH_2$, NH or O;

Ra may be H, —$CF_3$ or $C_{1-10}$ alkyl; and a, b, c and d may be each independently 1, 2 or 3.

In one embodiment, $R_1$ and $R_2$ of above formula 1 may be each independently

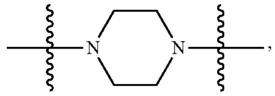

,

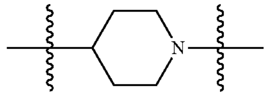

or

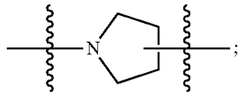

;

$R_3$ may be H, $C_{1-10}$ alkyl, $C_{2-10}$ alkenyl, —O—Ra, =O, —NH—Ra, —NH(C=O)—Ra or

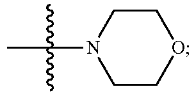 [SMILES: *N1CCOCC1]

;

and

Ra may be H, —$CF_3$ or $C_{1-10}$ alkyl.

In one embodiment, a compound represented by above formula 1 may be a compound represented by formula 2 below:

[Formula 2]

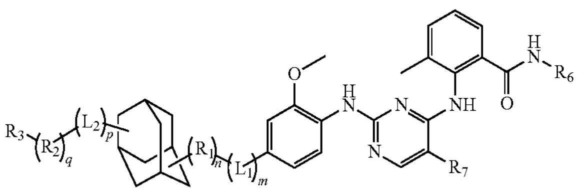

wherein in above formula 2, $L_1$ is —N(Ra)—, —C(═O)—N(Ra)— or —O—;

$L_2$ is —N(Ra)—, —C(═O)—N(Ra)—, —N(Ra)—C(═O)—, —C(═O)— or —C(═O)—O—;

$R_1$ and $R_2$ are each independently

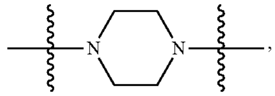
,
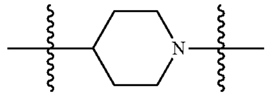
or
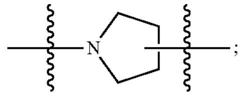
;

$R_3$ is H, $C_{1-10}$ alkyl, $C_{2-10}$ alkenyl, —O—Ra, ═O, —NH—Ra, —NH(C═O)—Ra or morpholinyl;

$R_6$ is H or $C_{1-10}$ alkyl;

$R_7$ is —$CF_3$ or Cl;

Ra is H, —$CF_3$ or $C_{1-10}$ alkyl; and m, n, p and q are each independently 0 or 1.

Advantageous Effects

Novel adamantane derivatives of the present invention as inhibitors of a focal adhesion kinase, pharmaceutically acceptable salts thereof, stereoisomers thereof, hydrates or solvates thereof can exhibit an action effect without inhibiting the activity of an insulin receptor (Ins-R) while selectively inhibiting the activity of FAK and Pyk2 (FAK2) at the same time.

Adamantane derivatives, pharmaceutically acceptable salts thereof, stereoisomers thereof, hydrates or solvates thereof according to the present invention can inhibit the abnormal activity of the FAK. By inhibiting the abnormal activity of the FAK, they can be advantageously used for the prevention and treatment of induced abnormal cell growth diseases.

MODE FOR INVENTION

Figure 1:
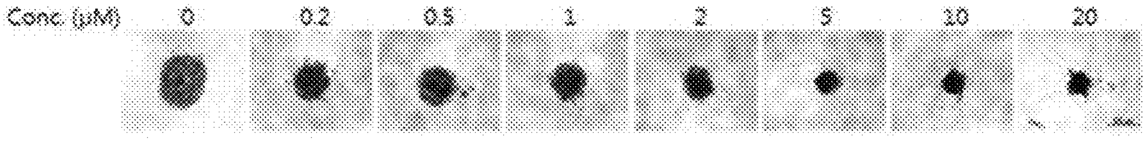
FIG. 1 shows the results of a 3D spheroid assay for analyzing a degree of growth inhibition of cancer cell spheroids by the adamantane derivative compound of the present invention.

Hereinafter, terms used in the present application are used only to describe a certain exemplary embodiment and are not intended to limit the present invention. The terms of a singular form may include plural forms unless otherwise specified. In the present application, terms such as "include," "have" or the like shall be intended to designate a presence of features, steps, operations, components, parts or combinations thereof described herein, and shall not be construed to exclude a possible presence or addition of one or more other features, steps, operations, components, parts or combinations thereof in advance.

All the terms used herein including technical or scientific terms have the same meaning as commonly understood by those ordinary skilled in the art, to which the present invention pertains, unless defined otherwise. Such terms as those defined in a generally used dictionary are to be interpreted to have the meanings equal to the contextual meanings in the relevant art, and are not to be interpreted to have ideal or excessively formal meanings, unless clearly defined in the present application.

Adamantane Derivatives, Pharmaceutically Acceptable Salts Thereof, Stereoisomers Thereof, Hydrates or Solvates Thereof In the present invention, in the expression "Cx" of a functional group, x may represent the number of carbons (C), and Cx-y may mean a functional group having x or more and y or less carbons.

In the present invention, the term "substituted" may represent a moiety having a substituent which replaces at least one hydrogen on carbon of a main chain. The "substitution" or "substituted with-" may be defined to include implicit conditions, in which the substitution follows a permitted valency of a substituted atom and a substituent and induces a compound stabilized by substitution, for example, a compound which is not naturally modified by rearrangement, cyclization, removal, etc.

In the present invention, "single bond" may mean a case in which atoms or groups of atoms adjacent to $L_1$ or $L_2$ are directly bonded to each other.

In the present invention, "alkyl" may mean a linear (or straight-chain) saturated hydrocarbon group or a branched (or side-chain) saturated hydrocarbon group, and may include methyl, ethyl, n-propyl, isopropyl, n-butyl, sec-butyl, isobutyl, tert-butyl, n-pentyl, n-hexyl, n-heptyl, etc., but is not limited thereto.

In the present invention, "alkylene" may mean a divalent functional group which is induced from alkyl as defined above.

In the present invention, "alkenyl" may mean an unsaturated hydrocarbon group including at least one double bond between carbons, and "alkynyl" may mean an unsaturated hydrocarbon group including at least one triple bond between carbons.

In the present invention, "alkenylene" may mean a divalent functional group derived from alkenyl as defined above, and "alkynylene" may mean a divalent functional group derived from alkynyl as defined above.

In the present invention, "halogen atom" may mean F, Cl, Br or I.

In the present invention, "aryl" may include a monocyclic aromatic structure or a polycyclic aromatic structure, as well as a structure in which a saturated hydrocarbon ring is fused into the monocyclic aromatic or polycyclic aromatic structure. Aryl may include a phenyl group, biphenyl, naphthalenyl, tetrahydronaphthalenyl, anthracenyl, phenanthrenyl, pyrenyl, etc., but is not limited thereto.

In the present invention, "heteroaryl" may mean a monocyclic or polycyclic hetero ring in which at least one or more carbon atoms are substituted with nitrogen (N), oxygen (O) or sulfur (S) in the aryl group. Heteroaryl may include pyridinyl, thiophenyl, triazolyl, tetrazolyl, benzodioxolyl, benzothiazolyl, benzothiophenyl, quinolinyl, indolyl, isoindolyl, benzofuranyl, benzopyrrolyl, furanyl, pyrrolyl, thiazolyl, isothiazolyl, imidazolyl, pyrazolyl, oxazolyl, isoxazolyl, pyrazinyl, pyridazinyl, pyrimidinyl, isoquinolinyl, carbazolyl, benzoxazolyl, benzodioxazolyl, benzodioxinyl, benzimidazolyl, dihydrobenzothiophenyl, dihydrobenzofuranyl, purinyl, indolizinyl, chromanyl, chromenyl, dihydrobenzodioxinyl, etc., but is not limited thereto.

In the present invention, "cycloalkyl" may mean a saturated hydrocarbon ring generally having a specified number of carbon atoms containing a ring, and the saturated hydrocarbon ring may collectively refer to monocyclic and polycyclic structures, and a ring structure, in which at least two rings share at least one pair of carbon atoms.

Cycloalkyl may include cyclohexyl, cycloheptyl, cyclooctyl, tetrahydronaphthalenyl, adamantyl, etc., but is not limited thereto.

In the present invention, "heterocycloalkyl" may mean a saturated monocyclic and polycyclic hetero ring containing one to four hetero atoms independently selected from nitrogen (N), oxygen (O) and sulfur (S), or a ring structure, in which at least two rings share at least one pair of carbon atoms. Heterocycloalkyl may include oxiranyl, oxetanyl, morpholinyl, thietanyl, pyrrolidinyl, piperidinyl, piperazinyl, tetrahydrofuranyl, tetrahydrothiophenyl, tetrahydropyranyl, tetrahydrothiopyranyl, 6-azabicyclo[3.2.1]octanyl, etc., but is not limited thereto.

In the present invention, "cycloalkylene" may mean a divalent functional group derived from cycloalkyl, and "heterocycloalkylene" may refer to a divalent functional group derived from heterocycloalkyl.

The adamantane derivatives represented by formula 1 according to the present invention may be any one compound selected from the group consisting of the compounds shown in table 1 below.

| Example # | Name | Structure |
|---|---|---|
| 1 | 2-((2-((4-(((trans)-5-hydroxyadamantan-2-yl)amino)-2-methoxyphenyl)amino)-5-(trifluoromethyl)pyrimidin-4-yl)amino)-N,3-dimethylbenzamide | 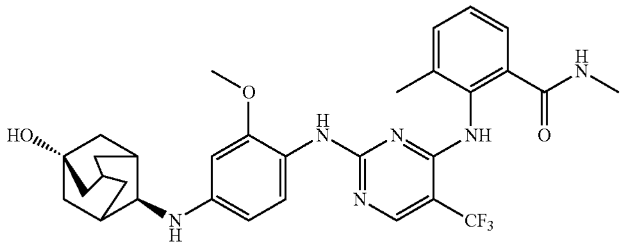 [SMILES: CNC(=O)c1cccc(C)c1Nc1nc(Nc2ccc(N[C@H]3C4CC5CC3C[C@@](O)(C5)C4)cc2OC)ncc1C(F)(F)F] |
| 2 | 2-((2-((4-(adamantan-2-ylamino)-2-methoxyphenyl)amino)-5-(trifluoromethyl)pyrimidin-4-yl)amino)-N,3-dimethylbenzamide | 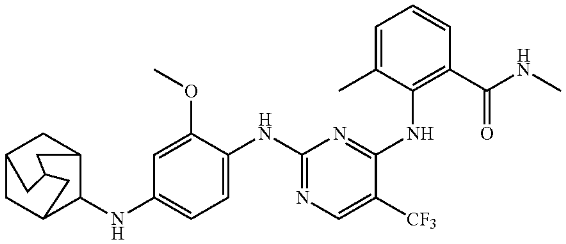 [SMILES: CNC(=O)c1cccc(C)c1Nc1nc(Nc2ccc(NC3C4CC5CC(C4)CC3C5)cc2OC)ncc1C(F)(F)F] |
| 3 | 2-((2-((4-(4-(adamantan-2-yl)piperazin-1-yl)-2-methoxyphenyl)amino)-5-(trifluoromethyl)pyrimidin-4-yl)amino)-N,3-dimethylbenzamide | 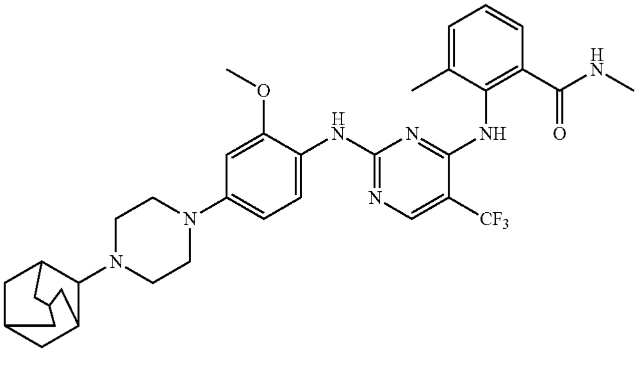 [SMILES: CNC(=O)c1cccc(C)c1Nc1nc(Nc2ccc(N3CCN(C4C5CC6CC(C5)CC4C6)CC3)cc2OC)ncc1C(F)(F)F] |

-continued

| Example # | Name | Structure |
|---|---|---|
| 4 | 2-((2-((4-(4-((trans)-5-hydroxyadamantan-2-yl)piperazin-1-yl)-2-methoxyphenyl)amino)-5-(trifluoromethyl)pyrimidin-4-yl)amino)-N,3-dimethylbenzamide | 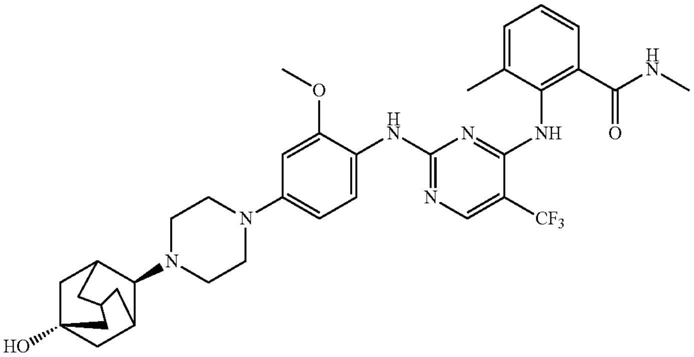 [SMILES: CNC(=O)c1cccc(C)c1Nc1nc(Nc2ccc(N3CCN([C@H]4C5CC6CC4C[C@](O)(C6)C5)CC3)cc2OC)ncc1C(F)(F)F] |
| 5 | 2-((2-((4-(4-((cis)-5-hydroxyadamantan-2-yl)piperazin-1-yl)-2-methoxyphenyl)amino)-5-(trifluoromethyl)pyrimidin-4-yl)amino)-N,3-dimethylbenzamide | 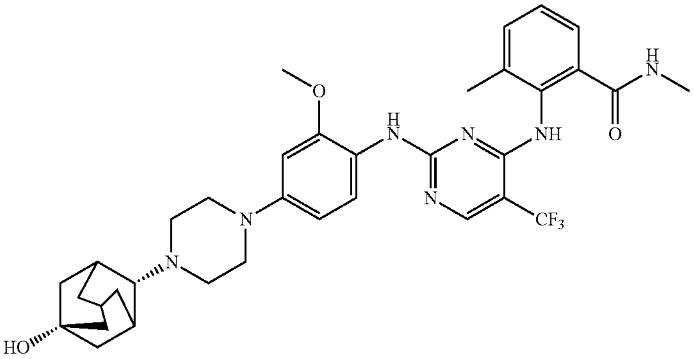 [SMILES: CNC(=O)c1cccc(C)c1Nc1nc(Nc2ccc(N3CCN([C@H]4C5CC6CC4C[C@@](O)(C6)C5)CC3)cc2OC)ncc1C(F)(F)F] |
| 6 | 2-((2-((4-((1-(adamantan-2-yl)piperidin-4-yl)amino)-2-methoxyphenyl)amino)-5-(trifluoromethyl)pyrimidin-4-yl)amino)-N,3-dimethylbenzamide | 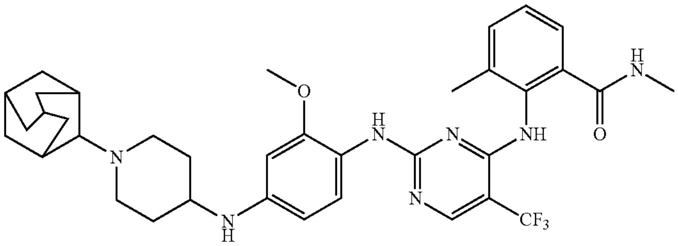 [SMILES: CNC(=O)c1cccc(C)c1Nc1nc(Nc2ccc(NC3CCN(C4C5CC6CC(C5)CC4C6)CC3)cc2OC)ncc1C(F)(F)F] |
| 7 | 2-((2-((4-((1-((trans)-5-hydroxyadamantan-2-yl)piperidin-4-yl)amino)-2-methoxyphenyl)amino)-5-(trifluoromethyl)pyrimidin-4-yl)amino)-N,3-dimethylbenzamide | 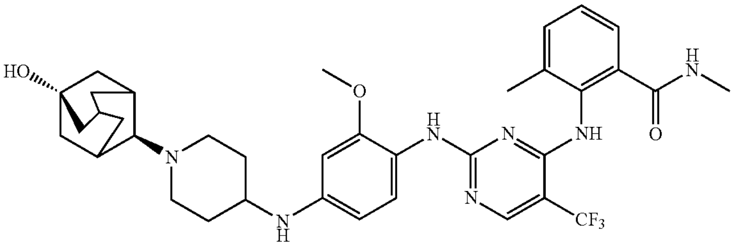 [SMILES: CNC(=O)c1cccc(C)c1Nc1nc(Nc2ccc(NC3CCN([C@H]4C5CC6CC4C[C@](O)(C6)C5)CC3)cc2OC)ncc1C(F)(F)F] |
| 8 | 2-((2-((4-((1-((cis)-5-hydroxyadamantan-2-yl)piperidin-4-yl)amino)-2-methoxyphenyl)amino)-5-(trifluoromethyl)pyrimidin-4-yl)amino)-N,3-dimethylbenzamide | 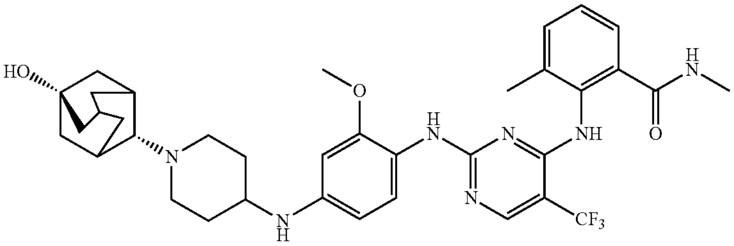 [SMILES: CNC(=O)c1cccc(C)c1Nc1nc(Nc2ccc(NC3CCN([C@H]4C5CC6CC4C[C@@](O)(C6)C5)CC3)cc2OC)ncc1C(F)(F)F] |

-continued

| Example # | Name | Structure |
|---|---|---|
| 9 | 2-((2-((4-((1-(adamantan-2-yl)piperidin-4-yl)oxy)-2 -methoxyphenyl)amino)-5-(trifluoromethyl)pyrimidin-4-yl)amino)-N,3-dimethylbenzamide | 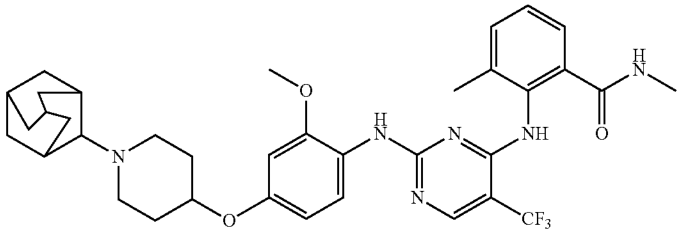 [SMILES: CNC(=O)c1cccc(C)c1Nc1nc(Nc2ccc(OC3CCN(C4C5CC6CC(C5)CC4C6)CC3)cc2OC)ncc1C(F)(F)F] |
| 10 | 2-((2-((2-methoxy-4-((4-oxoadamantan-1-yl)oxy)phenyl)amino)-5-(trifluoromethyl)pyrimidin-4-yl)amino)-N,3-dimethylbenzamide | 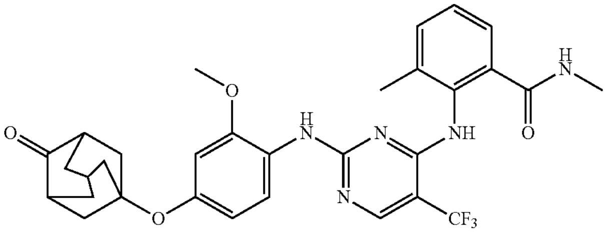 [SMILES: CNC(=O)c1cccc(C)c1Nc1nc(Nc2ccc(OC34CC5CC(C3)C(=O)C(C5)C4)cc2OC)ncc1C(F)(F)F] |
| 11 | 2-((2-((4-((4-hydroxyadamantan-1-yl)oxy)-2-methoxyphenyl)amino)-5-(trifluoromethyl)pyrimidin-4-yl)amino)-N,3-dimethylbenzamide | 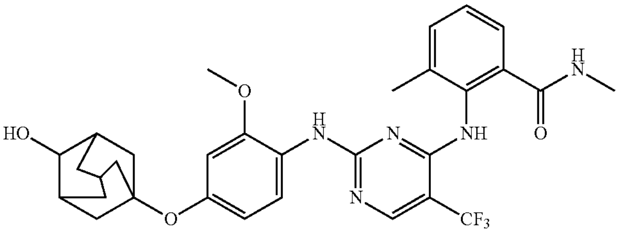 [SMILES: CNC(=O)c1cccc(C)c1Nc1nc(Nc2ccc(OC34CC5CC(C3)C(O)C(C5)C4)cc2OC)ncc1C(F)(F)F] |
| 12 | 2-((2-((2-methoxy-4-((4-morpholinoadamantan-1-yl)oxy)phenyl)amino)-5-(trifluoromethyl)pyrimidin-4-yl)amino)-N,3-dimethylbenzamide | 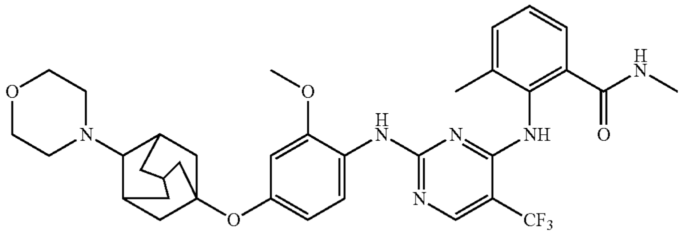 [SMILES: CNC(=O)c1cccc(C)c1Nc1nc(Nc2ccc(OC34CC5CC(C3)C(N3CCOCC3)C(C5)C4)cc2OC)ncc1C(F)(F)F] |
| 13 | 2-((2-((2-methoxy-4-((4-(4-methylpiperazin-1-yl)adamantan-1-yl)oxy)phenyl)amino)-5-(trifluoromethyl)pyrimidin-4-yl)amino)-N,3-dimethylbenzamide | 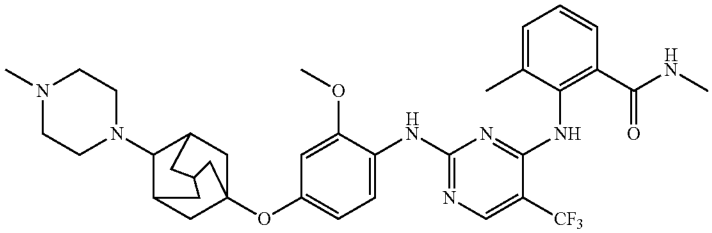 |
| 14 | 2-((2-((4-(((trans)-4-((S)-3-acetamidopyrrolidin-1-yl)adamantan-1-yl)oxy)-2-methoxyphenyl)amino)-5-(trifluoromethyl)pyrimidin-4-yl)amino)-N,3-dimethylbenzamide | 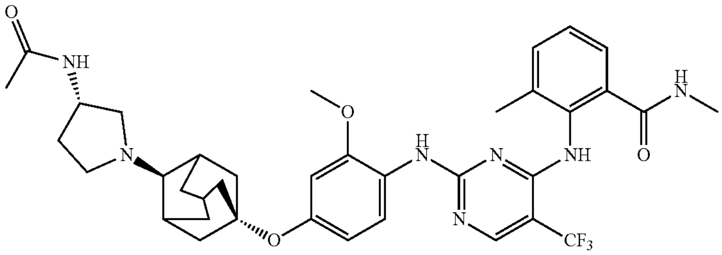 [SMILES: CNC(=O)c1cccc(C)c1Nc1nc(Nc2ccc(O[C@]34CC5CC(C3)[C@@H](N3CC[C@H](NC(C)=O)C3)C(C5)C4)cc2OC)ncc1C(F)(F)F] |

-continued

| Example # | Name | Structure |
|---|---|---|
| 15 | 2-((2-((4-(((cis)-4-((S)-3-acetamidopyrrolidin-1-yl)adamantan-1-yl)oxy)-2-methoxyphenyl)amino)-5-(trifluoromethyl)pyrimidin-4-yl)amino)-N,3-dimethylbenzamide | 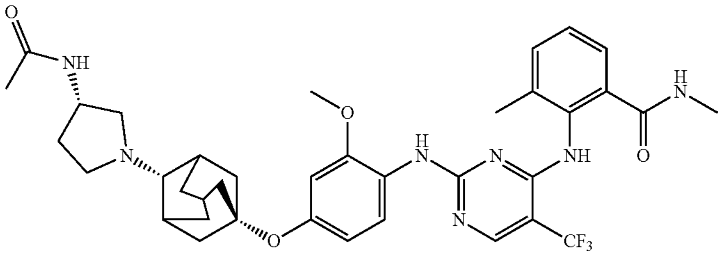 [SMILES: CNC(=O)c1cccc(C)c1Nc1nc(Nc2ccc(O[C@]34CC5CC(C3)[C@H](N3CC[C@H](NC(C)=O)C3)C(C5)C4)cc2OC)ncc1C(F)(F)F] |
| 16 | 4-(3-methoxy-4-((4-((2-methyl-6-(methylcarbamoyl)phenyl)amino)-5-(trifluoromethyl)pyrimidin-2-yl)amino)phenoxy)adamantan-1-methyl carboxylate | 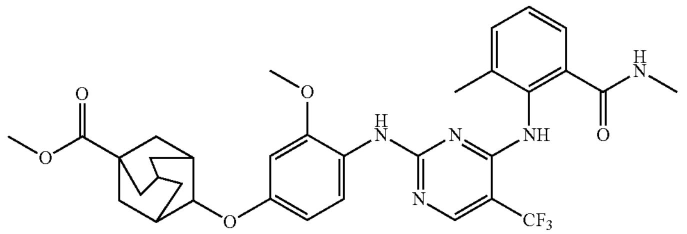 |
| 17 | 4-(3-methoxy-4-((4-((2-methyl-6-(methylcarbamoyl)phenyl)amino)-5-(trifluoromethyl)pyrimidin-2-yl)amino)phenoxy)adamantan-1-carboxylic acid | 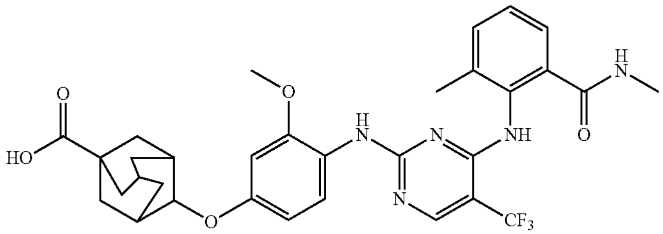 [SMILES: CNC(=O)c1cccc(C)c1Nc1nc(Nc2ccc(OC3C4CC5CC3CC(C(=O)O)(C5)C4)cc2OC)ncc1C(F)(F)F] |
| 18 | 4-(3-methoxy-4-((4-((2-methyl-6-(methylcarbamoyl)phenyl)amino)-5-(trifluoromethyl)pyrimidin-2-yl)amino)phenoxy)-N-methyladamantan-1-carboxamide | 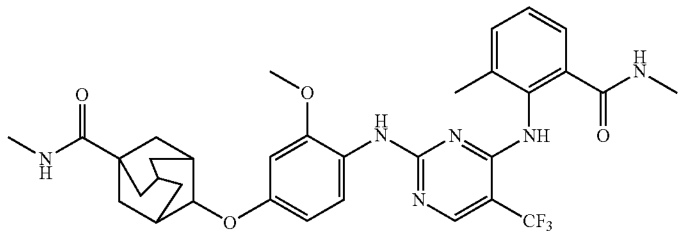 |
| 19 | 2-((2-((2-methoxy-4-((5-(morpholin-4-carbonyl)adamantan-2-yl)oxy)phenyl)amino)-5-(trifluoromethyl)pyrimidin-4-yl)amino)-N,3-dimethylbenzamide | 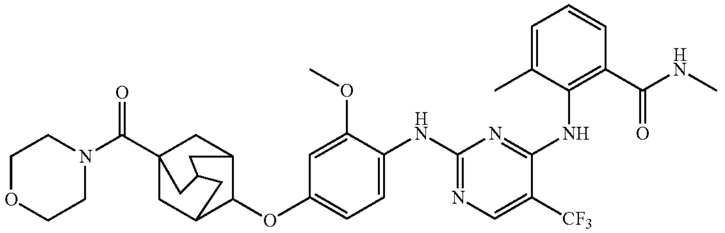 [SMILES: CNC(=O)c1cccc(C)c1Nc1nc(Nc2ccc(OC3C4CC5CC3CC(C(=O)N3CCOCC3)(C5)C4)cc2OC)ncc1C(F)(F)F] |
| 20 | 2-((2-((2-methoxy-4-((5-(4-methylpiperazin-1-carbonyl)adamantan-2-yl)oxy)phenyl)amino)-5-(trifluoromethyl)pyrimidin-4-yl)amino)-N,3-dimethylbenzamide | 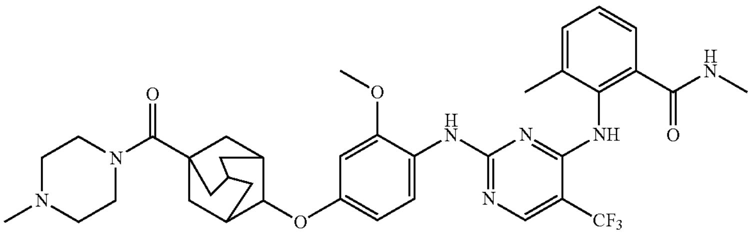 |

-continued

| Example # | Name | Structure |
|---|---|---|
| 21 | 2-((2-((2-methoxy-4-((5-((S)-3-acetamidopyrrolidin-1-carbonyl)adamantan-2-yl)oxy)phenyl)amino)-5-(trifluoromethyl)pyrimidin-4-yl)amino)-N,3-dimethylbenzamide | 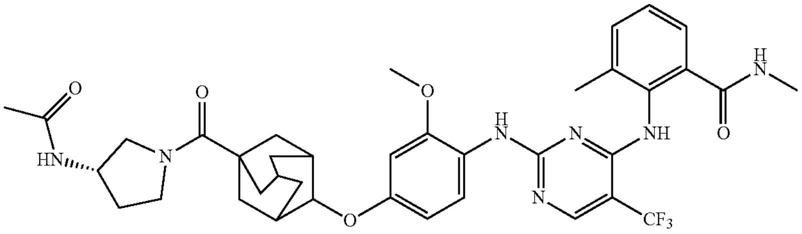 [SMILES: CNC(=O)c1cccc(C)c1Nc1nc(Nc2ccc(OC3C4CC5CC3CC(C(=O)N3CC[C@H](NC(C)=O)C3)(C5)C4)cc2OC)ncc1C(F)(F)F] |
| 22 | 2-((2-((2-methoxy-4-((5-(morpholin-4-carbonyl)adamantan-2-yl)amino)phenyl)amino)-5-(trifluoromethyl)pyrimidin-4-yl)amino)-N,3-dimethylbenzamide | 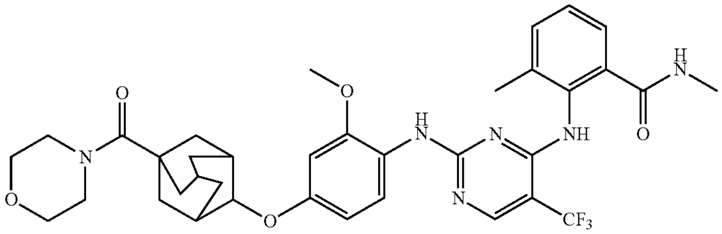 [SMILES: CNC(=O)c1cccc(C)c1Nc1nc(Nc2ccc(OC3C4CC5CC3CC(C(=O)N3CCOCC3)(C5)C4)cc2OC)ncc1C(F)(F)F] |
| 23 | 2-((2-((2-methoxy-4-((5-(4-methylpiperazin-1-carbonyl)adamantan-2-yl)amino)phenyl)amino)-5-(trifluoromethyl)pyrimidin-4-yl)amino)-N,3-dimethylbenzamide | 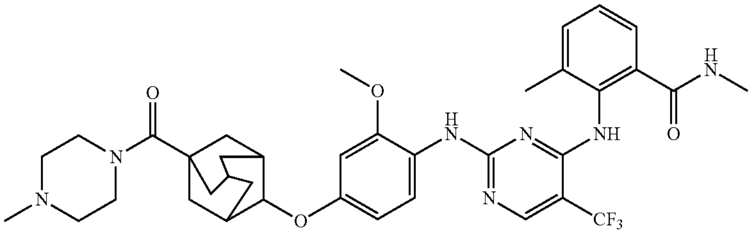 |
| 24 | 2-((2-((2-methoxy-4-((5-((S)-3-acetamidopyrrolidin-1-carbonyl)adamantan-2-yl)amino)phenyl)amino)-5-(trifluoromethyl)pyrimidin-4-yl)amino)-N,3-dimethylbenzamide | 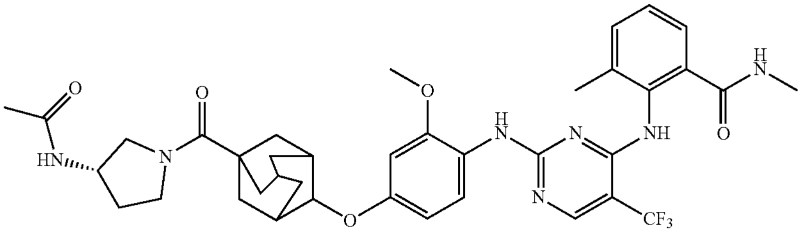 [SMILES: CNC(=O)c1cccc(C)c1Nc1nc(Nc2ccc(OC3C4CC5CC3CC(C(=O)N3CC[C@H](NC(C)=O)C3)(C5)C4)cc2OC)ncc1C(F)(F)F] |
| 25 | N-(3-methoxy-4-((4-((2-methyl-6-(methylcarbamoyl)phenyl)amino)-5-(trifluoromethyl)pyrimidin-2-yl)amino)phenyl)-4-morpholinoadamantan-1-carboxamide | 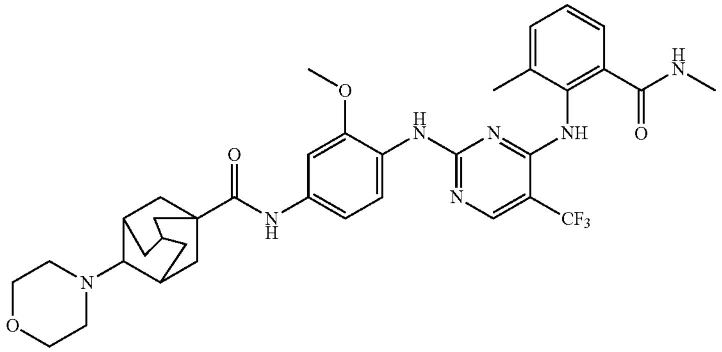 [SMILES: CNC(=O)c1cccc(C)c1Nc1nc(Nc2ccc(NC(=O)C34CC5CC(C3)C(N3CCOCC3)C(C5)C4)cc2OC)ncc1C(F)(F)F] |

-continued

| Example # | Name | Structure |
|---|---|---|
| 26 | N-(3-methoxy-4-((4-((2-methyl-6-(methylcarbamoyl)phenyl)amino)-5-(trifluoromethyl)pyrimidin-2-yl)amino)phenyl)-4-(4-methylpiperazin-1-yl)adamantan-1-carboxamide | 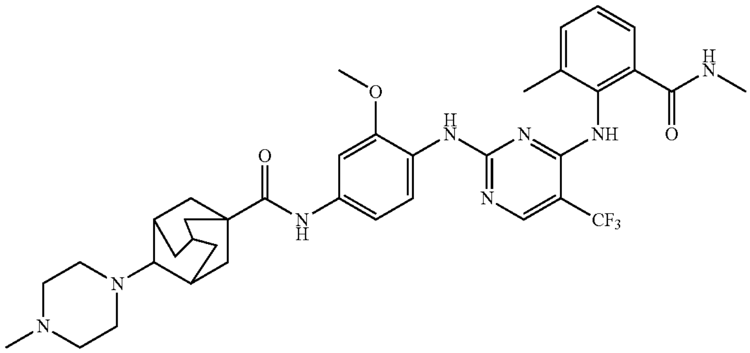 |
| 27 | (trans)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl)adamantan-1-carboxamide | 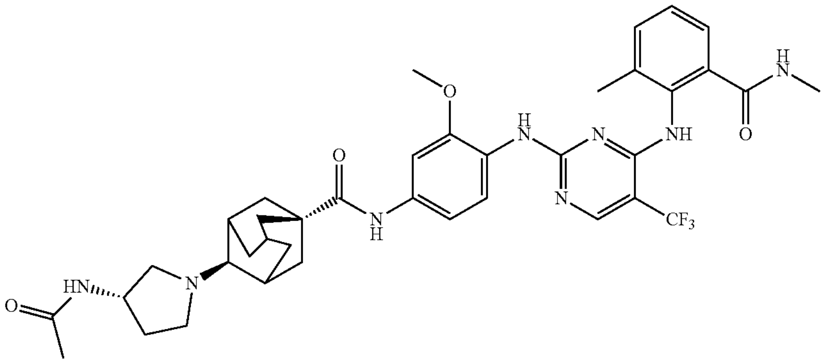 [SMILES: CNC(=O)c1cccc(C)c1Nc1nc(Nc2ccc(NC(=O)[C@]34CC5CC(C3)[C@@H](N3CC[C@H](NC(C)=O)C3)C(C5)C4)cc2OC)ncc1C(F)(F)F] |
| 28 | (cis)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl)adamantan-1-carboxamide | 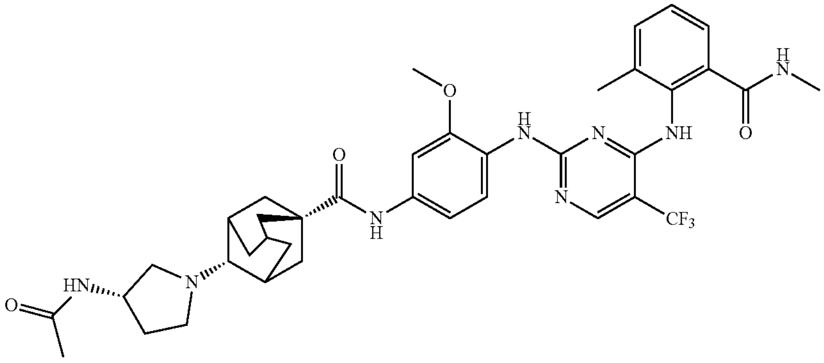 [SMILES: CNC(=O)c1cccc(C)c1Nc1nc(Nc2ccc(NC(=O)[C@]34CC5CC(C3)[C@H](N3CC[C@H](NC(C)=O)C3)C(C5)C4)cc2OC)ncc1C(F)(F)F] |
| 29 | 4-hydroxy-N-(3-methoxy-4-((4-((2-methyl-6-(methylcarbamoyl)phenyl)amino)-5-(trifluoromethyl)pyrimidin-2-yl)amino)phenyl)adamantan-1-carboxamide | 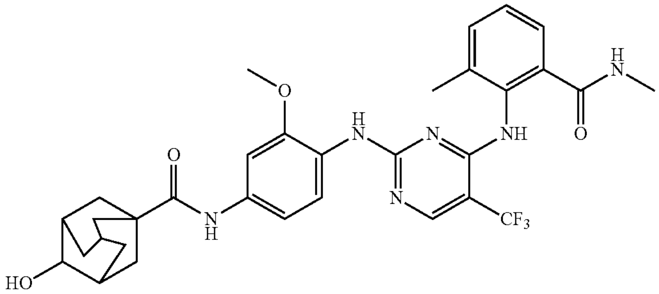 [SMILES: CNC(=O)c1cccc(C)c1Nc1nc(Nc2ccc(NC(=O)C34CC5CC(C3)C(O)C(C5)C4)cc2OC)ncc1C(F)(F)F] |

-continued

| Example # | Name | Structure |
|---|---|---|
| 30 | (trans)-4-((S)-3-aminopyrrolidin-1-yl)-N-(3-methoxy-4-((4-((2-methyl-6-(methylcarbamoyl)phenyl)amino)-5-(trifluoromethyl)pyrimidin-2-yl)amino)phenyl)adamantan-1-carboxamide | 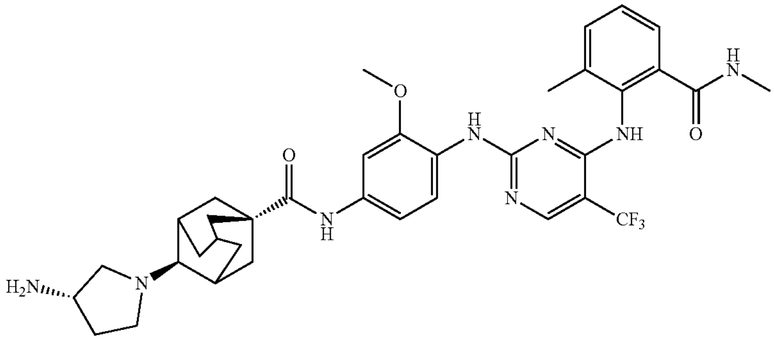 [SMILES: CNC(=O)c1cccc(C)c1Nc1nc(Nc2ccc(NC(=O)[C@]34CC5CC(C3)[C@@H](N3CC[C@H](N)C3)C(C5)C4)cc2OC)ncc1C(F)(F)F] |
| 31 | (cis)-4-((S)-3-aminopyrrolidin-1-yl)-N-(3-methoxy-4-((4-((2-methyl-6-(methylcarbamoyl)phenyl)amino)-5-(trifluoromethyl)pyrimidin-2-yl)amino)phenyl)adamantan-1-carboxamide | 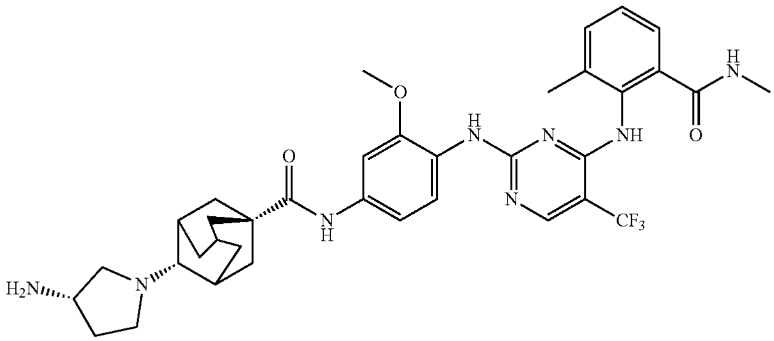 [SMILES: CNC(=O)c1cccc(C)c1Nc1nc(Nc2ccc(NC(=O)[C@]34CC5CC(C3)[C@H](N3CC[C@H](N)C3)C(C5)C4)cc2OC)ncc1C(F)(F)F] |
| 32 | 2-((2-((4-(1-((trans)-5-hydroxyadamantan-2-yl)piperidin-4-yl)-2-methoxyphenyl)amino)-5-(trifluoromethyl)pyrimidin-4-yl)amino)-N,3-dimethylbenzamide | 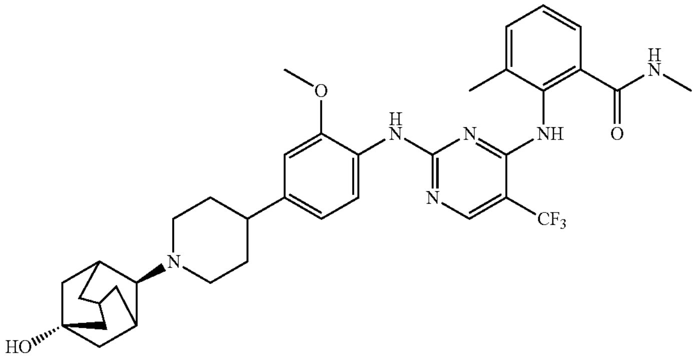 [SMILES: CNC(=O)c1cccc(C)c1Nc1nc(Nc2ccc(C3CCN([C@H]4C5CC6CC4C[C@@](O)(C6)C5)CC3)cc2OC)ncc1C(F)(F)F] |
| 33 | 2-((2-((4-(1-((cis)-5-hydroxyadamantan-2-yl)piperidin-4-yl)-2-methoxyphenyl)amino)-5-(trifluoromethyl)pyrimidin-4-yl)amino)-N,3-dimethylbenzamide | 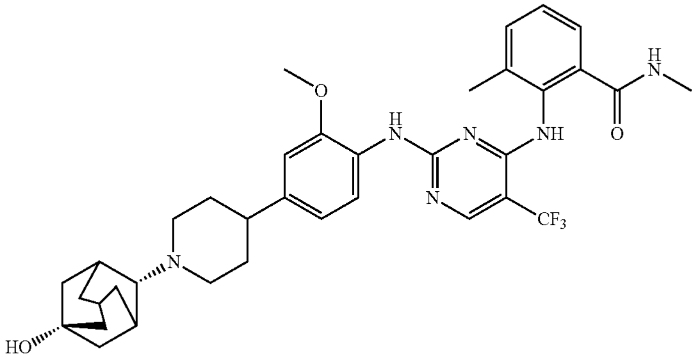 |

-continued

| Example # | Name | Structure |
|---|---|---|
| 34 | 2-((2-((4-(1-((trans)-5-hydroxyadamantan-2-yl)piperidin-4-yl)-2-methoxyphenyl)amino)-5-(trifluoromethyl)pyrimidin-4-yl)amino)-3-methylbenzamide | 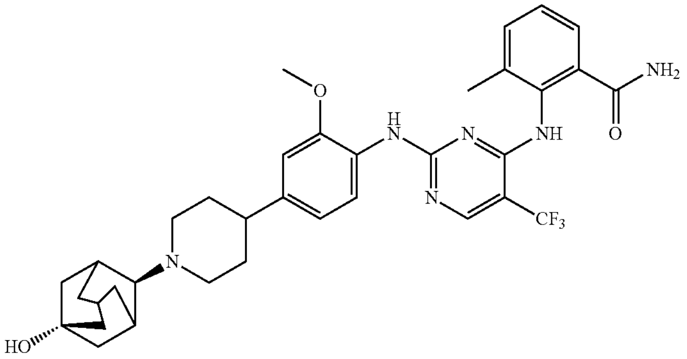 [SMILES: COc1cc(C2CCN([C@H]3C4CC5CC3C[C@@](O)(C5)C4)CC2)ccc1Nc1ncc(C(F)(F)F)c(Nc2c(C)cccc2C(N)=O)n1] |
| 35 | 2-((2-((4-(1-((cis)-5-hydroxyadamantan-2-yl)piperidin-4-yl)-2-methoxyphenyl)amino)-5-(trifluoromethyl)pyrimidin-4-yl)amino)-3-methylbenzamide | 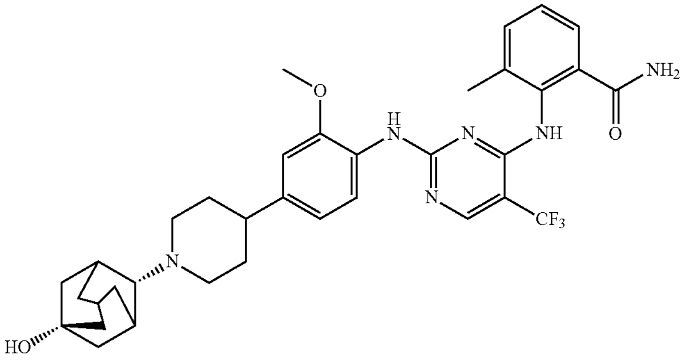 [SMILES: COc1cc(C2CCN([C@H]3C4CC5CC3C[C@](O)(C5)C4)CC2)ccc1Nc1ncc(C(F)(F)F)c(Nc2c(C)cccc2C(N)=O)n1] |
| 36 | 2-((5-chloro-2-((4-(4-((trans)-5-hydroxyadamantan-2-yl)piperazin-1-yl)-2-methoxyphenyl)amino)-pyrimidin-4-yl)amino)-N,3-dimethylbenzamide | 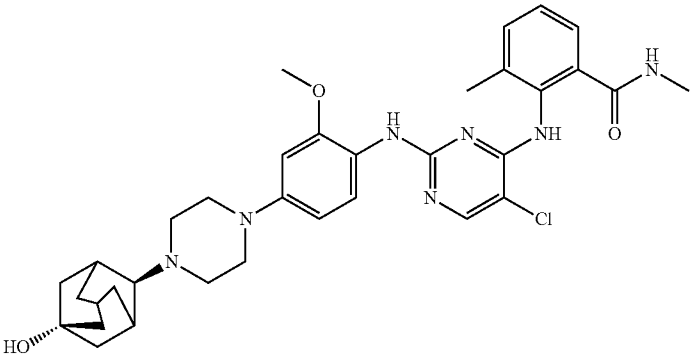 |
| 37 | methyl(trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantan-1-carboxylate | 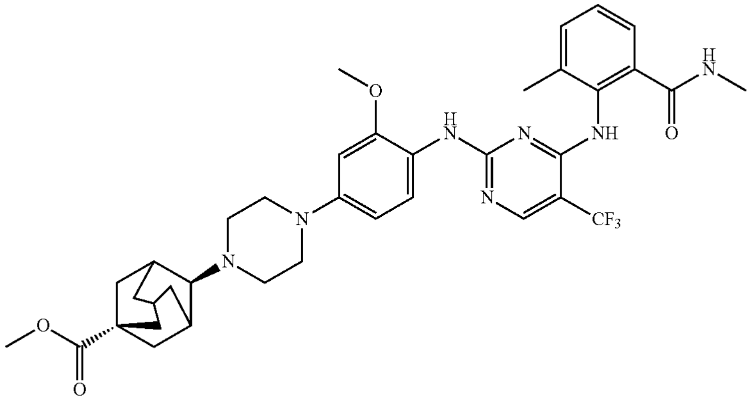 |

-continued

| Example # | Name | Structure |
|---|---|---|
| 38 | methyl(cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantan-1-carboxylate | 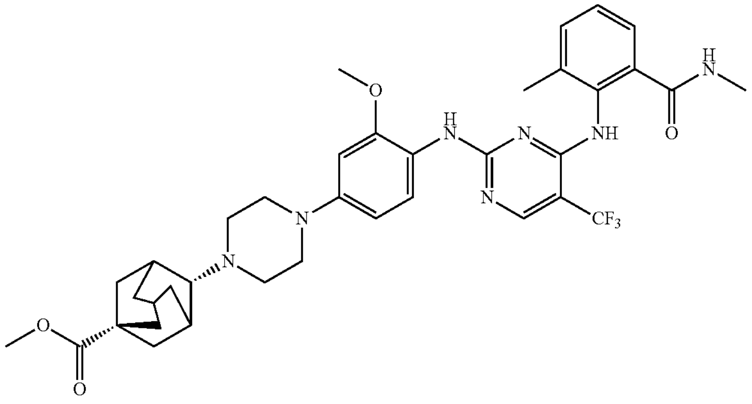 |
| 39 | (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantan-1-carboxylic acid | 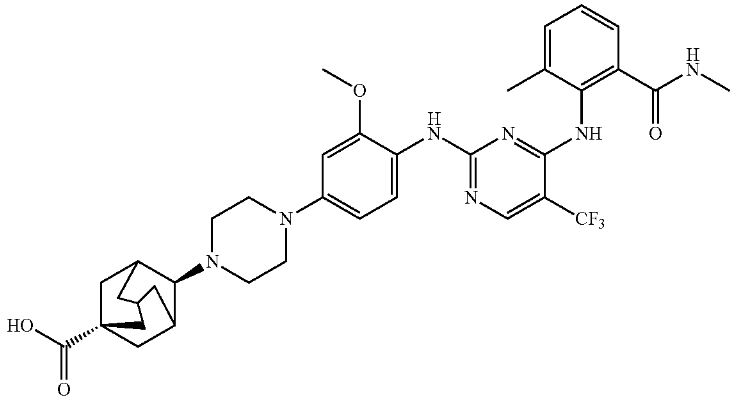 [SMILES: CNC(=O)c1cccc(C)c1Nc1nc(Nc2ccc(N3CCN([C@H]4C5CC6CC4C[C@@](C(=O)O)(C6)C5)CC3)cc2OC)ncc1C(F)(F)F] |
| 40 | (cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantan-1-carboxylic acid | 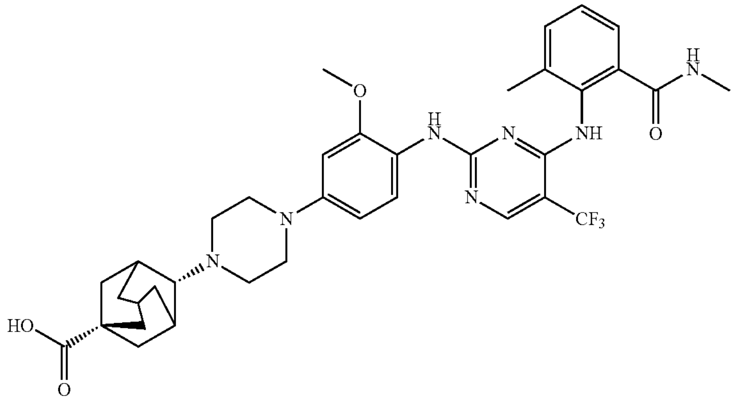 |

-continued

| Example # | Name | Structure |
| --- | --- | --- |
| 41 | 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)-N-methyladamantan-1-carboxamide | 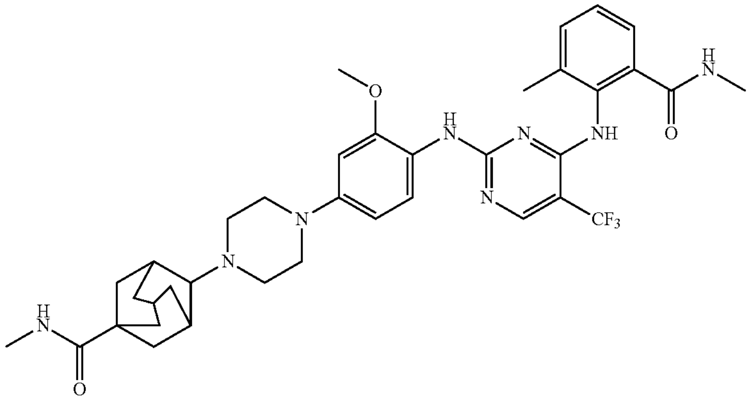 |
| 42 | 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantan-1-carboxamide | 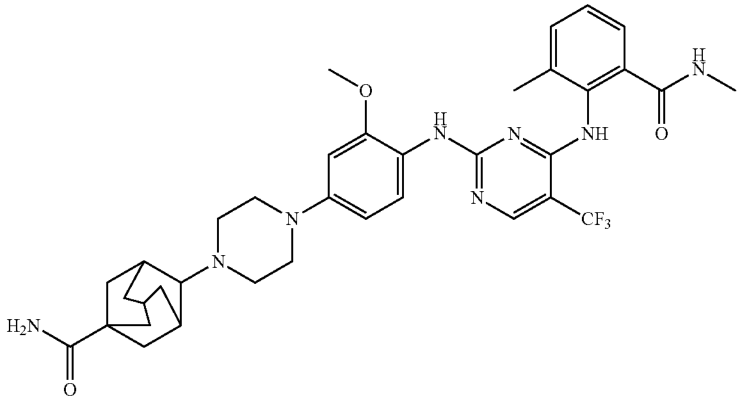 [SMILES: CNC(=O)c1cccc(C)c1Nc1nc(Nc2ccc(N3CCN(C4C5CC6CC4CC(C(N)=O)(C6)C5)CC3)cc2OC)ncc1C(F)(F)F] |
| 43 | 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)-N,N-dimethyladamantan-1-carboxamide | 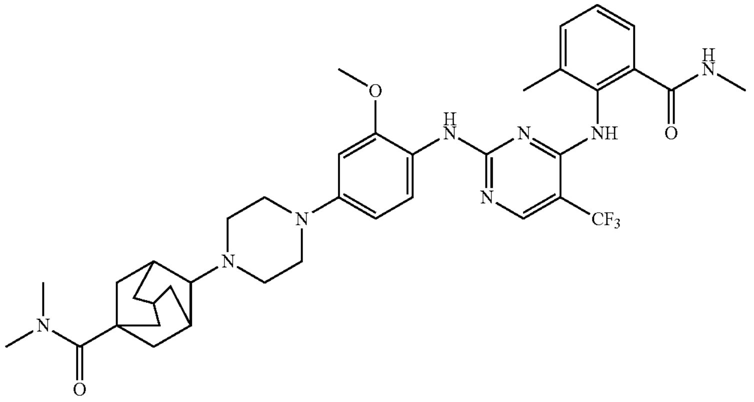 |
| 44 | 2-((2-((4-(4-(5-aminoadamantan-2-yl)piperazin-1-yl)-2-methoxyphenyl)amino)-5-(trifluoromethyl)pyrimidin-4-yl)amino)-N,3-dimethylbenzamide | 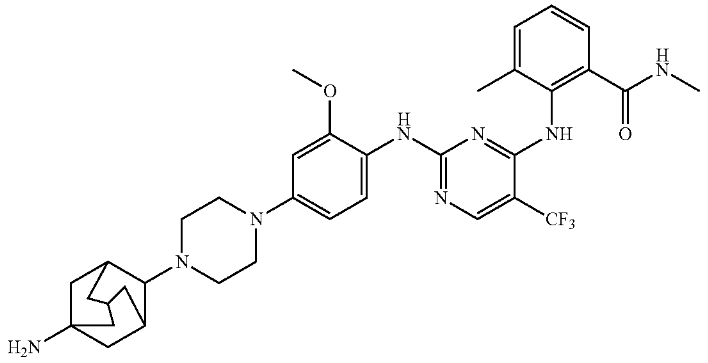 [SMILES: CNC(=O)c1cccc(C)c1Nc1nc(Nc2ccc(N3CCN(C4C5CC6CC4CC(N)(C6)C5)CC3)cc2OC)ncc1C(F)(F)F] |

-continued

| Example # | Name | Structure |
| --- | --- | --- |
| 45 | 2-((2-((4-(4-(5-(methylamino)adamantan-2-yl)piperazin-1-yl)-2-methoxyphenyl)amino)-5-(trifluoromethyl)pyrimidin-4-yl)amino)-N,3-dimethylbenzamide | 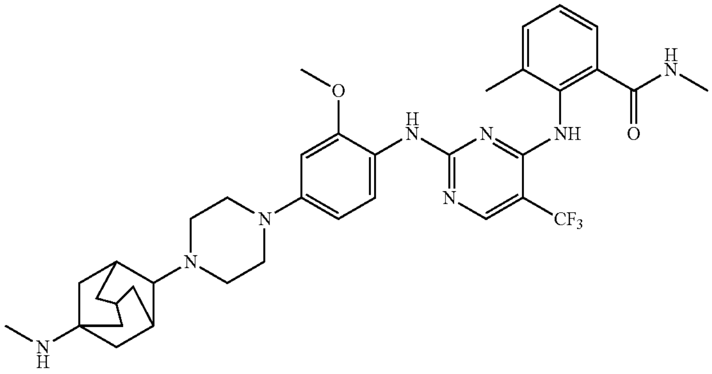 |
| 46 | 2-((2-((4-(4-(5-(dimethylamino)adamantan-2-yl)piperazin-1-yl)-2-methoxyphenyl)amino)-5-(trifluoromethyl)pyrimidin-4-yl)amino)-N,3-dimethylbenzamide | 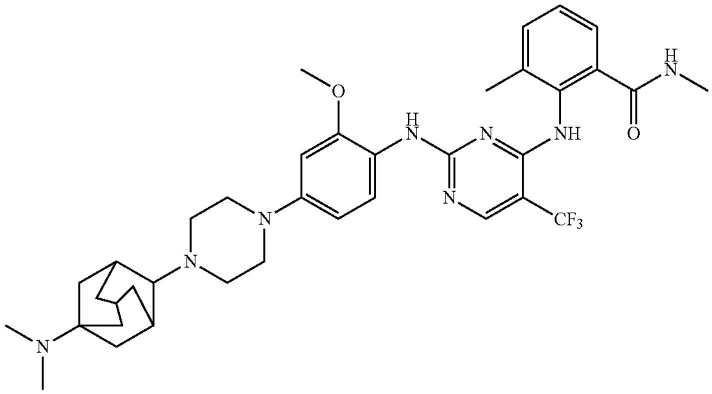 |
| 47 | 2-((2-((4-(4-(5-acrylamidoadamantan-2 -yl)piperazin-1-yl)-2-methoxyphenyl)amino)-5-(trifluoromethyl)pyrimidin-4-yl)amino)-N,3-dimethylbenzamide | 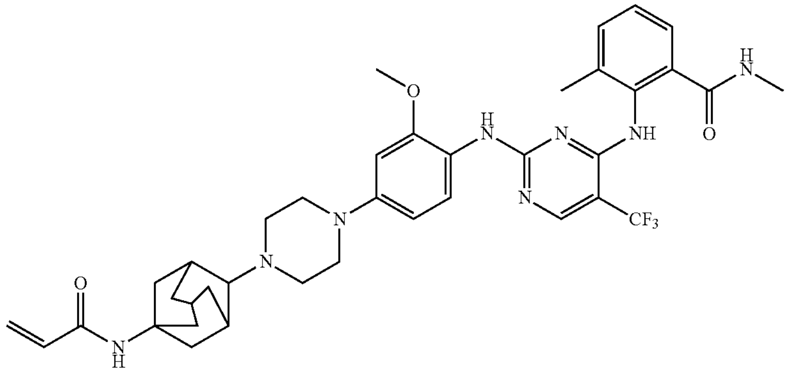 [SMILES: C=CC(=O)NC12CC3CC(C1)C(N1CCN(c4ccc(Nc5ncc(C(F)(F)F)c(Nc6c(C)cccc6C(=O)NC)n5)c(OC)c4)CC1)C(C3)C2] |

In the present invention, "stereoisomer" may include a diastereomer and an optical isomer, in which the optical isomer may include not only an enantiomer, but also a mixture of the enantiomer and even a racemate.

In the present invention, "pharmaceutically acceptable salts" may refer to the salts conventionally used in a pharmaceutical industry, for example, inorganic ion salts prepared from calcium, potassium, sodium, magnesium and the like; inorganic acid salts prepared from hydrochloric acid, nitric acid, phosphoric acid, bromic acid, iodic acid, perchloric acid, hydroiodic acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbric acid, carbonic acid, vanillic acid, and the like; sulfonic acid salts prepared from methanesulfonic acid, ethanesulfonic acid, benzenesulfonic acid, p-toluenesulfonic acid, naphthalenesulfonic acid and the like; amino acid salts prepared from glycine, arginine, lysine, and the like; amine salts prepared from trimethylamine, triethylamine, ammonia, pyridine, picoline, and the like; and the like, but types of salts meant in the present invention are not limited to those listed salts.

The "hydrate" of the present invention may refer to one, in which adamantane derivatives, isomers thereof or pharmaceutically acceptable salts thereof and water are bound by a non-covalent intermolecular force, and may include a stoichiometric or non-stoichiometric amount of water. Particularly, the hydrate may contain water at a molar ratio of about 0.25 mol to about 10 mol based on 1 mol of an active ingredient, more particularly about 0.5 mol, about 1 mol, about 1.5 mol, about 2 mol, about 2.5 mol, 3 mol, about 5 mol, etc.

The "solvate" of the present invention may refer to one, in which adamantane derivatives, isomers thereof or pharmaceutically acceptable salts thereof and a solvent other than water are bound by an intermolecular force, and may include a stoichiometric or non-stoichiometric amount of solvent. Particularly, the solvate may contain a solvent molecule at a molar ratio of about 0.25 mol to about 10 mol based on 1 mol of an active ingredient, more particularly about 0.5 mol, about 1 mol, about 1.5 mol, about 2 mol, about 2.5 mol, about 3 mol, about 5 mol, etc.

In the present invention, "inhibitor" may refer to a compound that blocks or reduces the activity of an enzyme. The inhibitor may be capable of reversible or irreversible binding, and thus the term may include a compound that kills the substrate of the enzyme. The inhibitor may modify one or more sites on or near an enzyme active site, or may result in a conformational change elsewhere on the enzyme.

Composition Including Adamantane Derivative Compound, Use Thereof and Therapeutic Method Using the Same The present invention provides a pharmaceutical composition including adamantane derivatives, pharmaceutically acceptable salts thereof, stereoisomers thereof, hydrates or solvates thereof as active ingredients.

The present invention provides a pharmaceutical composition for preventing or treating FAK activity-associated diseases, including adamantane derivatives, pharmaceutically acceptable salts thereof, stereoisomers thereof, hydrates or solvates thereof as active ingredients.

In addition, the adamantane derivatives, stereoisomers thereof or pharmaceutically acceptable salts thereof according to the present invention may inhibit the activity of at least one of FAK and Pyk2(FAK2).

The FAK activity-associated diseases may be abnormal cell growth diseases induced by the abnormal activity of the FAK, and may be at least one selected from the group consisting of autoimmune disease, inflammatory disease, bone disease, metabolic disease, neurological and neurodegenerative disease, cancer, cardiovascular disease, allergy and asthma, Alzheimer's disease, viral disease and hormone-associated disease, preferably any one selected from the group consisting of solid cancers including gastric cancer, lung cancer, liver cancer, colorectal cancer, small intestine cancer, pancreatic cancer, brain cancer, bone cancer, melanoma, breast cancer, uterine cancer, cervical cancer, ovarian cancer, head and neck cancer, thyroid cancer, parathyroid cancer, kidney cancer, prostate cancer, urethral cancer, bladder cancer, mesothelioma, etc., and blood cancers including leukemia, multiple myeloma, lymphoma, etc. More preferably, the abnormal cell growth diseases induced by the abnormal activity of the FAK may be any one selected from the group consisting of highly invasive and metastatic triple-negative breast cancer, colorectal cancer, lung cancer and malignant mesothelioma. In addition, the above diseases may include symptoms or diseases related to the abnormal functions of the FAK.

The present invention provides a use of adamantane derivatives according to the present invention, pharmaceutically acceptable salts thereof, stereoisomers thereof, hydrates or solvates thereof for preventing or treating FAK activity-associated diseases.

In addition, the present invention provides a method for preventing or treating FAK activity-associated diseases, including administering a therapeutically effective amount of adamantane derivatives, pharmaceutically acceptable salts thereof, stereoisomers thereof, hydrates or solvates thereof into an individual.

As used herein, the term "prevention" means all the acts, which inhibit FAK activity-associated diseases or delay the occurrence thereof by administering the compound according to the present invention.

As used herein, the term "treatment" means all the acts, by which a symptom of FAK activity-associated diseases gets better or takes a favorable turn by administering the compound according to the present invention.

In addition, the present invention provides a method for inhibiting FAK and Pyk2(FAK2) activities, including administering adamantane derivatives, stereoisomers thereof or pharmaceutically acceptable salts thereof into an individual.

The method for preventing or treating FAK activity-associated diseases according to the present invention includes not only dealing with the diseases per se before expression of symptoms, but also inhibiting or avoiding such symptoms by administering an adamantane derivative compound, pharmaceutically acceptable salts thereof, stereoisomers thereof, hydrates or solvates thereof. In managing the diseases, a preventive or therapeutic dose of a certain active ingredient may vary depending on a nature and severity of the diseases or conditions and a route of administering the active ingredient. A dose and a frequency thereof may vary depending on an individual patient's age, weight and reactions. A suitable dose and usage may be easily selected by those skilled in the art, naturally considering such factors. In addition, the method for preventing or treating FAK activity-associated diseases according to the present invention may further include administering a therapeutically effective amount of an additional active agent, which is helpful in treating the diseases, along with adamantane derivatives, pharmaceutically acceptable salts thereof, stereoisomers thereof, hydrates or solvates thereof, and the additional active agent may exhibit a synergy effect or an adjuvant effect together with the adamantane derivatives, pharmaceutically acceptable salts thereof, stereoisomers thereof, hydrates or solvates thereof.

The present invention also provides a use of adamantane derivatives, pharmaceutically acceptable salts thereof, stereoisomers thereof, hydrates or solvates thereof for manufacture of a medicament for preventing or treating FAK activity-associated diseases. For preparing a medicament, adamantane derivatives, pharmaceutically acceptable salts thereof, stereoisomers thereof, hydrates or solvates thereof may be combined with acceptable adjuvants, diluents, carriers, etc., and may be prepared into a complex preparation together with other active agents and thus have a synergy action of active ingredients.

The pharmaceutical composition of the present invention may further include a pharmaceutically acceptable carrier.

In this case, the pharmaceutically acceptable carrier may be one which is conventionally used in formulating a preparation, including, but not limited thereto, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, tale, magnesium stearate, mineral oil and the like. In addition, the pharmaceutical composition of the present invention may further include lubricant, humectant, a sweetening agent, a flavoring agent, emulsifier, a suspending agent, preservative, etc. in addition to the above ingredients.

Furthermore, the pharmaceutical composition of the present invention may further include a medicament selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, and apoptosis inducer, and may be used in combination with the medicament further included above or may be formulated into a complex medication when being formulated into a medicament.

The pharmaceutical composition of the present invention may be orally or parenterally administered (for example, applied intravenously, hypodermically, intraperitoneally or locally) according to an intended method, in which a dosage thereof varies depending on a patient's condition and weight, a degree of disease, a drug form, and an administration route and time, but may be appropriately selected by those skilled in the art.

The pharmaceutical composition of the present invention is administered in a therapeutically effective amount.

In the present invention, the "therapeutically effective amount" may refer to an amount enough to treat a disease at a reasonable benefit/risk ratio applicable to medical treatment, and a level of effective dose may be determined according to factors including a patient's disease type, severity, activity of a drug, sensitivity to the drug, an administration time, an administration route and excretion rate, a treatment period and a concurrently used drug, as well as other factors well known in a medical field. The pharmaceutical composition according to the present invention may be administered as an individual therapeutic agent or in combination with other therapeutic agents, may be administered sequentially or simultaneously with a conventional therapeutic agent, and may be administered in a single or multiple manner. Considering all the factors above, it is important to carry out an administration by an amount, in which the maximum effect may be achieved by the minimum amount without a side effect, in which such amount may be easily determined by those skilled in the art.

Specifically, the effective amount of the pharmaceutical composition of the present invention may vary depending on a patient's age, gender, condition and weight, a degree of absorption of an active ingredient into the body, an inactivation rate and excretion rate, a disease type, and a concurrently used drug, and may be generally administered in an amount of 0.001 to 160 mg per 1 kg of body weight, preferably 0.01 to 100 mg, which may be administered everyday or every other day, or administered at one time to three times a day by dividing the daily dosage of the composition. However, the effective amount may increase or decrease depending on the route of administration, the severity of obesity, gender, weight, age, etc., and thus the dosage may not be intended to limit the scope of the present invention in any way.

In the present invention, "individual" may refer to a subject, whose disease needs to be prevented or treated, and more specifically to a mammal such as a human, monkey, mouse, dog, cat, horse, cow, etc., but is not limited thereto.

Matters mentioned in the use, composition and therapeutic method of the present invention may be equally applied, if not contradictory to each other. Besides, the terms and abbreviations used in the present specification have their original meanings, unless defined otherwise.

Hereinafter, the present invention will be described in detail through Examples for better understanding of the present invention. However, the following Examples are provided only for the purpose of illustrating the present invention, and thus the scope of the present invention is not limited thereto. The Examples of the present invention are provided to more completely describe the present invention to those having ordinary skill in the art.

EXAMPLE

<Example 1> Preparation of 2-((2-((4-(((trans)-5-hydroxyadamantan-2-yl)amino)-2-methoxyphenyl)amino)-5-(trifluoromethyl)pyrimidin-4-yl)amino)-N,3-dimethylbenzamide (compound i)

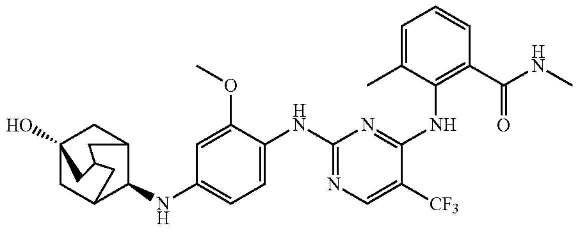 [SMILES: CNC(=O)c1cccc(C)c1Nc1nc(Nc2ccc(N[C@H]3C4CC5CC3C[C@](O)(C5)C4)cc2OC)ncc1C(F)(F)F]

[Step 1] Preparation of (trans)-4-((3-methoxy-4-nitrophenyl)amino) adamantan-1-ol

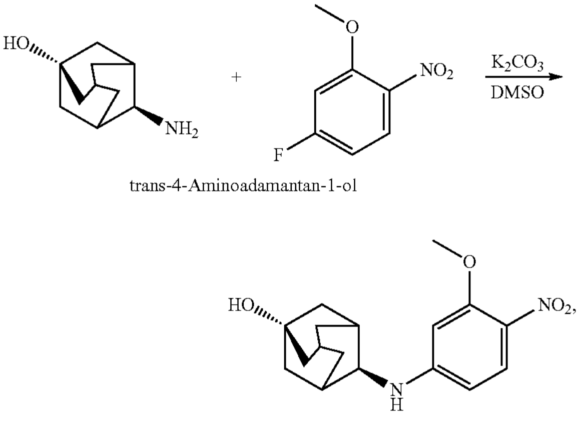

trans-4-Aminoadamantan-1-ol 4-fluoro-2-methoxy-1-nitrobenzene potassium carbonate and dimethylsulfoxide were heated to 120° C. for five hours while being well stirred. After cooling to room temperature, water was added to the reaction solution to precipitate while being well stirred, and the precipitated solid was obtained by filtration. The obtained solid was purified by column chromatography to obtain the title compound.

[Step 2] Preparation of (trans)-4-((4-amino-3-methoxyphenyl)amino) adamantan-1-ol

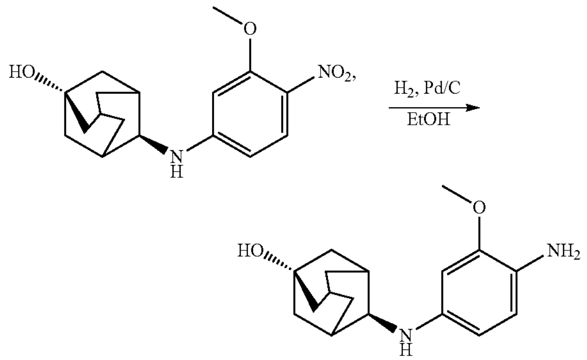

After dissolving (trans)-4-((3-methoxy-4-nitrophenyl) amino) adamantan-1-ol prepared in above step 1 in ethanol, 10% palladium/carbon catalyst was added thereto and stirred for 15 hours under hydrogen pressure. After completion of the reaction, the resulting solution was filtrated through celite and the filtrate was concentrated under reduced pressure and was immediately used in the next step without further purification.

[Step 3] Preparation of (trans)-4-((4-((4-chloro-5-(trifluoromethyl)pyrimidin-2-yl)amino)-3-methoxyphenyl)amino) adamantan-1-ol

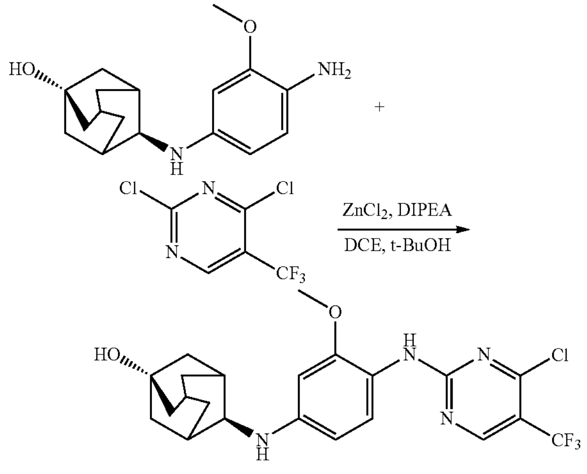

2,4-Dichloro-5-(trifluoromethyl)pyrimidine was dissolved in a mixed solvent of 1,2-dichloroethane and t-butanol (1:1), after which zinc dichloride was added and stirred at room temperature for 30 minutes. After cooling to 0° C., (trans)-4-((4-amino-3-methoxyphenyl)amino) adamantan-1-ol prepared in above step 2 was dissolved in a mixed solvent of 1,2-dichloroethane and t-butanol (1:1) and slowly added. After stirring at ° C. for one hour, diisopropylamine was added and stirred at room temperature for 15 hours. Ice water was poured into the reaction solution, extracted with dichloromethane, dried over anhydrous magnesium sulfate, and filtered, after which the filtrate was concentrated and purified by column chromatography to obtain the title compound.

[Step 4] Preparation of 2-((2-((4-(((trans)-5-hydroxyadamantan-2-yl)amino)-2-methoxyphenyl) amino)-5-(trifluoromethyl)pyrimidin-4-yl)amino)-N, 3-dimethylbenzamide

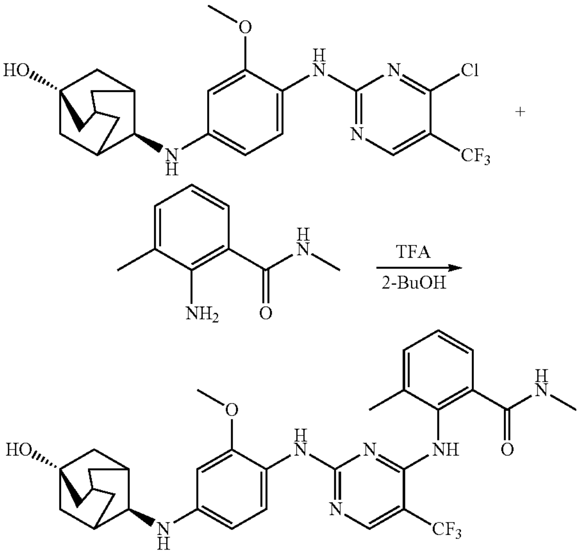

(trans)-4-((4-((4-Chloro-5-(trifluoromethyl)pyrimidin-2-yl)amino)-3-methoxyphenyl)amino) adamantan-1-ol prepared in above step 3 and 2-amino-N,3-dimethylbenzamide were dissolved in 2-butanol, after which trifluoroacetic acid was added and stirred under reflux for five hours. After cooling to room temperature, distilled water was added to the reaction solution, followed by extraction with ethyl acetate. The resulting solution was dried over anhydrous magnesium sulfate, and filtered, after which the filtrate was concentrated and purified by column chromatography to obtain the title compound.

$^1$H NMR (400 MHz, $CDCl_3$): δ 8.24 (s, 1H), 8.19 (s, 1H), 7.38 (d, J=7.4 Hz, 1H), 7.34 (d, J=7.5 Hz, 1H), 7.27-7.22 (m, 1H), 6.12 (d, J=1.8 Hz, 1H), 6.04 (s, 1H), 5.76 (s, 1H), 3.78 (s, 3H), 3.44 (s, 1H), 2.83 (d, J=4.6 Hz, 3H), 2.22-2.11 (m, 5H), 1.92-1.69 (m, 8H), 1.60-1.40 (m, 3H)

<Example 2> Preparation of 2-((2-((4-(adamantan-2-ylamino)-2-methoxyphenyl)amino)-5-(trifluoromethyl)pyrimidin-4-yl)amino)-N,3-dimethylbenzamide (compound 2)

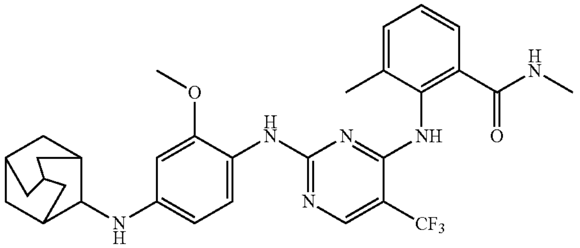 [SMILES: CNC(=O)c1cccc(C)c1Nc1nc(Nc2ccc(NC3C4CC5CC(C4)CC3C5)cc2OC)ncc1C(F)(F)F]

[Step 1] Preparation of N-(3-methoxy-4-nitrophenyl) adamantan-2-amine

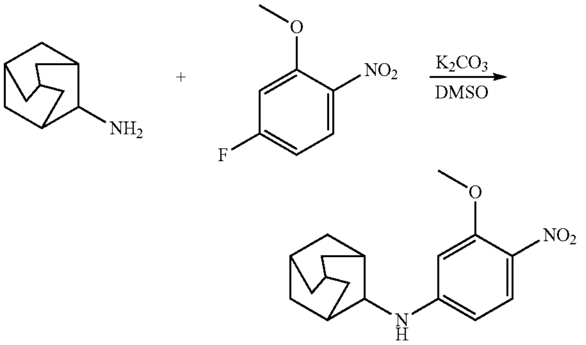

The title compound was synthesized in the same manner as in Example 1 by using adamantan-2-amine instead of trans-4-aminoadamantan-1-ol in step 1 of Example 1.

[Step 2] Preparation of N-(adamantan-2-yl)-3-methoxybenzen-1,4-diamine

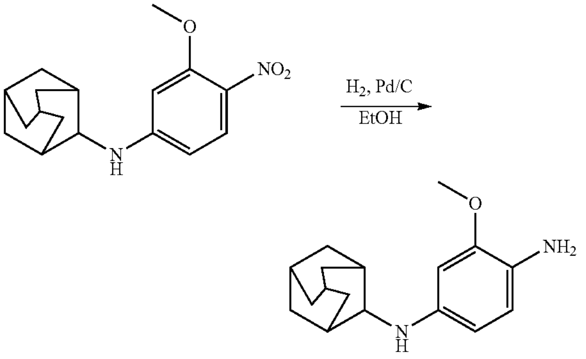

The title compound was synthesized in the same manner as in Example 1 by using N-(3-methoxy-4-nitrophenyl) adamantan-2-amine instead of (trans)-4-((3-methoxy-4-nitrophenyl)amino) adamantan-1-ol in step 2 of Example 1.

[Step 3] Preparation of N-(adamantan-2-yl)-N-(4-chloro-5-(trifluoromethyl)pyrimidin-2-yl)-2-methoxybenzen-1,4-diamine

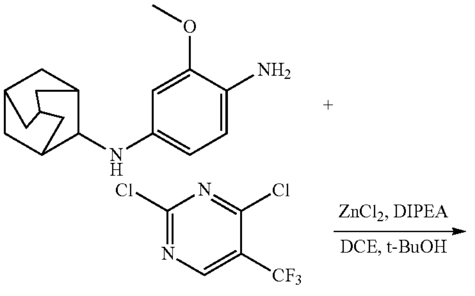

-continued

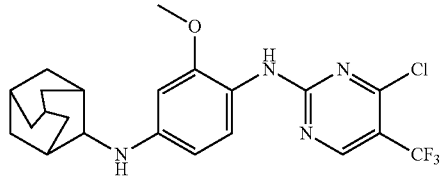

The title compound was synthesized in the same manner as in Example 1 by using N-(adamantan-2-yl)-3-methoxybenzen-1,4-diamine instead of (trans)-4-((4-amino-3-methoxyphenyl)amino) adamantan-1-ol in step 3 of Example 1.

[Step 4] Preparation of 2-((2-((4-(adamantan-2-yl) amino)-2-methoxyphenyl)amino)-5-(trifluoromethyl) pyrimidin-4-yl)amino)-N,3-dimethylbenzamide

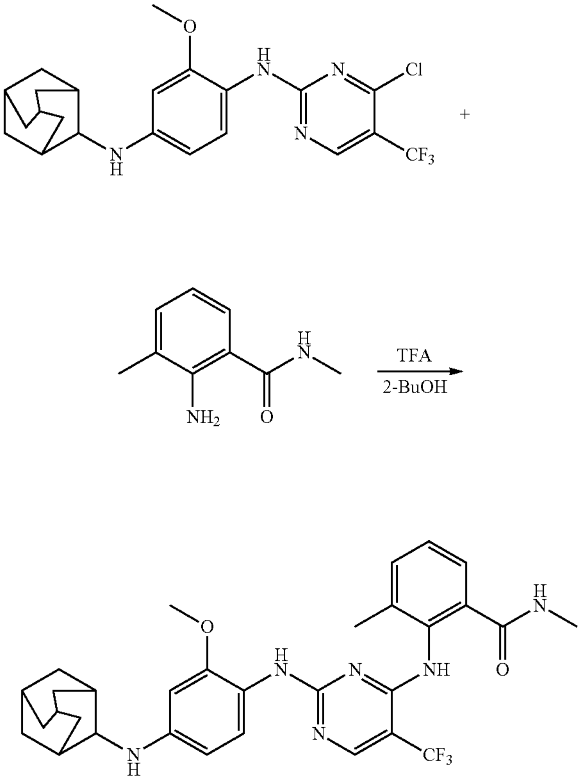

The title compound was synthesized in the same manner as in Example 1 by using N-(adamantan-2-yl)-N-(4-chloro-5-(trifluoromethyl)pyrimidin-2-yl)-2-methoxybenzene-1,4-diamine instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, DMSO-$d_6$): δ 9.10 (s, 1H), 8.30-8.25 (m, 1H), 8.20 (s, 1H), 7.91 (s, 1H), 7.39 (d, J=7.7 Hz, 1H), 7.34 (d, J=6.9 Hz, 1H), 7.25-7.20 (m, 1H), 7.01 (br s, 1H), 6.32 (s, 1H), 5.40 (br s, 1H), 3.63 (s, 3H), 3.43-3.38 (m, 1H), 2.69 (d, J=4.5 Hz, 3H), 2.15-2.00 (m, 5H), 1.94-1.69 (m, 9H), 1.51-1.45 (m, 2H)

<Example 3> Preparation of 2-((2-((4-(4-(adamantan-2-yl)piperazin-1-yl)-2-methoxyphenyl)amino)-5-(trifluoromethyl)pyrimidin-4-yl)amino)-N,3-dimethylbenzamide (compound 3)

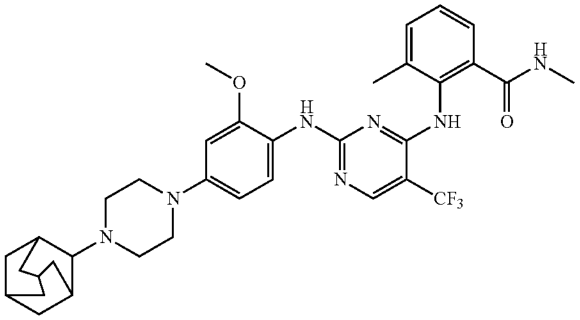 [SMILES: CNC(=O)c1cccc(C)c1Nc1nc(Nc2ccc(N3CCN(C4C5CC6CC(C5)CC4C6)CC3)cc2OC)ncc1C(F)(F)F]

[Step 1] Preparation of 1-(3-methoxy-4-nitrophenyl)piperazine

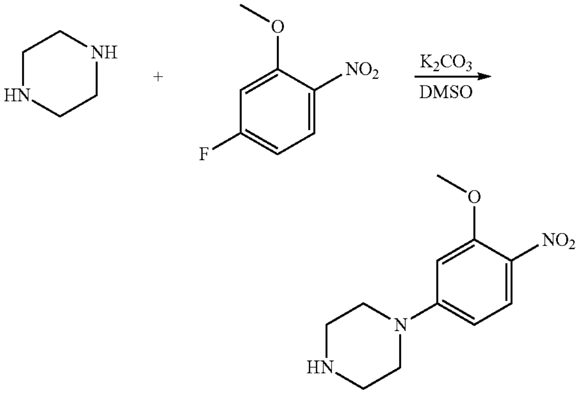

The title compound was synthesized in the same manner as in Example 1 by using piperazine instead of trans-4-aminoadamantan-1-ol in step 1 of Example 1.

[Step 2] Preparation of 1-(adamantan-2-yl)-4-(3-methoxy-4-nitrophenyl)piperazine

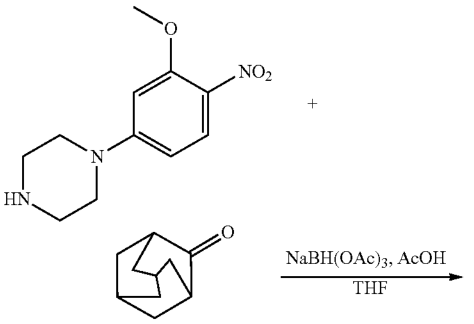

-continued

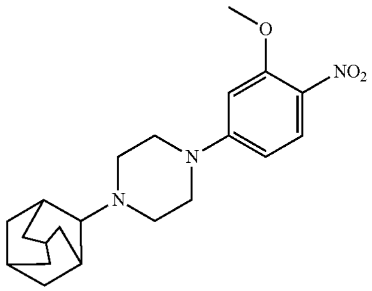

1-(3-Methoxy-4-nitrophenyl)piperazine prepared in above step 1, adamantan-2-one, triacetoxysodium borohydride, tetrahydrofuran, and acetic acid were stirred at room temperature for 15 hours. Ice water was poured into the reaction solution, extracted with ethyl acetate, dried over anhydrous magnesium sulfate, and filtered, after which the filtrate was concentrated and purified by column chromatography to obtain the title compound.

[Step 3] Preparation of 4-(4-(adamantan-2-yl)piperazin-1-yl)-2-methoxyaniline

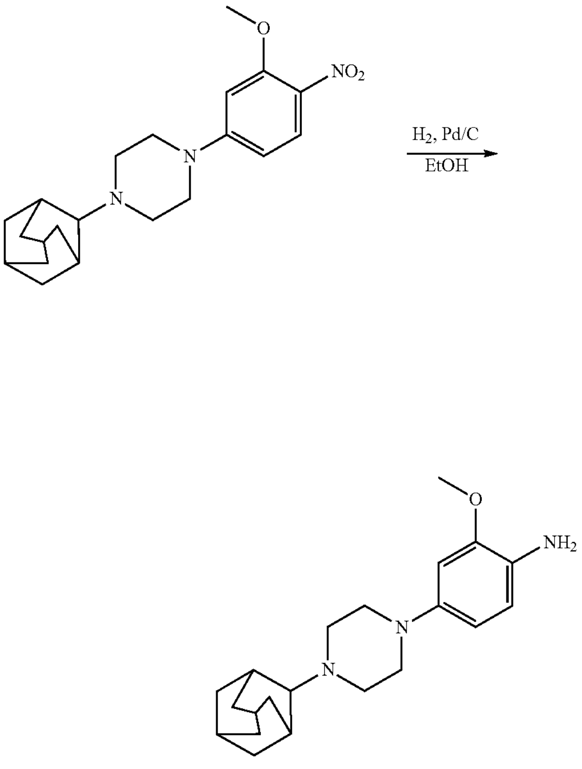

The title compound was synthesized in the same manner as in Example 1 by using 1-(adamantan-2-yl)-4-(3-methoxy-4-nitrophenyl)piperazine instead of (trans)-4-((3-methoxy-4-nitrophenyl)amino) adamantan-1-ol in step 2 of Example 1. [Step 4] Preparation of N-(4-(4-(adamantan-2-yl)piperazin-1-yl)-2-methoxyphenyl-4-chloro-5-(trifluoromethyl) pyrimidin-2-amine

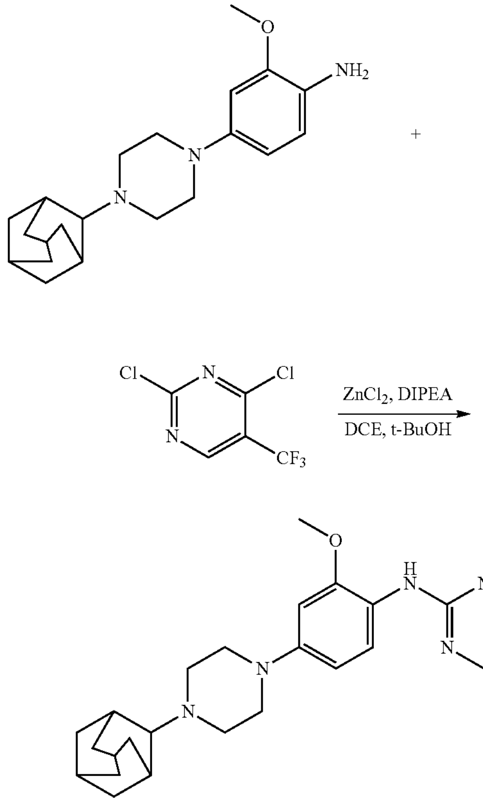

The title compound was synthesized in the same manner as in Example 1 by using 4-(4-(adamantan-2-yl)piperazin-1-yl)-2-methoxyaniline instead of (trans)-4-((4-amino-3-methoxyphenyl)amino) adamantan-1-ol in step 3 of Example 1.

[Step 5] Preparation of 2-((2-((4-(4-(adamantan-2-yl)piperazin-1-yl)-2-methoxyphenyl)amino)-5-(trifluoromethyl)pyrimidin-4-yl)amino)-N,3-dimethylbenzamide

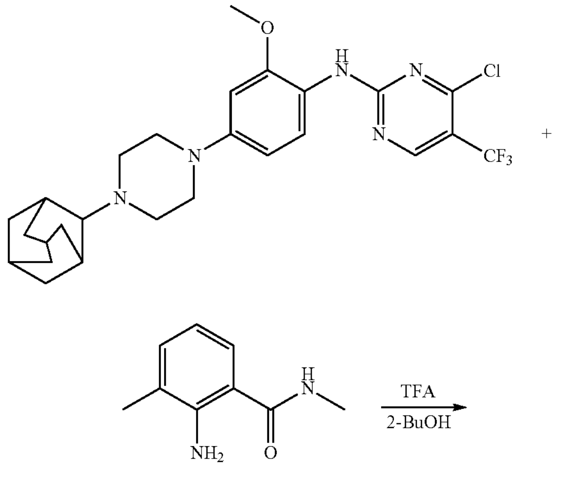

-continued

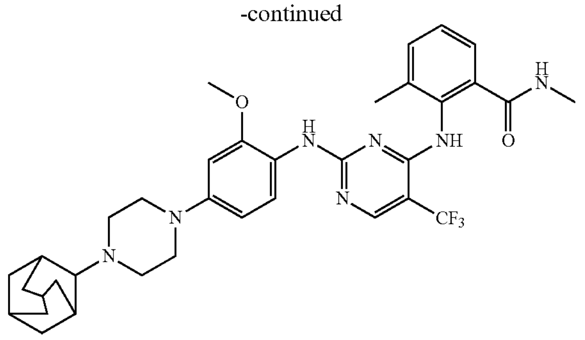

The title compound was synthesized in the same manner as in Example 1 by using N-(4-(4-(adamantan-2-yl)piperazin-1-yl)-2-methoxyphenyl-4-chloro-5-(trifluoromethyl)pyrimidin-2-amine instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.26 (s, 2H, overlapped), 7.41 (d, J=7.3 Hz, 1H), 7.34 (d, J=7.5 Hz, 1H), 7.31-7.26 (m, 1H), 6.47 (d, J=2.0 Hz, 1H), 6.09 (br s, 1H), 6.00 (s, 1H), 3.82 (s, 3H), 3.09 (m, 4H), 2.84 (d, J=4.8 Hz, 3H), 2.61 (m, 4H), 2.21 (s, 3H), 2.19-2.10 (m, 2H), 1.96-1.82 (m, 4H), 1.76-1.65 (m, 5H), 1.54-1.39 (m, 2H)

<Example 4> Preparation of 2-((2-((4-(4-((trans)-5-hydroxyadamantan-2-yl)piperazin-1-yl)-2-methoxyphenyl)amino)-5-(trifluoromethyl)pyrimidin-4-yl)amino)-N,3-dimethylbenzamide (compound 4)

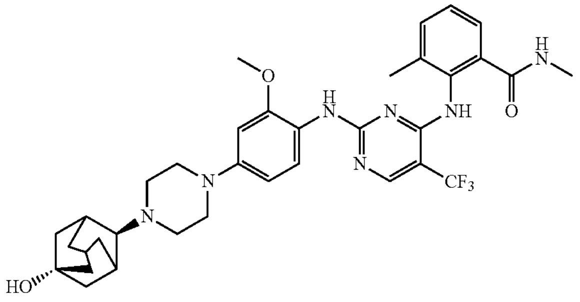 [SMILES: CNC(=O)c1cccc(C)c1Nc1nc(Nc2ccc(N3CCN([C@H]4C5CC6CC4C[C@](O)(C6)C5)CC3)cc2OC)ncc1C(F)(F)F]

[Step 1] Preparation of (trans)-4-(4-(3-methoxy-4-nitrophenyl)piperazin-1-yl) adamantan-1-ol

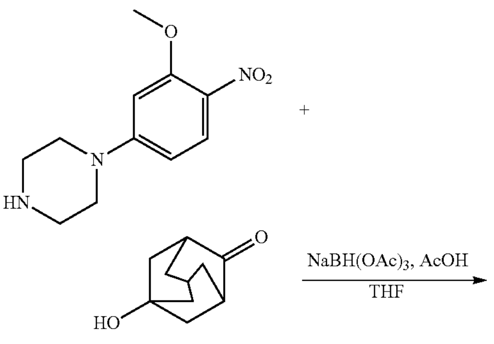

-continued

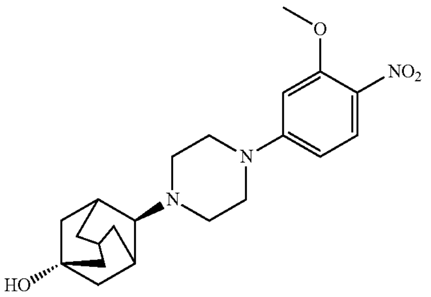

The title compound was synthesized in the same manner as in Example 3 by using 5-hydroxyadamantan-2-one instead of adamantan-2-one in step 2 of Example 3. [Step 2] Preparation of (trans)-4-(4-(4-amino-3-methoxyphenyl)piperazin-1-yl) adamantan-1-ol

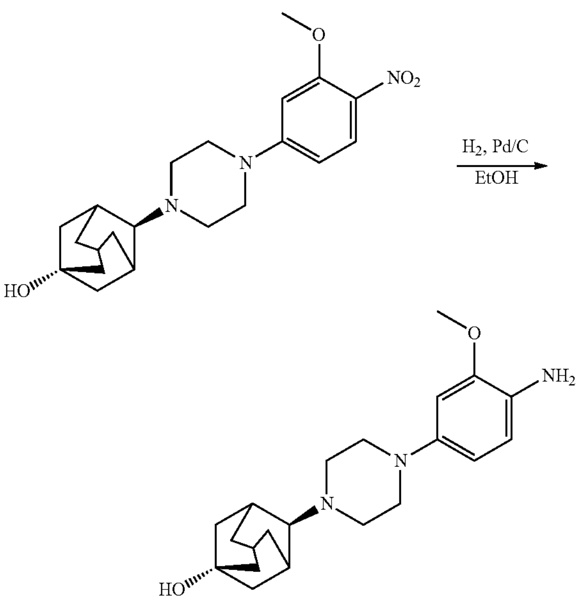

The title compound was synthesized in the same manner as in Example 1 by using (trans)-4-(4-(3-methoxy-4-nitrophenyl)piperazin-1-yl) adamantan-1-ol instead of (trans)-4-((3-methoxy-4-nitrophenyl)amino) adamantan-1-ol in step 2 of Example 1. [Step 3] Preparation of (trans)-4-(4-(4-((4-chloro-5-(trifluoromethyl)pyrimidin-2-yl)amino)-3-methoxyphenyl)piperazin-1-yl) adamantan-1-ol

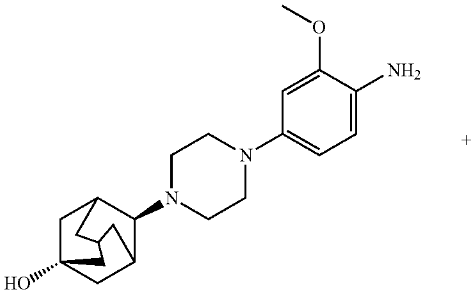

-continued

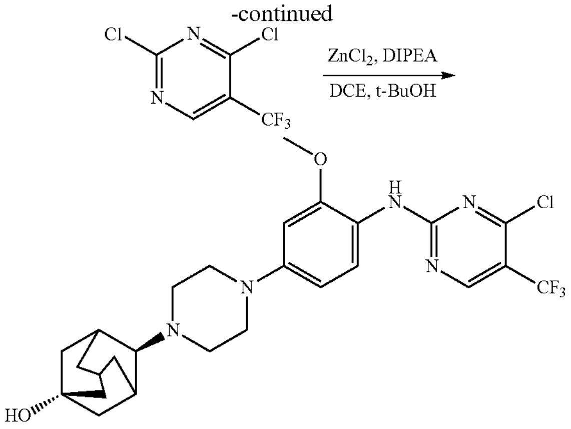

The title compound was synthesized in the same manner as in Example 1 by using (trans)-4-(4-(4-amino-3-methoxyphenyl)piperazin-1-yl) adamantan-1-ol instead of (trans)-4-((4-amino-3-methoxyphenyl)amino) adamantan-1-ol in step 3 of Example 1.

[Step 4] Preparation of 2-((2-((4-(4-((trans)-5-hydroxyadamantan-2-yl)piperazin-1-yl)-2-methoxyphenyl)amino)-5-(trifluoromethyl)pyrimidin-4-yl) amino)-N,3-dimethylbenzamide

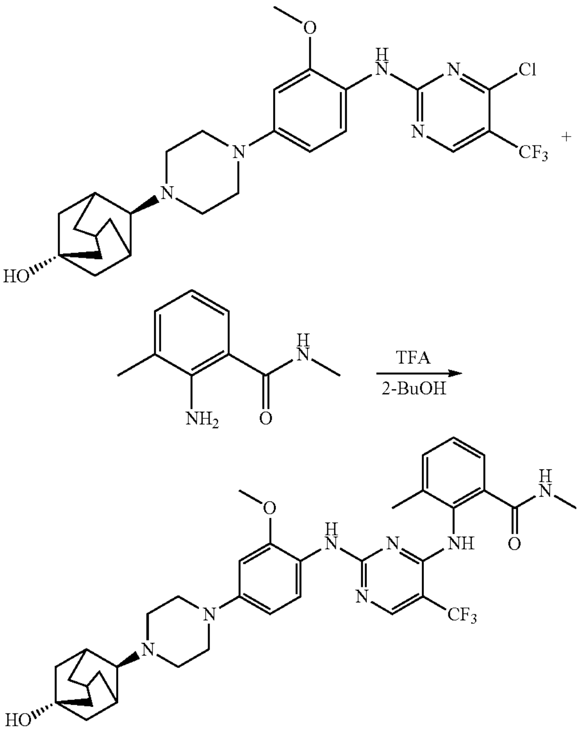

The title compound was synthesized in the same manner as in Example 1 by using (trans)-4-(4-(4-((4-chloro-5-(trifluoromethyl)pyrimidin-2-yl)amino)-3-methoxyphenyl)piperazin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.26 (s, 2H, overlapped), 7.41 (d, J=7.3 Hz, 1H), 7.34 (d, J=7.5 Hz, 1H), 7.31-7.26 (m, 1H), 6.47 (d, J=2.0 Hz, 1H), 6.09 (br s, 1H), 6.00 (s, 1H), 3.82 (s, 3H), 3.09 (m, 4H), 2.84 (d, J=4.8 Hz, 3H), 2.61 (m, 4H), 2.32-2.26 (m, 1H), 2.21 (s, 3H), 2.14-1.98 (m, 4H), 1.81-1.59 (m, 6H), 1.42-1.24 (m, 3H)

<Example 5> Preparation of 2-((2-((4-(4-((cis)-5-hydroxyadamantan-2-yl)piperazin-1-yl)-2-methoxyphenyl)amino)-5-(trifluoromethyl)pyrimidin-4-yl)amino)-N,3-dimethylbenzamide (compound 5)

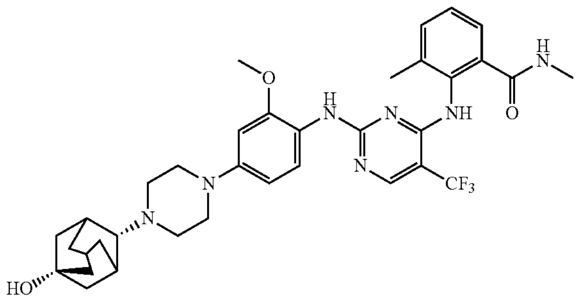 [SMILES: CNC(=O)c1cccc(C)c1Nc1nc(Nc2ccc(N3CCN([C@H]4C5CC6CC4C[C@@](O)(C6)C5)CC3)cc2OC)ncc1C(F)(F)F]

[Step 1] Preparation of (cis)-4-(4-(3-methoxy-4-nitrophenyl)piperazin-1-yl) adamantan-1-ol

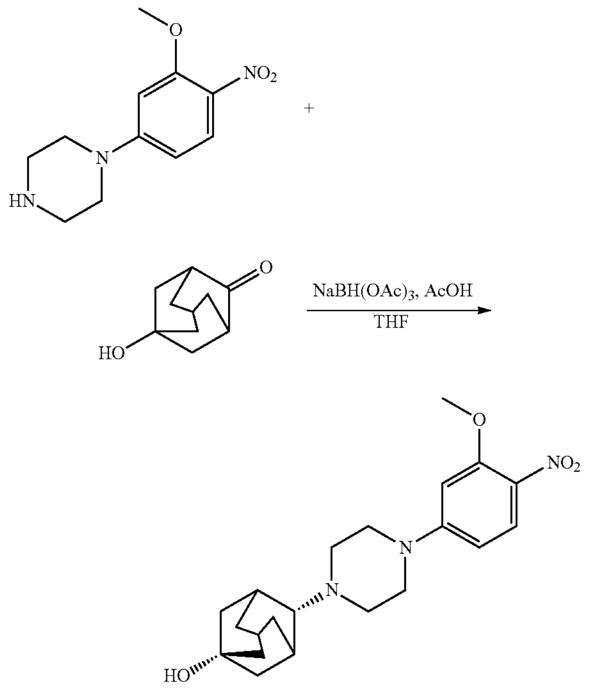

The title compound was synthesized in the same manner as in Example 3 by using 5-hydroxyadamantan-2-one instead of adamantan-2-one in step 2 of Example 3.

[Step 2] Preparation of (cis)-4-(4-(4-amino-3-methoxyphenyl)piperazin-1-yl) adamantan-1-ol

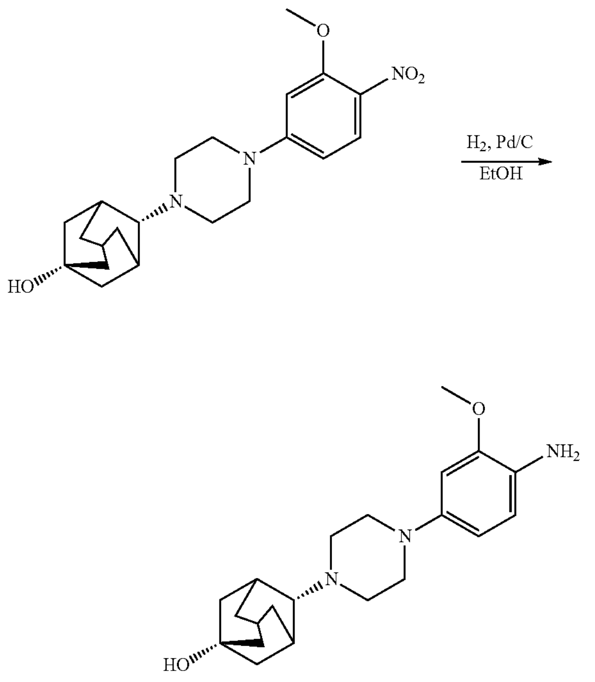

The title compound was synthesized in the same manner as in Example 1 by using (cis)-4-(4-(3-methoxy-4-nitrophenyl)piperazin-1-yl) adamantan-1-ol instead of (trans)-4-((3-methoxy-4-nitrophenyl)amino) adamantan-1-ol in step 2 of Example 1.

[Step 3] Preparation of (cis)-4-(4-(4-((4-chloro-5-(trifluoromethyl)pyrimidin-2-yl)amino)-3-methoxyphenyl)piperazin-1-yl) adamantan-1-ol

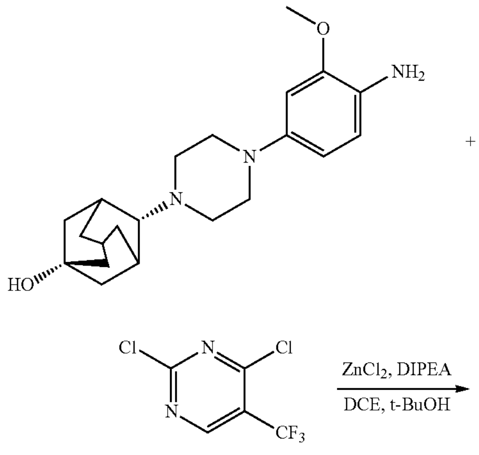

-continued

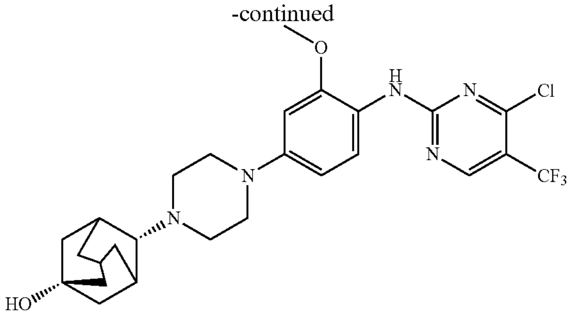

The title compound was synthesized in the same manner as in Example 1 by using (cis)-4-(4-(4-amino-3-methoxyphenyl)piperazin-1-yl) adamantan-1-ol instead of (trans)-4-((4-amino-3-methoxyphenyl)amino) adamantan-1-ol in step 3 of Example 1.

[Step 4] Preparation of 2-((2-((4-(4-((cis)-5-hydroxyadamantan-2-yl)piperazin-1-yl)-2-methoxyphenyl)amino)-5-(trifluoromethyl)pyrimidin-4-yl) amino)-N,3-dimethylbenzamide

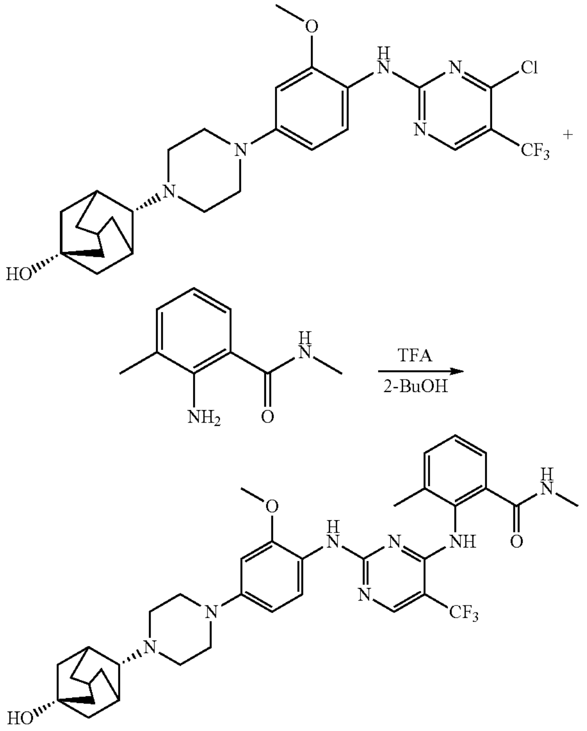

The title compound was synthesized in the same manner as in Example 1 by using (cis)-4-(4-(4-((4-chloro-5-(trifluoromethyl)pyrimidin-2-yl)amino)-3-methoxyphenyl)piperazin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.26 (s, 2H, overlapped), 7.41 (d, J=7.3 Hz, 1H), 7.34 (d, J=7.5 Hz, 1H), 7.31-7.26 (m, 1H), 6.47 (d, J=2.0 Hz, 1H), 6.09 (br s, 1H), 6.00 (s, 1H), 3.82 (s, 3H), 3.09 (m, 4H), 2.84 (d, J=4.8 Hz, 3H), 2.61 (m, 4H), 2.33-2.25 (m, 1H), 2.21 (s, 3H), 2.13-1.97 (m, 4H), 1.82-1.60 (m, 5H), 1.41-1.23 (m, 3H)

<Example 6> Preparation of 2-((2-((4-((1-(adamantan-2-yl)piperidin-4-yl)amino)-2-methoxyphenyl) amino)-5-(trifluoromethyl)pyrimidin-4-yl)amino)-N, 3-dimethylbenzamide (compound 6)

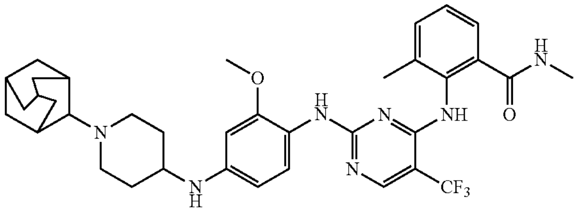 [SMILES: CNC(=O)c1cccc(C)c1Nc1nc(Nc2ccc(NC3CCN(C4C5CC6CC(C5)CC4C6)CC3)cc2OC)ncc1C(F)(F)F]

[Step 1] Preparation of 4-((3-methoxy-4-nitrophenyl)amino)piperidin-1-carboxylic acid tert-butyl

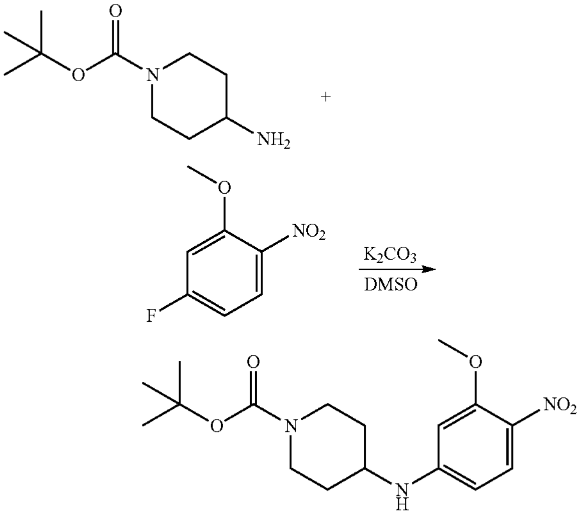

The title compound was synthesized in the same manner as in Example 1 by using 4-aminopiperidin-1-carboxylic acid tert-butyl instead of trans-4-aminoadamantan-1-ol in step 1 of Example 1.

[Step 2] Preparation of N-(3-methoxy-4-nitrophenyl)piperidin-4-amine

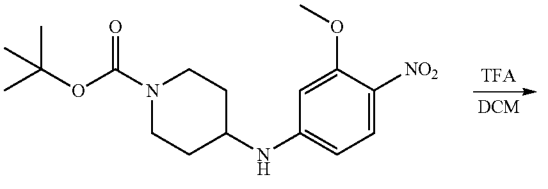

-continued

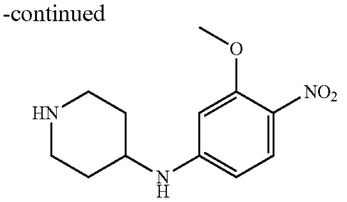

4-((3-Methoxy-4-nitrophenyl)amino)piperidin-1-carboxylic acid tert-butyl prepared in above step 1 was dissolved in dichloromethane, after which trifluoroacetic acid was added and stirred at room temperature for three hours. After completion of the reaction, distilled water was added to the reaction solution, followed by extraction with dichloromethane. The resulting solution was dried over anhydrous magnesium sulfate, and filtered, after which the filtrate was concentrated and purified by column chromatography to obtain the title compound.

[Step 3] Preparation of 1-(adamantan-2-yl)-N-(3-methoxy-4-nitrophenyl)piperidin-4-amine

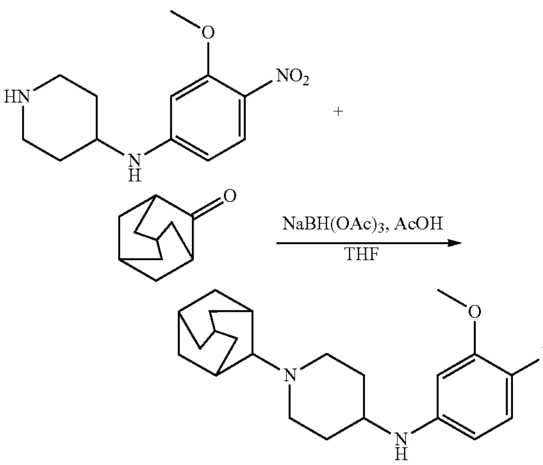

The title compound was synthesized in the same manner as in Example 3 by using N-(3-methoxy-4-nitrophenyl) piperidin-4-amine instead of 1-(3-methoxy-4-nitrophenyl) piperazine in step 2 of Example 3.

[Step 4] Preparation of N-(1-(adamantan-2-yl)piperidin-4-yl)-3-methoxybenzen-1,4-diamine

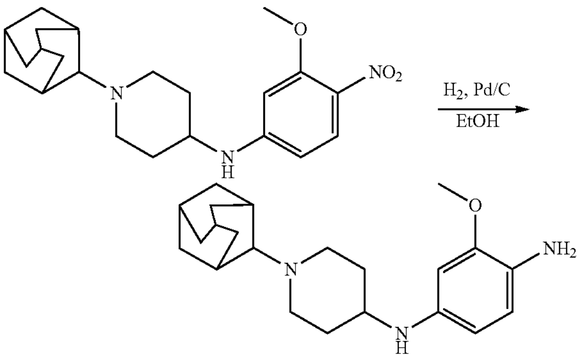

The title compound was synthesized in the same manner as in Example 1 by using 1-(adamantan-2-yl)-N-(3-methoxy-4-nitrophenyl)piperidin-4-amine instead of (trans)-4-((3-methoxy-4-nitrophenyl)amino) adamantan-1-ol in step 2 of Example 1.

[Step 5] Preparation of N-(1-(adamantan-2-yl)piperidin-4-yl)-N-(4-chloro-5-(trifluoromethyl)pyrimidin-2-yl)-2-methoxybenzen-1,4-diamine

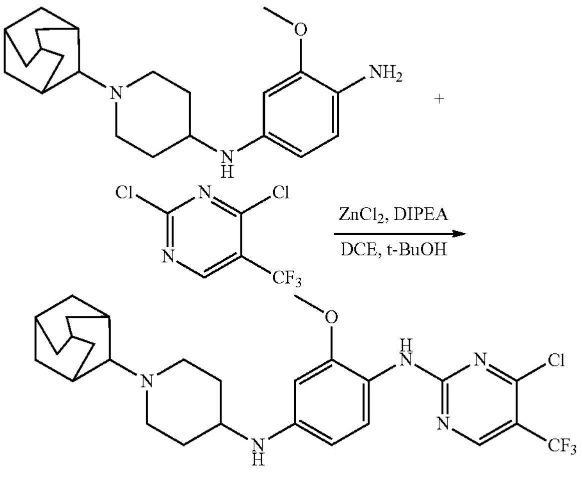

The title compound was synthesized in the same manner as in Example 1 by using N-(1-(adamantan-2-yl)piperidin-4-yl)-3-methoxybenzen-1,4-diamine instead of (trans)-4-((4-amino-3-methoxyphenyl)amino) adamantan-1-ol in step 3 of Example 1.

[Step 6] Preparation of 2-((2-((4-((1-(adamantan-2-yl)piperidin-4-yl)amino)-2-methoxyphenyl)amino)-5-(trifluoromethyl)pyrimidin-4-yl)amino)-N,3-dimethylbenzamide

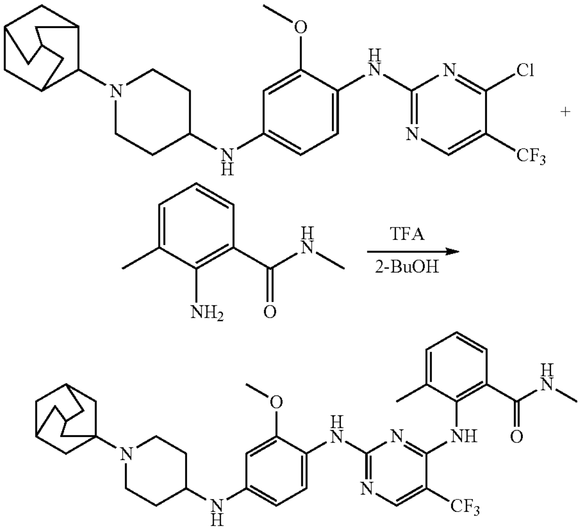

The title compound was synthesized in the same manner as in Example 1 by using N-(1-(adamantan-2-yl)piperidin- 4-yl)-N-(4-chloro-5-(trifluoromethyl)pyrimidin-2-yl)-2-methoxybenzen-1,4-diamine instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.25 (s, 1H), 8.13 (br s, 1H), 7.41-7.32 (m, 2H), 7.29-7.24 (m, 1H), 6.13 (d, J=2.3 Hz, 1H), 5.97 (br s, 1H), 3.78 (s, 3H), 3.06-2.95 (m, 2H), 2.84 (d, J=4.8 Hz, 3H), 2.21 (s, 3H), 2.12-1.92 (m, 8H), 1.90-1.75 (m, 5H), 1.74-1.62 (m, 5H), 1.47-1.35 (m, 4H)

<Example 7> Preparation of 2-((2-((4-((1-((trans)-5-hydroxyadamantan-2-yl)piperidin-4-yl)amino)-2-methoxyphenyl)amino)-5-(trifluoromethyl)pyrimidin-4-yl)amino)-N,3-dimethylbenzamide (compound 7)

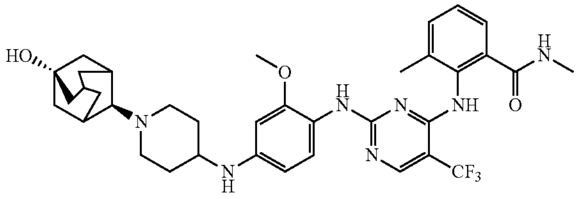 [SMILES: CNC(=O)c1cccc(C)c1Nc1nc(Nc2ccc(NC3CCN([C@H]4C5CC6CC4C[C@](O)(C6)C5)CC3)cc2OC)ncc1C(F)(F)F]

[Step 1] Preparation of (trans)-4-(4-((3-methoxy-4-nitrophenyl)amino)piperidin-1-yl) adamantan-1-ol

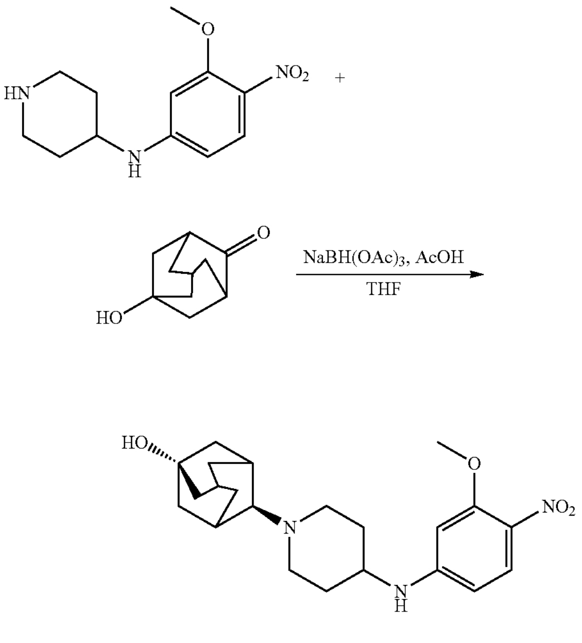

The title compound was synthesized in the same manner as in Example 6 by using 5-hydroxyadamantan-2-one instead of adamantan-2-one in step 3 of Example 6.

[Step 2] Preparation of (trans)-4-(4-((4-amino-3-methoxyphenyl)amino)piperidin-1-yl) adamantan-1-ol

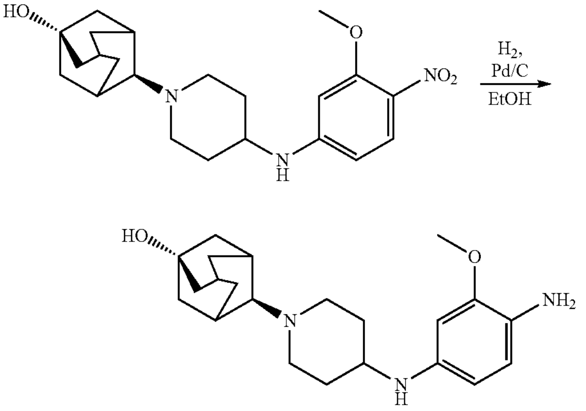 [SMILES: "EtOH" ; COc1cc(NC2CCN([C@H]3C4CC5CC3C[C@](O)(C5)C4)CC2)ccc1[N+](=O)[O-] ; "H2,Pd/C" ; COc1cc(NC2CCN([C@H]3C4CC5CC3C[C@](O)(C5)C4)CC2)ccc1N]

The title compound was synthesized in the same manner as in Example 1 by using (trans)-4-(4-((3-methoxy-4-nitrophenyl)amino)piperidin-1-yl) adamantan-1-ol instead of (trans)-4-((3-methoxy-4-nitrophenyl)amino) adamantan-1-ol in step 2 of Example 1.

[Step 3] Preparation of (trans)-4-(4-((4-((4-chloro-5-(trifluoromethyl)pyrimidin-2-yl)amino)-3-methoxyphenyl)amino)piperidin-1-yl) adamantan-1-ol

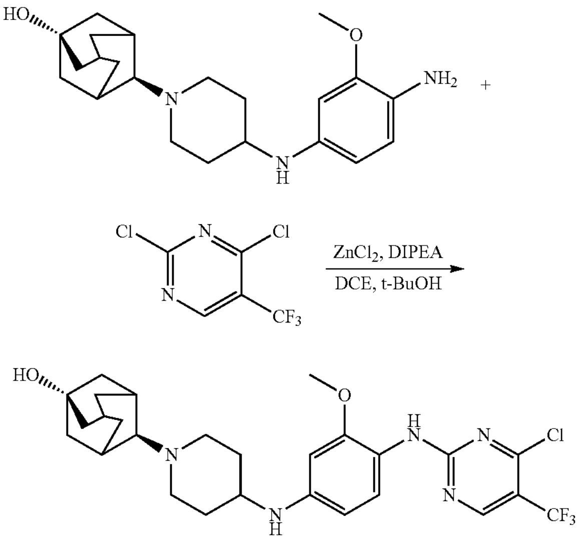

The title compound was synthesized in the same manner as in Example 1 by using (trans)-4-(4-((4-amino-3-methoxyphenyl)amino)piperidin-1-yl) adamantan-1-ol instead of (trans)-4-((4-amino-3-methoxyphenyl)amino) adamantan-1-ol in step 3 of Example 1.

[Step 4] Preparation of 2-((2-((4-((1-((trans)-5-hydroxyadamantan-2-yl)piperidin-4-yl)amino)-2-methoxyphenyl)amino)-5-(trifluoromethyl)pyrimidin-4-yl)amino)-N,3-dimethylbenzamide

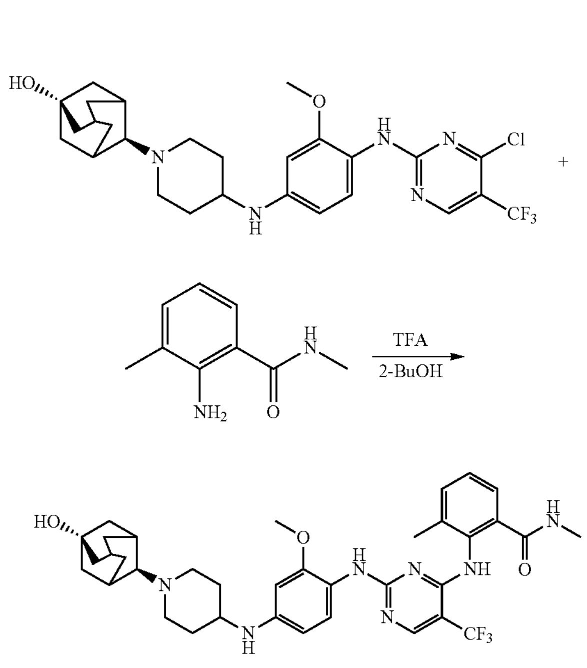

The title compound was synthesized in the same manner as in Example 1 by using (trans)-4-(4-((4-((4-chloro-5-(trifluoromethyl)pyrimidin-2-yl)amino)-3-methoxyphenyl)amino)piperidin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1H$ NMR (400 MHz, $CDCl_3$): δ 8.25 (s, 1H), 8.15 (s, 1H), 7.41-7.32 (m, 2H), 7.31-7.24 (m, 2H), 6.13 (d, J=2.3 Hz, 1H), 5.97 (s, 1H), 5.76 (s, 1H), 3.78 (s, 3H), 3.25-3.14 (m, 1H), 3.05-2.91 (m, 2H), 2.84 (d, J=4.8 Hz, 3H), 2.39-2.31 (m, 2H), 2.21 (s, 3H), 2.15-1.95 (m, 7H), 1.77-1.66 (m, 5H), 1.56 (m, 2H), 1.40 (m, 4H).

<Example 8> Preparation of 2-((2-((4-((1-((cis)-5-hydroxyadamantan-2-yl)piperidin-4-yl)amino)-2-methoxyphenyl)amino)-5-(trifluoromethyl)pyrimidin-4-yl)amino)-N,3-dimethylbenzamide (compound 8)

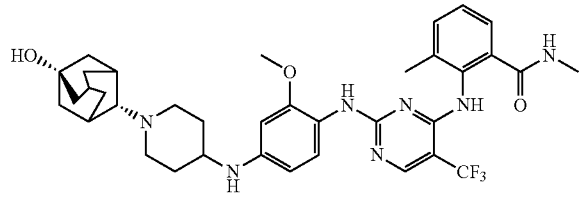 [SMILES: CNC(=O)c1cccc(C)c1Nc1nc(Nc2ccc(NC3CCN([C@H]4C5CC6CC4C[C@@](O)(C6)C5)CC3)cc2OC)ncc1C(F)(F)F]

[Step 1] Preparation of (cis)-4-(4-((3-methoxy-4-nitrophenyl)amino)piperidin-1-yl) adamantan-1-ol

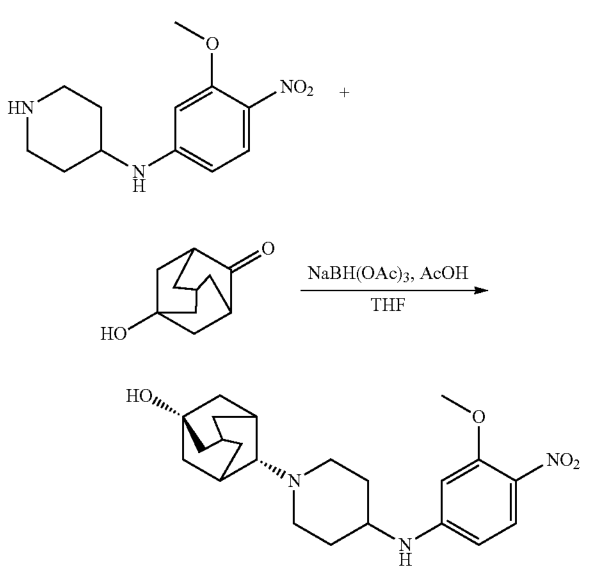

The title compound was synthesized in the same manner as in Example 6 by using 5-hydroxyadamantan-2-one instead of adamantan-2-one in step 3 of Example 6.

[Step 2] Preparation of (cis)-4-(4-((4-amino-4-methoxyphenyl)amino)piperidin-1-yl) adamantan-1-ol

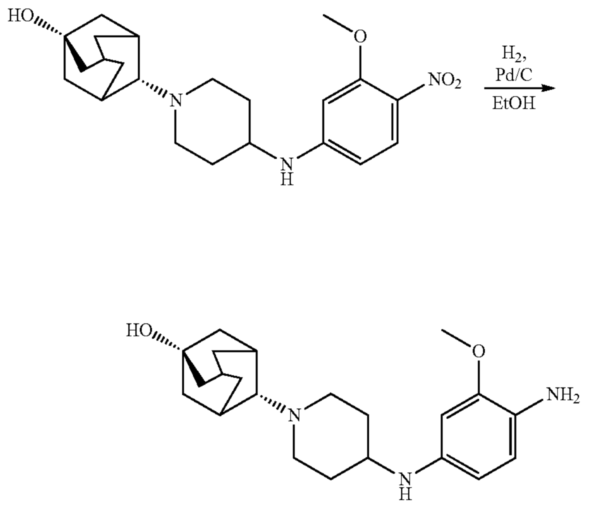

The title compound was synthesized in the same manner as in Example 1 by using (cis)-4-(4-((3-methoxy-4-nitrophenyl)amino)piperidin-1-yl) adamantan-1-ol instead of (trans)-4-((3-methoxy-4-nitrophenyl)amino) adamantan-1-ol in step 2 of Example 1.

[Step 3] Preparation of (cis)-4-(4-((4-((4-chloro-5-(trifluoromethyl)pyrimidin-2-yl)amino)-3-methoxyphenyl)amino)piperidin-1-yl) adamantan-1-ol

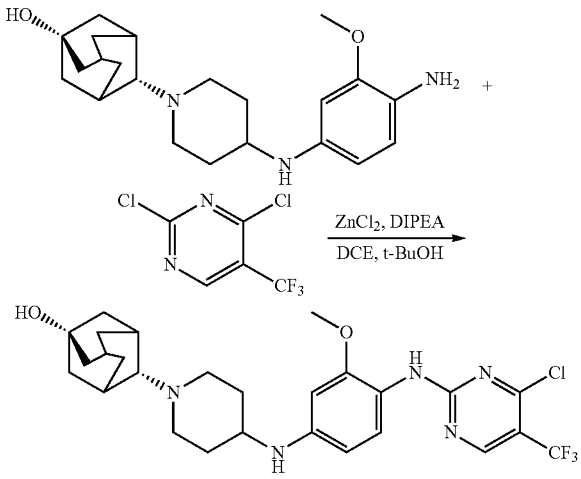

The title compound was synthesized in the same manner as in Example 1 by using (cis)-4-(4-((4-amino-3-methoxyphenyl)amino)piperidin-1-yl) adamantan-1-ol instead of (trans)-4-((4-amino-3-methoxyphenyl)amino) adamantan-1-ol in step 3 of Example 1.

[Step 4] Preparation of 2-((2-((4-((1-((cis)-5-hydroxyadamantan-2-yl)piperidin-4-yl)amino)-2-methoxyphenyl)amino)-5-(trifluoromethyl)pyrimidin-4-yl)amino)-N,3-dimethylbenzamide

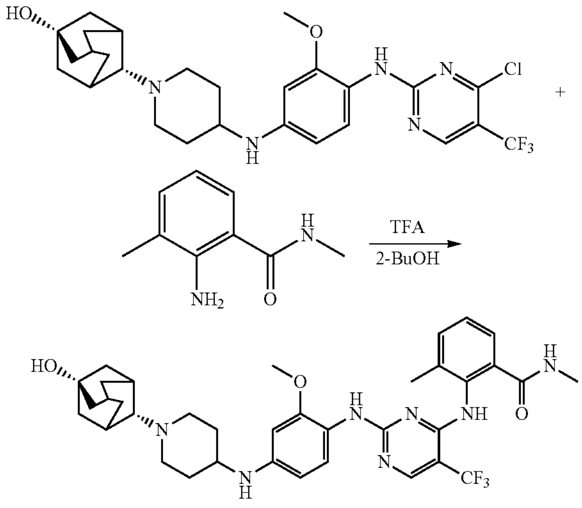

The title compound was synthesized in the same manner as in Example 1 by using (cis)-4-(4-((4-((4-chloro-5-(trifluoromethyl)pyrimidin-2-yl)amino)-3-methoxyphenyl) amino)piperidin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.25 (s, 1H), 8.15 (s, 1H), 7.41-7.32 (m, 2H), 7.31-7.24 (m, 2H), 6.13 (d, J=2.3 Hz, 1H), 5.97 (s, 1H), 5.76 (s, 1H), 3.78 (s, 3H), 3.25-3.14 (m, 1H), 3.05-2.91 (m, 2H), 2.84 (d, J=4.8 Hz, 3H), 2.39-2.31 (m, 2H), 2.21 (s, 3H), 2.15-1.95 (m, 7H), 1.77-1.66 (m, 5H), 1.56 (m, 2H), 1.40 (m, 4H).

<Example 9> Preparation of 2-((2-((4-((1-(adamantan-2-yl)piperidin-4-yl)oxy)-2-methoxyphenyl) amino)-5-(trifluoromethyl)pyrimidin-4-yl)amino)-N, 3-dimethylbenzamide (compound 9)

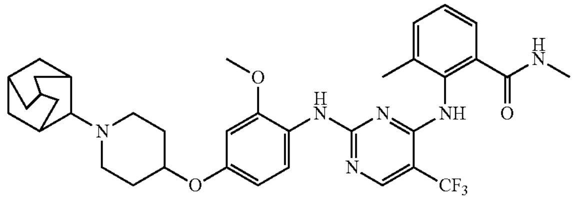 [SMILES: CNC(=O)c1cccc(C)c1Nc1nc(Nc2ccc(OC3CCN(C4C5CC6CC(C5)CC4C6)CC3)cc2OC)ncc1C(F)(F)F]

[Step 1] Preparation of 4-((3-methoxy-4-nitrophenyl)oxy)piperidin-1-carboxylic acid tert-butyl

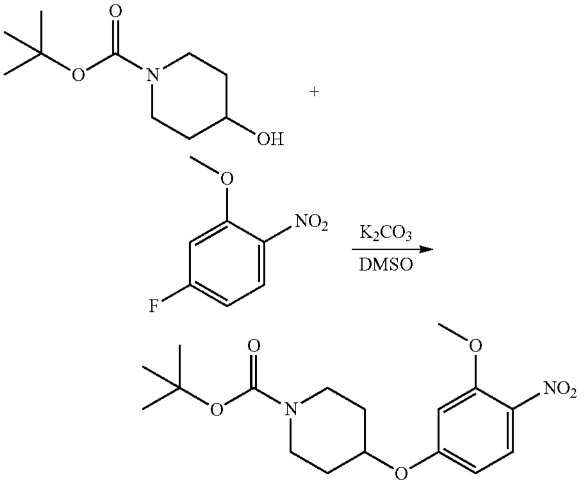

The title compound was synthesized in the same manner as in Example 1 by using 4-hydroxypiperidin-1-carboxylic acid tert-butyl instead of trans-4-aminoadamantan-1-ol in step 1 of Example 1.

[Step 2] Preparation of 4-(3-methoxy-4-nitrophenoxy)piperidine

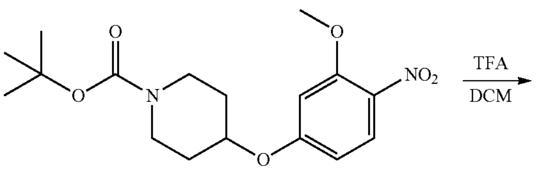

-continued

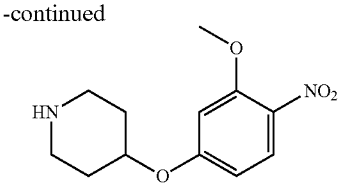

The title compound was synthesized in the same manner as in Example 6 by using 4-((3-methoxy-4-nitrophenyl)oxy) piperidin-1-carboxylic acid tert-butyl instead of 4-((3-methoxy-4-nitrophenyl)amino)piperidin-1-carboxylic acid tert-butyl in step 2 of Example 6.

[Step 3] Preparation of 1-(adamantan-2-yl)-4-(3-methoxy-4-nitrophenoxy)piperidine

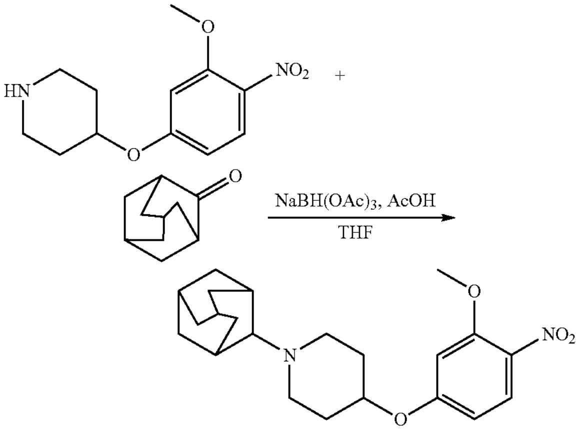

The title compound was synthesized in the same manner as in Example 3 by using 4-(3-methoxy-4-nitrophenoxy) piperidine instead of 1-(3-methoxy-4-nitrophenyl)piperazine in step 2 of Example 3.

[Step 4] Preparation of 4-((1-(adamantan-2-yl)piperidin-4-yl)oxy)-2-methoxyaniline

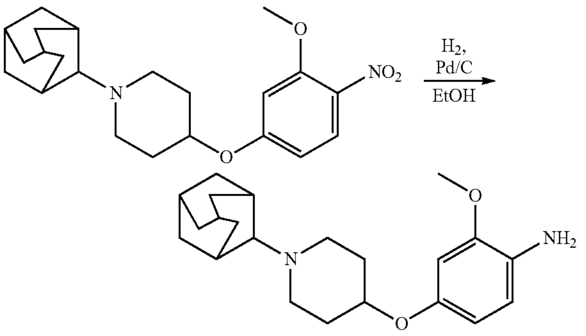

The title compound was synthesized in the same manner as in Example 1 by using 1-(adamantan-2-yl)-4-(3-methoxy-4-nitrophenoxy)piperidine instead of (trans)-4-((3-methoxy-4-nitrophenyl)amino) adamantan-1-ol in step 2 of Example 1.

[Step 5] Preparation of N-(4-((1-(adamantan-2-yl) piperidin-4-yl)oxy)-2-methoxyphenyl)-4-chloro-5-(trifluoromethyl)pyrimidin-2-amine

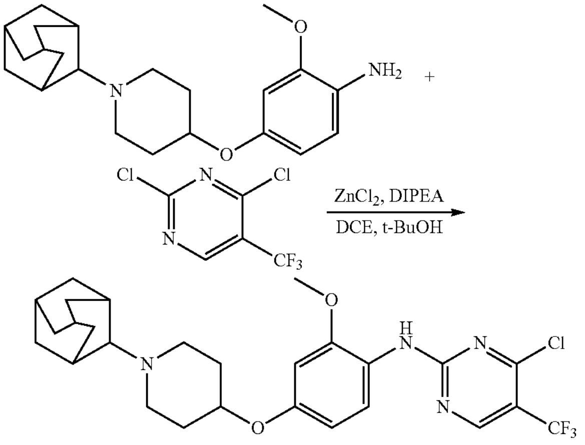

The title compound was synthesized in the same manner as in Example 1 by using 4-((1-(adamantan-2-yl)piperidin-4-yl)oxy)-2-methoxyaniline instead of (trans)-4-((4-amino-3-methoxyphenyl)amino) adamantan-1-ol in step 3 of Example 1.

[Step 6] Preparation of 2-((2-((4-((1-(adamantan-2-yl)piperidin-4-yl)oxy)-2-methoxyphenyl)amino)-5-(trifluoromethyl)pyrimidin-4-yl)amino)-N,3-dimethylbenzamide

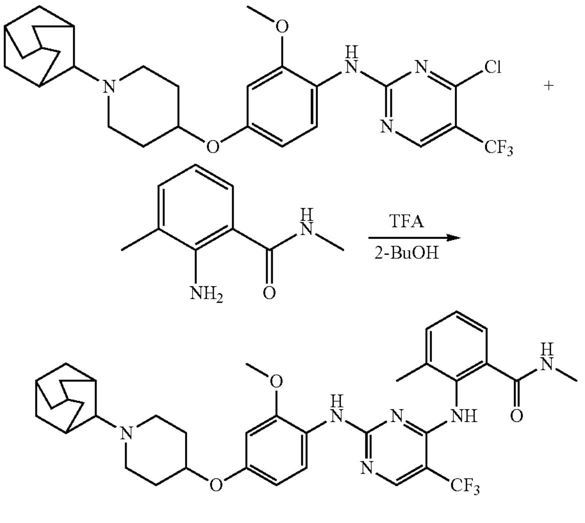

The title compound was synthesized in the same manner as in Example 1 by using N-(4-((1-(adamantan-2-yl)piperidin-4-yl)oxy)-2-methoxyphenyl)-4-chloro-5-(trifluoromethyl)pyrimidin-2-amine instead of (trans)-4-((4-((4-chloro-5-(trifluoromethyl)pyrimidin-2-yl)amino)-3-methoxyphenyl)amino) adamantan-1-ol in step 4 of Example 1.

$^{1}$H NMR (400 MHz, $CDCl_3$): δ 8.31 (br s, 1H), 8.27 (s, 1H), 7.42-7.34 (m, 2H), 7.28 (t, J=7.5 Hz, 1H), 6.44 (d,

J=1.9 Hz, 1H), 6.08 (br s, 1H), 5.98 (s, 1H), 4.16 (br s, 1H), 3.81 (s, 3H), 2.92-2.81 (m, 4H), 2.20 (s, 3H), 2.18-1.92 (m, 8H), 1.92-1.75 (m, 5H), 1.75-1.57 (m, 6H), 1.49-1.33 (m, 3H).

<Example 10> Preparation of 2-((2-((2-methoxy-4-((4-oxoadamantan-1-yl)oxy)phenyl)amino)-5-(trifluoromethyl)pyrimidin-4-yl)amino)-N,3-dimethylbenzamide (compound to)

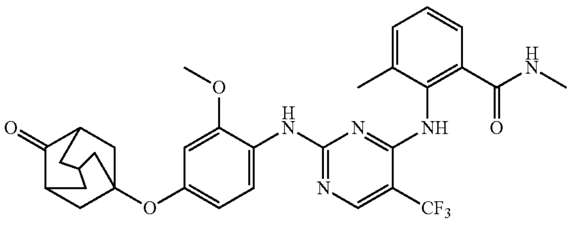 [SMILES: CNC(=O)c1cccc(C)c1Nc1nc(Nc2ccc(OC34CC5CC(C3)C(=O)C(C5)C4)cc2OC)ncc1C(F)(F)F]

[Step 1] Preparation of 5-(3-methoxy-4-nitrophenoxy) adamantan-2-one

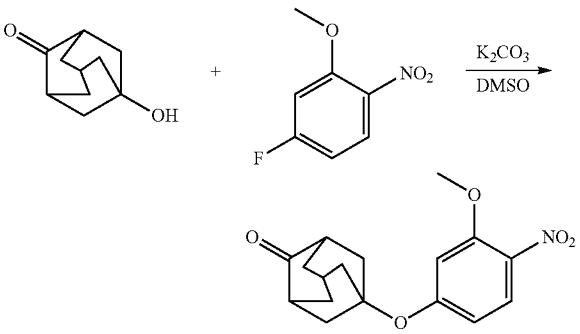

The title compound was synthesized in the same manner as in Example 1 by using 5-hydroxyadamantan-2-one instead of trans-4-aminoadamantan-1-ol in step 1 of Example 1.

[Step 2] Preparation of 5-(4-amino-3-methoxyphenoxy) adamantan-2-one

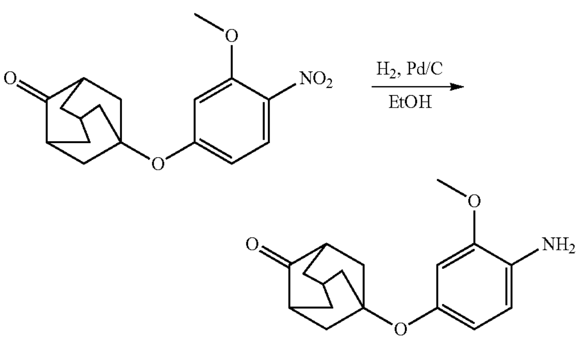

The title compound was synthesized in the same manner as in Example 1 by using 5-(3-methoxy-4-nitrophenoxy) adamantan-2-one instead of (trans)-4-((3-methoxy-4-nitrophenyl)amino) adamantan-1-ol in step 2 of Example 1.

[Step 3] Preparation of 5-(4-((4-chloro-5-(trifluoromethyl)pyrimidin-2-yl)amino)-3-methoxyphenoxy) adamantan-2-one

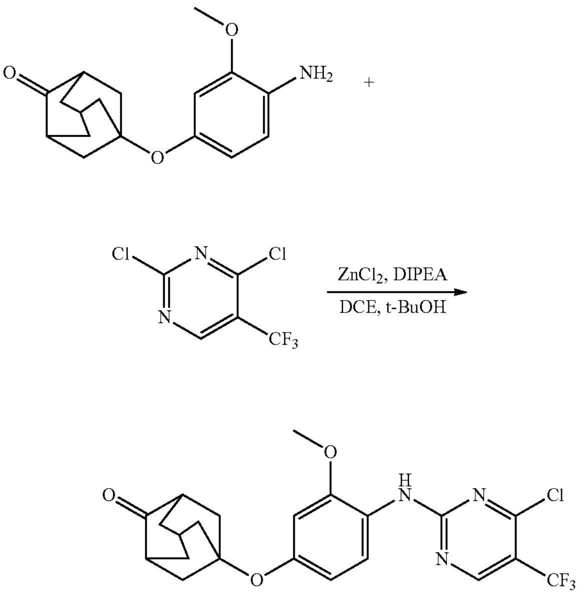

The title compound was synthesized in the same manner as in Example 1 by using 5-(4-amino-3-methoxyphenoxy) adamantan-2-one instead of (trans)-4-((4-amino-3-methoxyphenyl)amino) adamantan-1-ol in step 3 of Example 1.

[Step 6] Preparation of 2-((2-((2-methoxy-4-((4-oxoadamantan-1-yl)oxy)phenyl)amino)-5-(trifluoromethyl)pyrimidin-4-yl)amino)-N,3-dimethylbenzamide

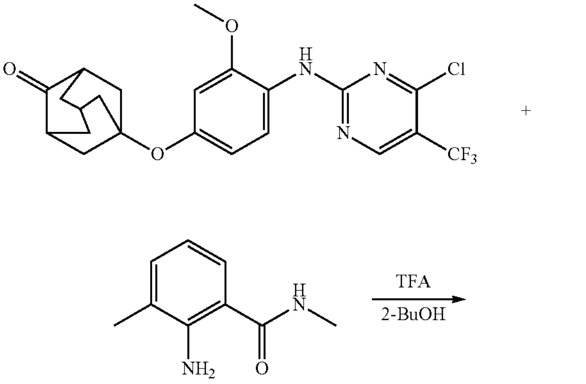

-continued

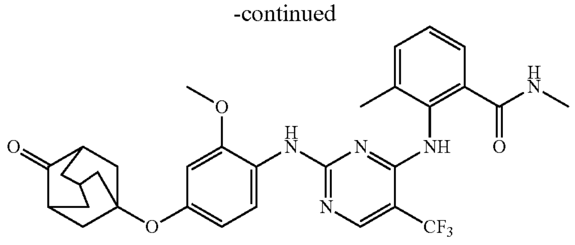

The title compound was synthesized in the same manner as in Example 1 by using N-(4-((1-(adamantan-2-yl)piperidin-4-yl)oxy)-2-methoxyphenyl)-4-chloro-5-(trifluoromethyl)pyrimidin-2-amine instead of (trans)-4-((4-((4-chloro-5-(trifluoromethyl)pyrimidin-2-yl)amino)-3-methoxyphenyl)amino) adamantan-1-ol in step 4 of Example 1.

$^{1}$H NMR (400 MHz, $CDCl_3$): δ 8.46 (s, 1H), 8.29 (s, 1H), 7.42-7.35 (m, 2H), 7.28 (t, J=7.6 Hz, 1H), 6.45 (d, J=2.4 Hz, 1H), 6.17 (br s, 1H), 6.02-5.96 (m, 1H), 3.81 (s, 3H), 2.88 (d, J=4.9 Hz, 3H), 2.67-2.62 (m, 2H), 2.40-2.34 (m, 1H), 2.20 (s, 3H), 2.19-2.01 (m, 6H), 1.96-1.92 (m, 4H)

<Example 11> Preparation of 2-((2-((4-((4-hydroxyadamantan-1-yl)oxy)-2-methoxyphenyl) amino)-5-(trifluoromethyl)pyrimidin-4-yl)amino)-N, 3-dimethylbenzamide (compound ii)

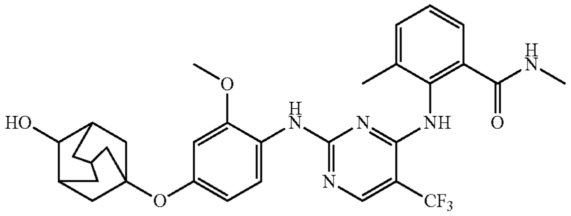 [SMILES: CNC(=O)c1cccc(C)c1Nc1nc(Nc2ccc(OC34CC5CC(C3)C(O)C(C5)C4)cc2OC)ncc1C(F)(F)F]

[Step 1] Preparation of 2-((2-((4-((4-hydroxyadamantan-1-yl)oxy)-2-methoxyphenyl)amino)-5-(trifluoromethyl)pyrimidin-4-yl)amino)-N,3-dimethylbenzamide

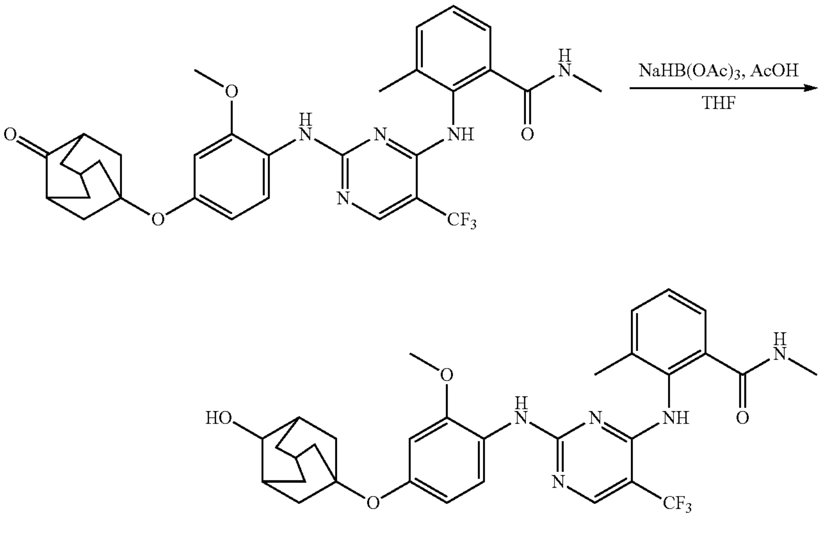

2-((2-((2-Methoxy-4-((4-oxoadamantan-1-yl)oxy)phenyl)amino)-5-(trifluoromethyl)pyrimidin-4-yl)amino)-N,3-dimethylbenzamide prepared in above Example 10, triacetoxysodium borohydride, tetrahydrofuran, and acetic acid were stirred at room temperature for 15 hours. Ice water was poured into the reaction solution, extracted with ethyl acetate, dried over anhydrous magnesium sulfate, and filtered, after which the filtrate was concentrated and purified by column chromatography to obtain the title compound.

$^{1}$H NMR (400 MHz, DMSO-$d_6$): δ 9.15 (s, 1H), 8.30 (s, 1H), 8.29-8.25 (m, 1H), 8.06 (s, 1H), 7.42 (d, J=7.4 Hz, 1H), 7.38 (d, J=7.2 Hz, 1H), 7.32-7.24 (m, 2H), 6.51 (d, J=1.8 Hz, 1H), 6.21 (br s, 1H), 4.66 (d, J=3.1 Hz, 1H), 3.70 (s, 3H), 3.69-3.66 (m, 1H), 2.69 (d, J=4.6, 3H), 2.10 (s, 3H), 2.05-1.91 (m, 5H), 1.84-1.71 (m, 6H), 1.26-1.23 (m, 2H)

<Example 12> Preparation of 2-((2-((2-methoxy-4-((4-morpholinoadamantan-1-yl)oxy)phenyl)amino)-5-(trifluoromethyl)pyrimidin-4-yl)amino)-N,3-dimethylbenzamide (compound 12)

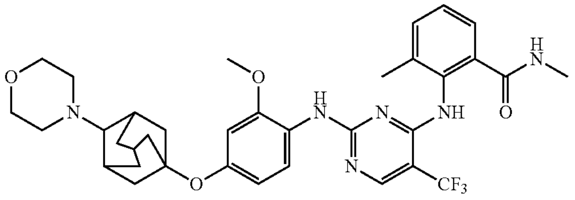 [SMILES: CNC(=O)c1cccc(C)c1Nc1nc(Nc2ccc(OC34CC5CC(C3)C(N3CCOCC3)C(C5)C4)cc2OC)ncc1C(F)(F)F]

[Step 1] Preparation of 2-((2-((2-methoxy-4-((4-morpholinoadamantan-1-yl)oxy)phenyl)amino)-5-(trifluoromethyl)pyrimidin-4-yl)amino)-N,3-dimethylbenzamide

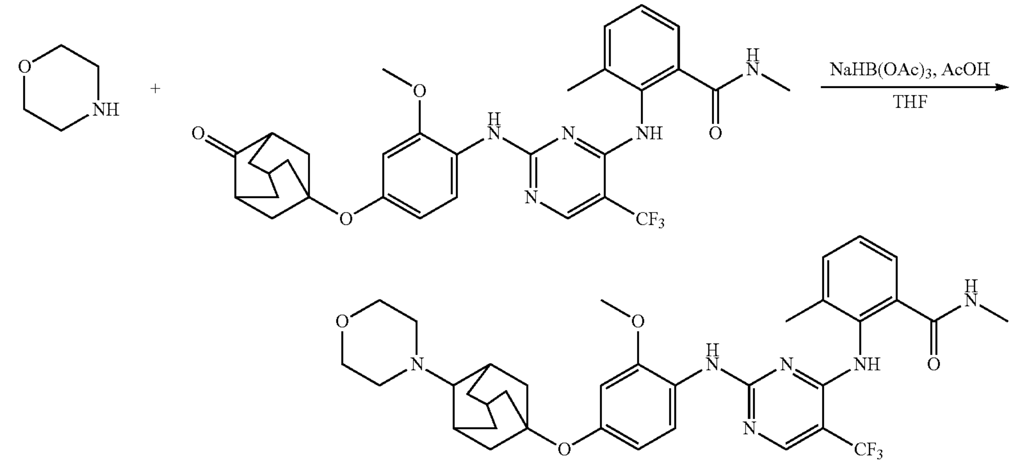

2-((2-((2-Methoxy-4-((4-oxoadamantan-1-yl)oxy)phenyl)amino)-5-(trifluoromethyl)pyrimidin-4-yl)amino)-N,3-dimethylbenzamide prepared in above Example 10, morpholine, triacetoxysodium borohydride, tetrahydrofuran, and acetic acid were stirred at room temperature for 15 hours. Ice water was poured into the reaction solution, extracted with ethyl acetate, dried over anhydrous magnesium sulfate, and filtered, after which the filtrate was concentrated and purified by column chromatography to obtain the title compound.

$^1$H NMR (400 MHz, DMSO-d$_6$): δ 9.07 (s, 1H), 8.24 (s, 1H), 8.23-8.17 (m, 1H), 8.01 (s, 1H), 7.38-7.30 (m, 2H), 7.26-7.19 (m, 2H), 6.46 (s, 1H), 6.15 (br s, 1H), 3.65 (s, 3H), 3.54 (br s, 4H), 3.27 (s, 3H), 2.63 (d, J=4.5 Hz, 3H), 2.45 (br s, 4H), 2.34-2.15 (m, 5H), 2.04 (s, 3H), 1.92-1.64 (m, 7H), 1.21-1.11 (m, 2H)

<Example 13> Preparation of 2-((2-((2-methoxy-4-((4-(4-methylpiperazin-1-yl) adamantan-1-yl)oxy)phenyl)amino)-5-(trifluoromethyl)pyrimidin-4-yl)amino)-N,3-dimethylbenzamide (compound 13)

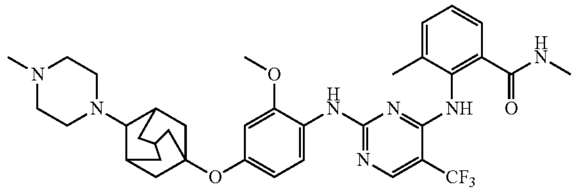

[Step 1] Preparation of 2-((2-((2-methoxy-4-((4-(4-methylpiperazin-1-yl) adamantan-1-yl)oxy)phenyl)amino)-5-(trifluoromethyl)pyrimidin-4-yl)amino)-N,3-dimethylbenzamide

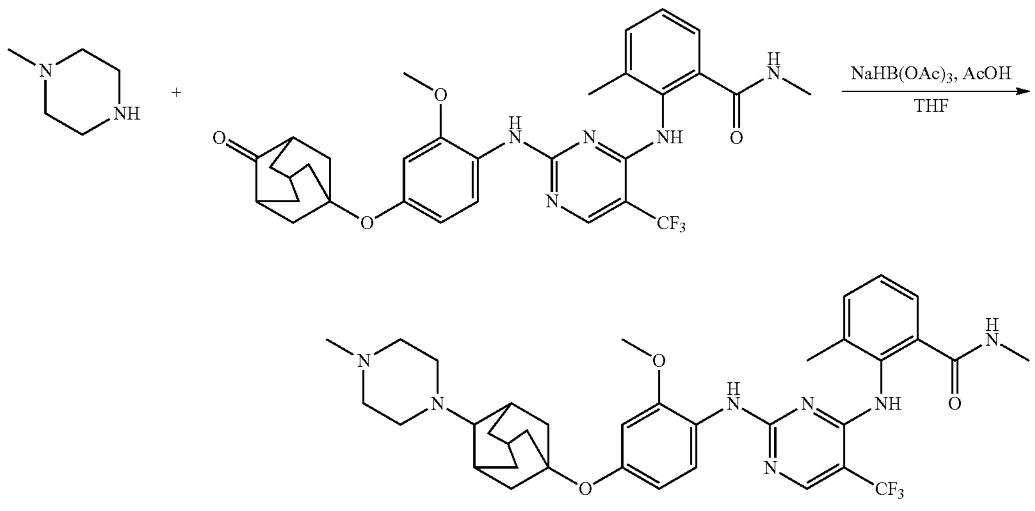

The title compound was synthesized in the same manner as in Example 12 by using 4-methylpiperazine instead of morpholine in step 1 of Example 12.

$^1$H NMR (400 MHz, $CDCl_3$): δ 8.50 (s, 1H), 8.26 (s, 1H), 7.42-7.36 (m, 2H), 7.28 (t, J=7.5 Hz, 1H), 6.45 (d, J=2.3 Hz, 1H), 6.21-6.08 (m, 2H), 3.80 (s, 3H), 3.50-3.40 (m, 2H), 3.15-2.65 (m, 12H), 2.28-2.22 (m, 1H), 2.20 (s, 3H), 2.16-1.64 (m, 11H), 1.32-1.22 (m, 2H)

<Example 14> Preparation of 2-((2-((4-(((trans)-4-((S)-3-acetamidopyrrolidin-1-yl) adamantan-1-yl) oxy)-2-methoxyphenyl)amino)-5-(trifluoromethyl) pyrimidin-4-yl)amino)-N,3-dimethylbenzamide (compound 14)

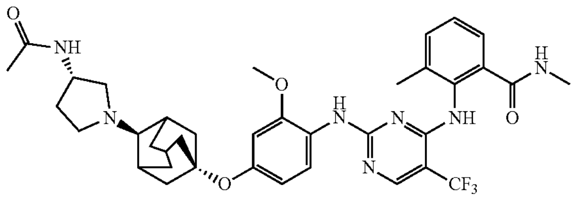 [SMILES: CNC(=O)c1cccc(C)c1Nc1nc(Nc2ccc(O[C@]34CC5CC(C3)[C@@H](N3CC[C@H](NC(C)=O)C3)C(C5)C4)cc2OC)ncc1C(F)(F)F]

[Step 1] Preparation of 2-((2-((4-(((trans)-4-((S)-3-acetamidopyrrolidin-1-yl) adamantan-1-yl)oxy)-2-methoxyphenyl)amino)-5-(trifluoromethyl)pyrimidin-4-yl)amino)-N,3-dimethylbenzamide

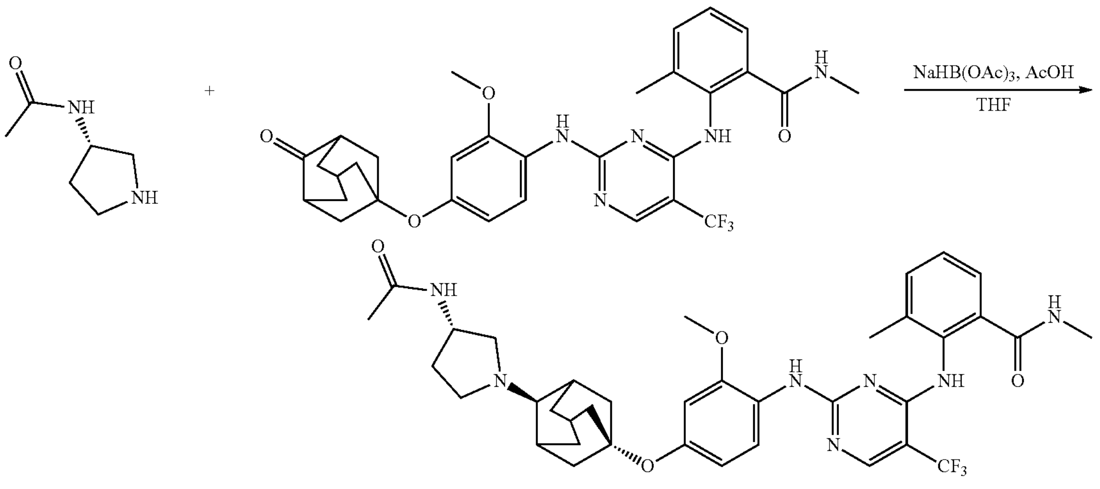

The title compound was synthesized in the same manner as in Example 12 by using (S)-N-(pyrrolidin-3-yl)acetamide instead of morpholine in step 1 of Example 12.

$^1$H NMR (400 MHz, DMSO-$d_6$): δ 9.14 (s, 1H), 8.29 (s, 1H), 8.28-8.24 (m, 1H), 8.04 (s, 1H), 7.95 (d, J=6.6 Hz, 1H), 7.42 (d, J=7.5 Hz, 1H), 7.38 (d, J=7.1 Hz, $^1$H), 7.32-7.24 (m, 2H), 6.50 (d, J=1.7 Hz, 1H), 6.20 (br s, 1H), 5.75 (s, 1H), 4.19-4.08 (m, 1H), 3.70 (s, 3H), 2.77-2.62 (m, 4H), 2.55 (m, 1H), 2.43 (m, 1H), 2.24 (m, 1H), 2.21-1.90 (m, 10H), 1.78 (s, 3H), 1.71 (m, 2H), 1.56-1.43 (m, 7H)

<Example 15> Preparation of 2-((2-((4-(((cis)-4-((S)-3-acetamidopyrrolidin-1-yl) adamantan-1-yl) oxy)-2-methoxyphenyl)amino)-5-(trifluoromethyl) pyrimidin-4-yl)amino)-N,3-dimethylbenzamide (compound 15)

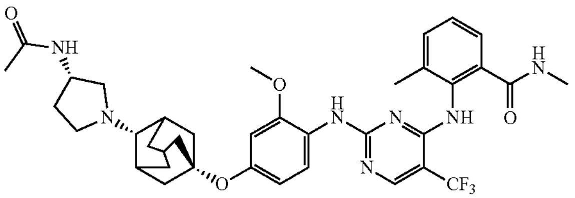 [SMILES: CNC(=O)c1cccc(C)c1Nc1nc(Nc2ccc(O[C@]34CC5CC(C3)[C@H](N3CC[C@H](NC(C)=O)C3)C(C5)C4)cc2OC)ncc1C(F)(F)F]

[Step 1] Preparation of 2-((2-((4-(((cis)-4-((S)-3-acetamidopyrrolidin-1-yl) adamantan-1-yl)oxy)-2-methoxyphenyl)amino)-5-(trifluoromethyl)pyrimidin-4-yl)amino)-N,3-dimethylbenzamide

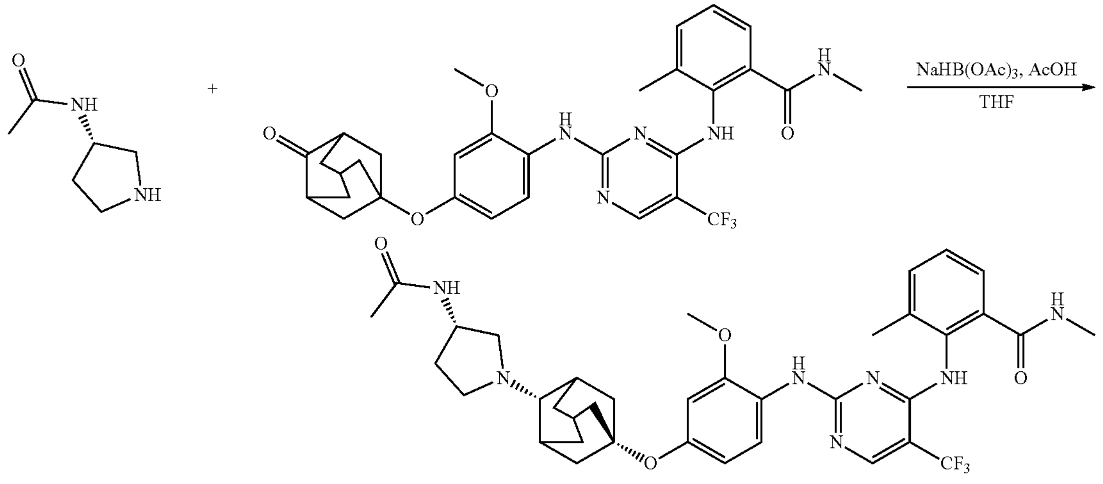

The title compound was synthesized in the same manner as in Example 12 by using (S)-N-(pyrrolidin-3-yl)acetamide instead of morpholine in step 1 of Example 12.

$^1$H NMR (400 MHz, DMSO-$d_6$): δ 9.13 (s, 1H), 8.30 (s, 1H), 8.29-8.23 (m, 1H), 8.05 (s, 1H), 7.93 (d, J=4.9 Hz, 1H), 7.41 (d, J=7.5 Hz, 1H), 7.38 (d, J=7.1 Hz, $^1$H), 7.32-7.24 (m, 2H), 6.52 (d, J=1.2 Hz, 1H), 6.21 (br s, 1H), 5.75 (s, 1H), 4.19-4.08 (m, 1H), 3.70 (s, 3H), 2.81-2.54 (m, 4H), 2.50 (m, 1H), 2.44-2.20 (m, 2H), 2.20-1.87 (m, 8H), 1.87-1.64 (m, 7H), 1.64-1.38 (m, 2H), 1.38-1.04 (m, 5H).

<Example 16> Preparation of 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate (compound 16)

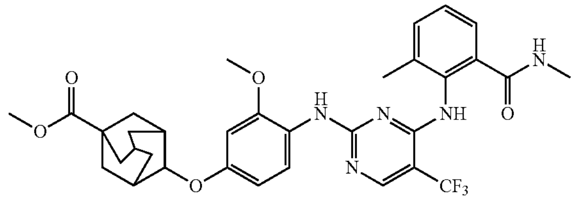

[Step 1] Preparation of 4-(3-methoxy-4-nitrophenoxy) adamantan-1-methyl carboxylate

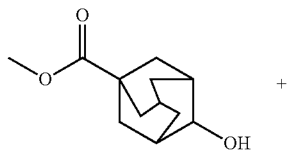

-continued

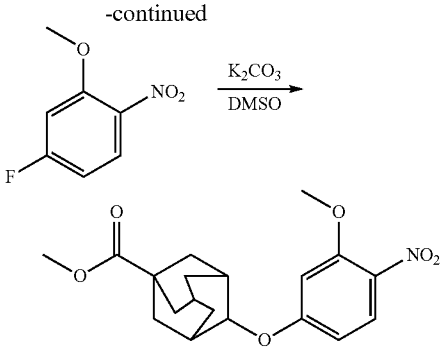

The title compound was synthesized in the same manner as in Example 1 by using 4-hydroxyadamantan-1-methyl carboxylate instead of trans-4-aminoadamantan-1-ol in step 1 of Example 1.

[Step 2] Preparation of 4-(4-amino-3-methoxyphenoxy) adamantan-1-methyl carboxylate

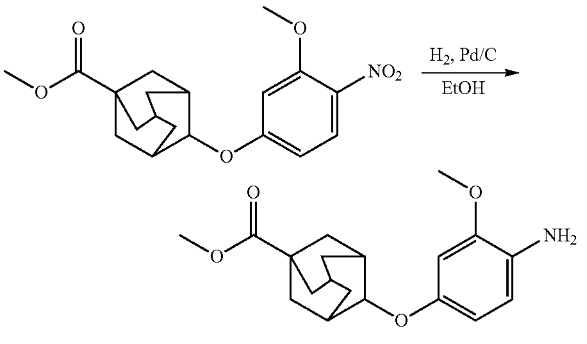

The title compound was synthesized in the same manner as in Example 1 by using 4-(3-methoxy-4-nitrophenoxy)

adamantan-1-methyl carboxylate instead of (trans)-4-((3-methoxy-4-nitrophenyl)amino) adamantan-1-ol in step 2 of Example 1.

[Step 3] Preparation of 4-(4-((4-chloro-5-(trifluoromethyl)pyrimidin-2-yl)amino)-3-methoxyphenoxy) adamantan-1-methyl carboxylate

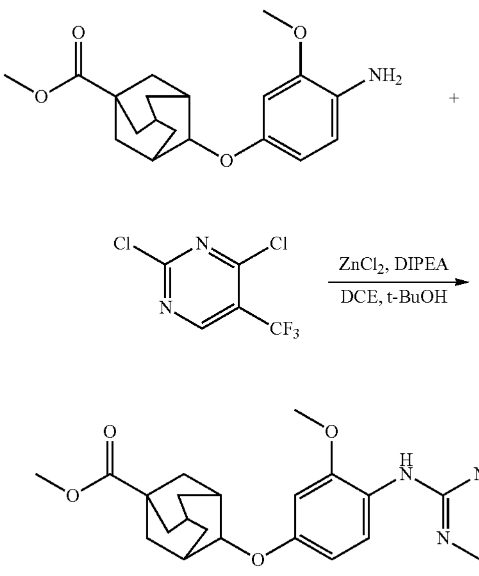

The title compound was synthesized in the same manner as in Example 1 by using 4-(4-amino-3-methoxyphenoxy) adamantan-1-methyl carboxylate instead of (trans)-4-((4-amino-3-methoxyphenyl)amino) adamantan-1-ol in step 3 of Example 1.

[Step 4] Preparation of 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate

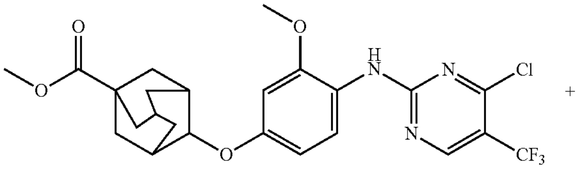

-continued

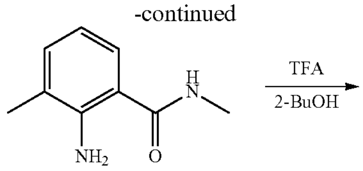

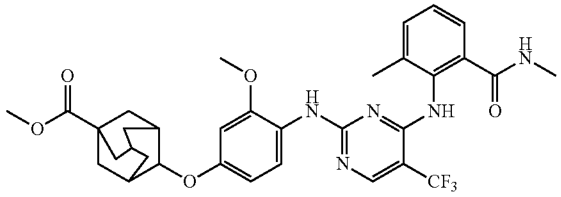

The title compound was synthesized in the same manner as in Example 1 by using 4-(4-((4-chloro-5-(trifluoromethyl)pyrimidin-2-yl)amino)-3-methoxyphenoxy)adamantane-1-methyl carboxylate instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.40 (s, 1H), 8.26 (s, 1H), 7.51 (s, 2H), 7.30 (m, 3H), 6.44 (s, 1H), 6.11 (m, 2H), 4.25 (m, 1H), 3.79 (s, 3H), 3.66 (m, 3H), 2.82 (d, J=4.9 Hz, 3H), 2.32-2.10 (m, 6H), 2.06-1.80 (m, 7H), 1.77-1.65 (m, 2H), 1.48 (m, 1H)

<Example 17> Preparation of 4-(3-methoxy-4-((4-((2-methyl-6-(methylcarbamoyl)phenyl)amino)-5-(trifluoromethyl)pyrimidin-2-yl)amino)phenoxy) adamantan-1-carboxylic acid (compound 17)

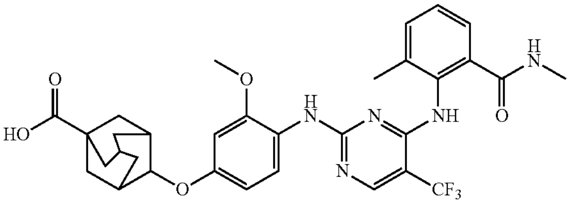 [SMILES: CNC(=O)c1cccc(C)c1Nc1nc(Nc2ccc(OC3C4CC5CC3CC(C(=O)O)(C5)C4)cc2OC)ncc1C(F)(F)F]

[Step 1] Preparation of 4-(3-methoxy-4-((4-((2-methyl-6-(methylcarbamoyl)phenyl)amino)-5-(trifluoromethyl)pyrimidin-2-yl)amino)phenoxy) adamantan-1-carboxylic acid

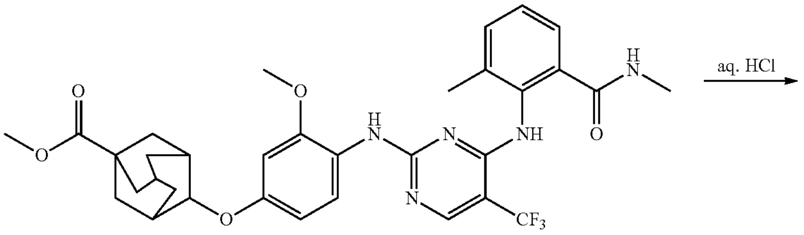

-continued

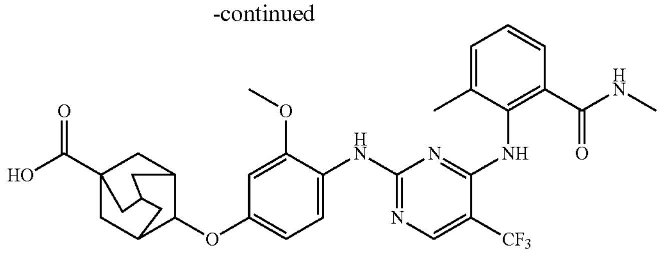

Aqueous solution of hydrochloric acid was added to 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate prepared in above Example 16, and stirred under reflux for five hours. After completion of the reaction, distilled water was added to the reaction solution, followed by extraction with dichloromethane. The resulting solution was dried over anhydrous magnesium sulfate, and filtered, after which the filtrate was concentrated and purified by column chromatography to obtain the title compound.

$^{1}$H NMR (400 MHz, $CDCl_3$): δ 8.16 (s, 1H), 7.43-7.28 (m, 4H), 6.43 (m, 1H), 6.02 (s, 2H), 4.28 (m, 1H), 3.82 (m, 3H), 2.90 (d, J=4.2 Hz, 3H), 2.61 (m, 1H), 2.27 (m, 3H), 2.16 (s, 3H), 2.11-1.84 (m, 5H), 1.79-1.70 (m, 3H), 1.52 (m, 1H)

<Example 18> Preparation of 4-(3-methoxy-4-((4-((2-methyl-6-(methylcarbamoyl)phenyl)amino)-5-(trifluoromethyl)pyrimidin-2-yl)amino)phenoxy)-N-methyladamantan-1-carboxamide (compound 18)

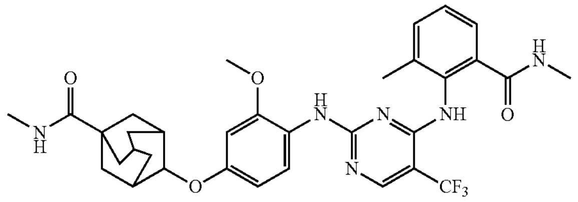

[Step 1] Preparation of 4-(3-methoxy-4-((4-((2-methyl-6-(methylcarbamoyl)phenyl)amino)-5-(trifluoromethyl)pyrimidin-2-yl)amino)phenoxy)-N-methyladamantan-1-carboxamide

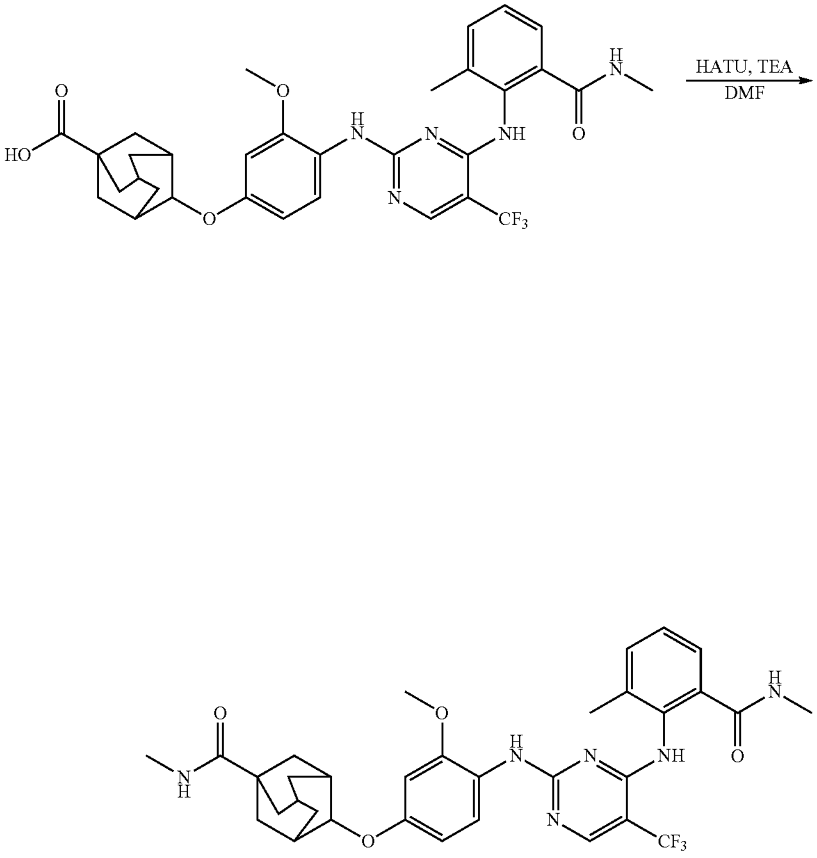

4-(3-Methoxy-4-((4-((2-methyl-6-(methylcarbamoyl)phenyl)amino)-5-(trifluoromethyl)pyrimidin-2-yl)amino)phenoxy) adamantan-1-carboxylic acid prepared in above Example 16, methylamine hydrochloride, 1-[bis(dimethylamino)methylene]-1H-1,2,3-triazolo[4,5-b]pyridinium 3-oxide hexafluorophosphate were dissolved in N,N-dimethylformamide, after which triethylamine was added and stirred at room temperature for five hours. After completion of the reaction, distilled water was added to the reaction solution, followed by extraction with ethyl acetate. The resulting solution was dried over anhydrous magnesium sulfate, and filtered, after which the filtrate was concentrated and purified by column chromatography to obtain the title compound.

$^1$H NMR (400 MHz, $CDCl_3$): δ 8.33 (s, 1H), 8.28 (s, 1H), 7.52 (s, 2H), 7.38 (m, 2H), 7.33-7.18 (m, 1H), 6.46 (s, 1H), 6.03 (m, 2H), 5.63 (s, 1H), 4.28 (m, 1H), 3.82 (s, 3H), 2.91-2.72 (m, 6H), 2.30-2.12 (m, 6H), 2.09-1.82 (m, 6H), 1.79-1.63 (m, 2H), 1.53-1.43 (m, 2H)

<Example 19> Preparation of 2-((2-((2-methoxy-4-((5-(morpholin-4-carbonyl) adamantan-2-yl)oxy) phenyl)amino)-5-(trifluoromethyl)pyrimidin-4-yl) amino)-N,3-dimethylbenzamide (compound 19)

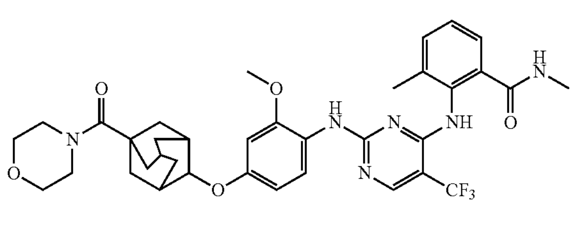 [SMILES: CNC(=O)c1cccc(C)c1Nc1nc(Nc2ccc(OC3C4CC5CC3CC(C(=O)N3CCOCC3)(C5)C4)cc2OC)ncc1C(F)(F)F]

[Step 1] Preparation of 2-((2-((2-methoxy-4-((5-(morpholin-4-carbonyl) adamantan-2-yl)oxy)phenyl) amino)-5-(trifluoromethyl)pyrimidin-4-yl)amino)-N, 3-dimethylbenzamide

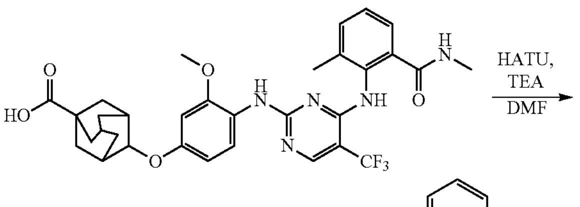

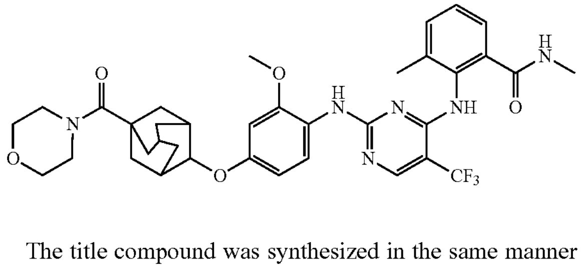

The title compound was synthesized in the same manner as in Example 18 by using morpholine instead of methylamine hydrochloride in step 1 of Example 18.

$^1$H NMR (400 MHz, $CDCl_3$): δ 8.36 (m, 1H), 8.28 (s, 1H), 7.52 (s, 2H), 7.38 (m, 2H), 7.34-7.26 (m, 1H), 6.43 (m, 1H), 6.01 (m, 2H), 4.28 (s, 1H), 3.81 (m, 3H), 3.78-3.65 (m, 6H), 2.87 (m, 3H), 2.41 (m, 1H), 2.31-2.13 (m, 6H), 2.12-1.95 (m, 3H), 1.92-1.81 (m, 1H), 1.80-1.67 (m, 2H), 1.65-1.45 (m, 2H)

<Example 20> Preparation of 2-((2-((2-methoxy-4-((5-(4-methylpiperazin-1-carbonyl) adamantan-2-yl) oxy)phenyl)amino)-5-(trifluoromethyl)pyrimidin-4-yl)amino)-N,3-dimethylbenzamide (compound 20)

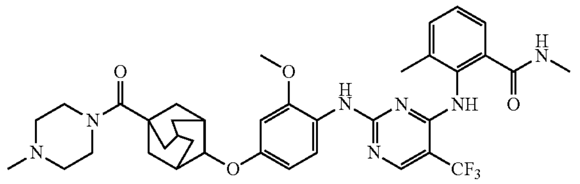

[Step 1] Preparation of 2-((2-((2-methoxy-4-((5-(4-methylpiperazin-1-carbonyl) adamantan-2-yl)oxy) phenyl)amino)-5-(trifluoromethyl)pyrimidin-4-yl) amino)-N,3-dimethylbenzamide

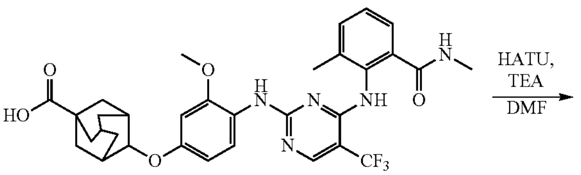

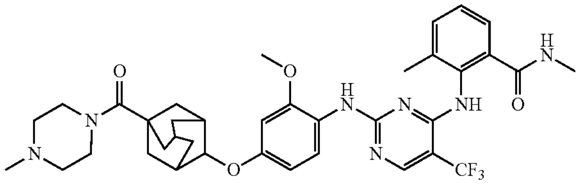

The title compound was synthesized in the same manner as in Example 18 by using 1-methylpiperazine instead of methylamine hydrochloride in step 1 of Example 18.

$^1$H NMR (400 MHz, $CDCl_3$): δ 8.35 (s, 1H), 8.27 (s, 1H), 7.51 (s, 2H), 7.38 (m, 2H), 7.32-7.26 (m, 1H), 6.50-6.38 (m, 1H), 6.02 (s, 2H), 4.28 (m, 1H), 3.81 (m, 3H), 3.74 (m, 4H), 2.86 (d, J=4.7 Hz, 3H), 2.41 (s, 5H), 2.31 (s, 3H), 2.29-2.12 (m, 6H), 2.01 (m, 4H), 1.87 (m, 2H), 1.71 (m, 2H), 1.51 (m, 1H)

<Example 21> Preparation of 2-((2-((2-methoxy-4-((5-((S)-3-acetamidopyrrolidin-1-carbonyl) adamantan-2-yl)oxy)phenyl)amino)-5-(trifluoromethyl)pyrimidin-4-yl)amino)-N,3-dimethylbenzamide (compound 21)

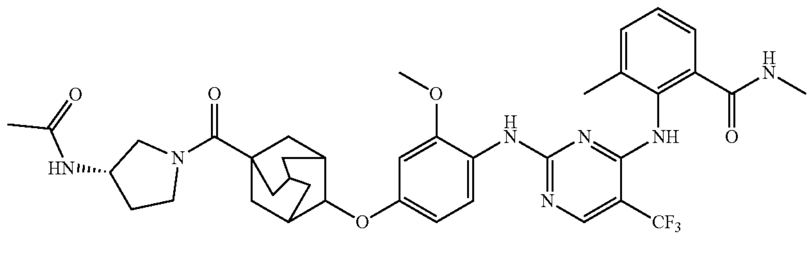 [SMILES: CNC(=O)c1cccc(C)c1Nc1nc(Nc2ccc(OC3C4CC5CC3CC(C(=O)N3CC[C@H](NC(C)=O)C3)(C5)C4)cc2OC)ncc1C(F)(F)F]

[Step 1] Preparation of 2-((2-((2-methoxy-4-((5-((S)-3-acetamidopyrrolidin-1-carbonyl) adamantan-2-yl)oxy)phenyl)amino)-5-(trifluoromethyl)pyrimidin-4-yl)amino)-N,3-dimethylbenzamide

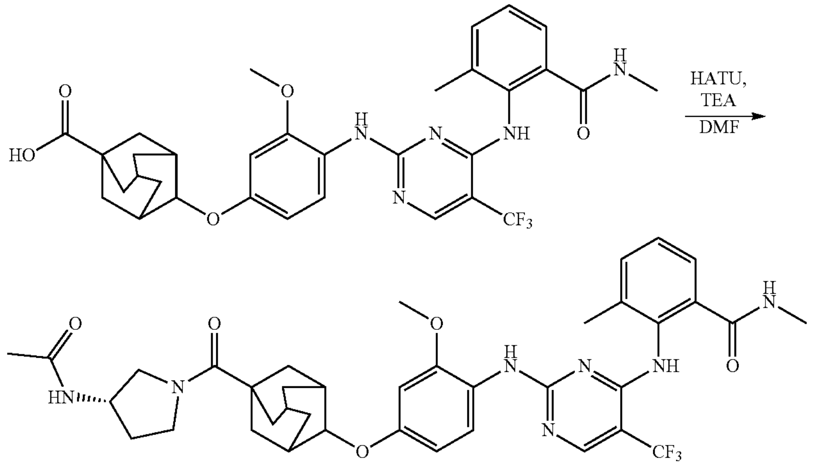

The title compound was synthesized in the same manner as in Example 18 by using (S)-N-(pyrrolidin-3-yl)acetamide instead of methylamine hydrochloride in step 1 of Example 18.

$^1$H NMR (400 MHz, $CDCl_3$): δ 8.37 (m, 1H), 8.27 (s, 1H), 7.50 (s, 2H), 7.43-7.34 (m, 2H), 7.29 (m, 1H), 6.46 (m, 1H), 6.10 (m, 2H), 5.58 (m, 1H), 4.45 (m, 1H), 4.27 (m, 1H), 3.82 (s, 3H), 3.75-3.52 (m, 3H), 2.86 (d, J=4.7 Hz, 3H), 2.38 (m, 1H), 2.29-2.11 (m, 7H), 2.01 (m, 6H), 1.90-1.80 (m, 2H), 1.77-1.68 (m, 2H), 1.59 (br s, 2H), 1.50 (m, 1H)

<Example 22> Preparation of 2-((2-((2-methoxy-4-((5-(morpholin-4-carbonyl) adamantan-2-yl)amino) phenyl)amino)-5-(trifluoromethyl)pyrimidin-4-yl) amino)-N,3-dimethylbenzamide (compound 22)

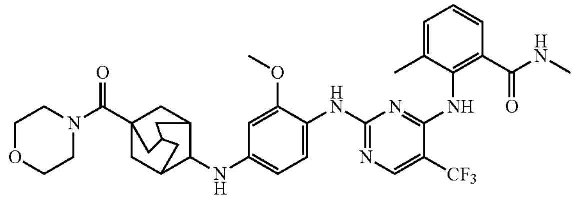 [SMILES: CNC(=O)c1cccc(C)c1Nc1nc(Nc2ccc(NC3C4CC5CC3CC(C(=O)N3CCOCC3)(C5)C4)cc2OC)ncc1C(F)(F)F]

[Step 1] Preparation of 4-((3-methoxy-4-nitrophenyl)amino) adamantan-1-methyl carboxylate

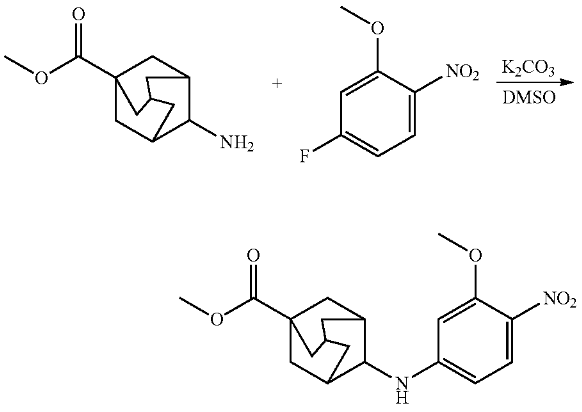

The title compound was synthesized in the same manner as in Example 1 by using 4-aminoadamantan-1-methyl carboxylate instead of trans-4-aminoadamantan-1-ol in step 1 of Example 1.

[Step 2] Preparation of 4-((4-amino-3-methoxyphenyl)amino) adamantan-1-methyl carboxylate

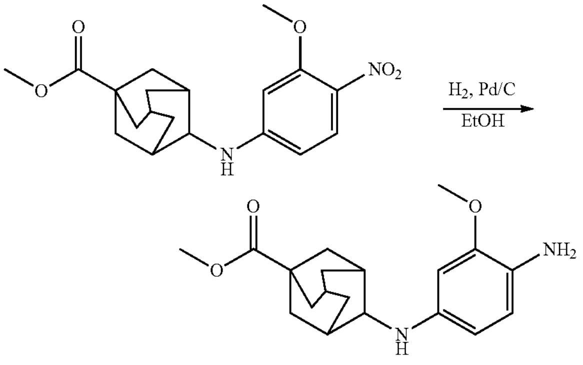

The title compound was synthesized in the same manner as in Example 1 by using 4-((3-methoxy-4-nitrophenyl) amino) adamantan-1-methyl carboxylate instead of (trans)-4-((3-methoxy-4-nitrophenyl)amino) adamantan-1-ol in step 2 of Example 1.

[Step 3] Preparation of 4-((4-((4-chloro-5-(trifluoromethyl)pyrimidin-2-yl)amino)-3-methoxyphenyl) amino) adamantan-1-methyl carboxylate

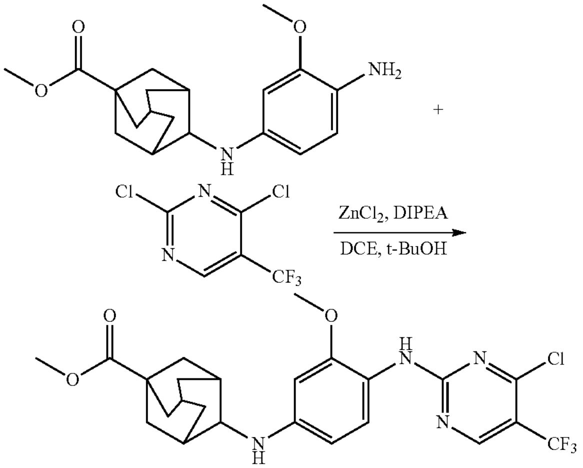

The title compound was synthesized in the same manner as in Example 1 by using 4-((4-amino-3-methoxyphenyl) amino) adamantan-1-methyl carboxylate instead of (trans)-4-((4-amino-3-methoxyphenyl)amino) adamantan-1-ol in step 3 of Example 1.

[Step 4] Preparation of 4-((3-methoxy-4-((4-((2-methyl-6-(methylcarbamoyl)phenyl)amino)-5-(trifluoromethyl)pyrimidin-2-yl)amino)phenyl)amino) adamantan-1-methyl carboxylate

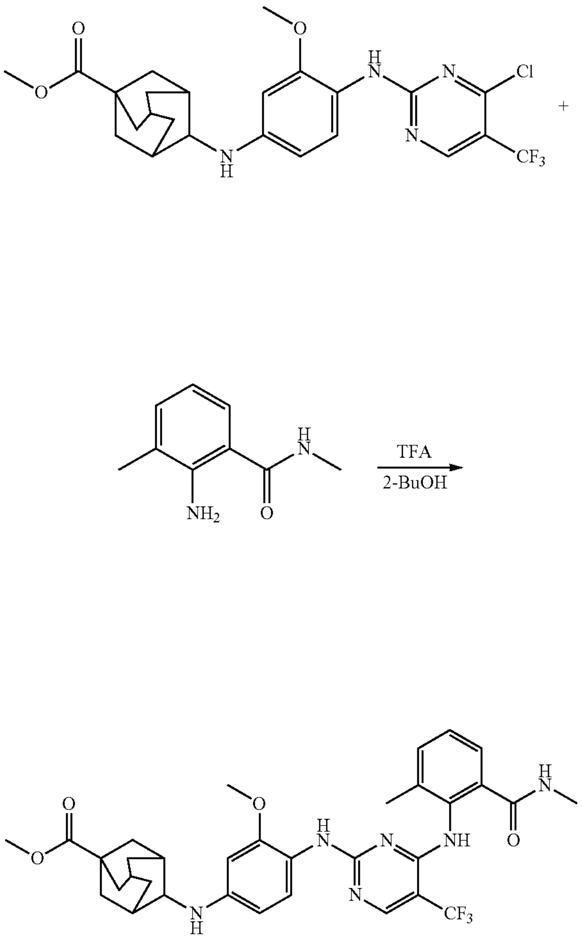

The title compound was synthesized in the same manner as in Example 1 by using 4-((4-((4-chloro-5-(trifluoromethyl)pyrimidin-2-yl)amino)-3-methoxyphenyl)amino)adamantane-1-methyl carboxylate instead of (trans)-4-((4-((4-chloro-5-(trifluoromethyl)pyrimidin-2-yl)amino)-3-methoxyphenyl)amino) adamantan-1-ol in step 4 of Example 1.

[Step 5] Preparation of 4-((3-methoxy-4-((4-((2-methyl-6-(methylcarbamoyl)phenyl)amino)-5-(trifluoromethyl)pyrimidin-2-yl)amino)phenyl)amino) adamantan-1-carboxylic acid

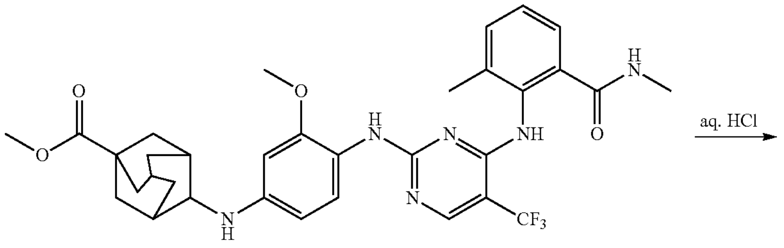

-continued

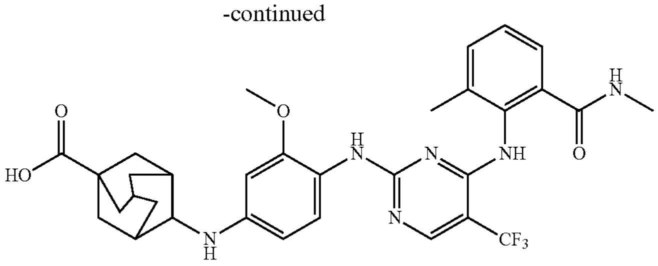

The title compound was synthesized in the same manner as in Example 17 by using 4-((3-methoxy-4-((4-((2-methyl-6-(methylcarbamoyl)phenyl)amino)-5-(trifluoromethyl)pyrimidin-2-yl)amino)phenyl)amino)adamantane-1-methyl carboxylate instead of 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate in step 1 of Example 17.

[Step 6] Preparation of 2-((2-((2-methoxy-4-((5-(morpholin-4-carbonyl) adamantan-2-yl)amino)phenyl)amino)-5-(trifluoromethyl)pyrimidin-4-yl) amino)-N,3-dimethylbenzamide

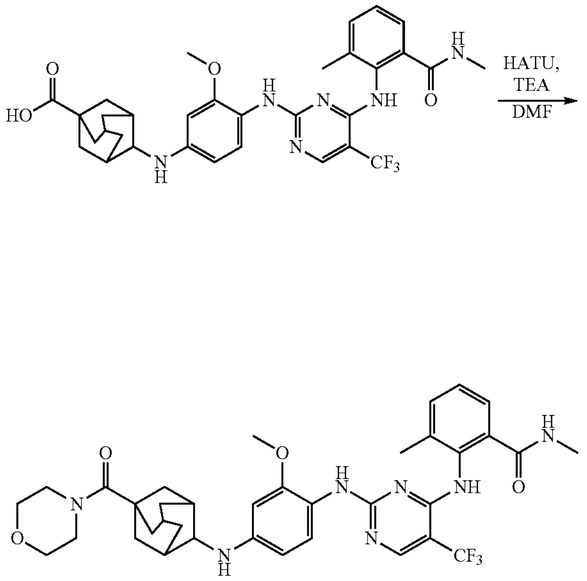

The title compound was synthesized in the same manner as in Example 19 by using 4-((3-methoxy-4-((4-((2-methyl-6-(methylcarbamoyl)phenyl)amino)-5-(trifluoromethyl)pyrimidin-2-yl)amino)phenyl)amino)adamantane-1-carboxylic acid instead of 4-(3-methoxy-4-((4-((2-methyl-6-(methylcarbamoyl)phenyl)amino)-5-(trifluoromethyl) pyrimidin-2-yl)amino)phenoxy) adamantan-1-carboxylic acid in step 1 of Example 19.

$^1$H NMR (400 MHz, $CDCl_3$): δ 8.24 (s, 1H), 8.19 (s, 1H), 7.62-7.32 (m, 3H), 7.32-7.26 (m, 2H), 6.11 (d, J=2.0 Hz, 1H), 6.03 (s, 1H), 5.73 (s, 1H), 3.77 (s, 3H), 3.68 (m, 8H), 3.41 (s, 1H), 2.84 (d, J=4.7 Hz, 3H), 2.20 (s, 3H), 2.18-2.05 (m, 6H), 2.00 (s, 2H), 1.90-1.79 (m, 6H)

<Example 23> Preparation of 2-((2-((2-methoxy-4-((5-(4-methylpiperazin-1-carbonyl) adamantan-2-yl) amino)phenyl)amino)-5-(trifluoromethyl)pyrimidin-4-yl)amino)-N,3-dimethylbenzamide (compound 23)

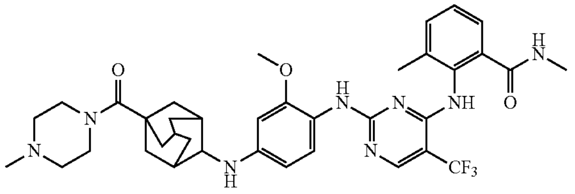

[Step 1] Preparation of 2-((2-((2-methoxy-4-((5-(4-methylpiperazin-1-carbonyl) adamantan-2-yl)amino) phenyl)amino)-5-(trifluoromethyl)pyrimidin-4-yl) amino)-N,3-dimethylbenzamide

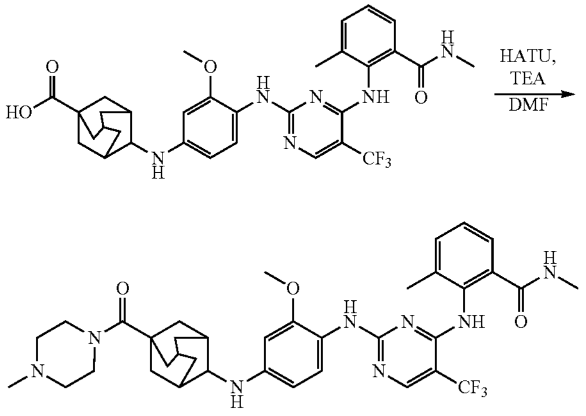

The title compound was synthesized in the same manner as in Example 22 by using 1-methylpiperazine instead of morpholine in step 6 of Example 22.

$^1$H NMR (400 MHz, $CDCl_3$): δ 8.24 (s, 1H), 8.15 (s, 1H), 7.37 (m, 3H), 7.31-7.25 (m, 1H), 6.11 (d, J=1.6 Hz, 1H), 6.03 (s, 1H), 5.72 (s, 1H), 3.77 (s, 3H), 3.71 (s, 4H), 3.41 (s, 1H), 2.83 (d, J=4.6 Hz, 3H), 2.48-2.32 (m, 4H), 2.29 (s, 3H), 2.20 (s, 3H), 2.17-1.96 (m, 7H), 1.94-1.77 (m, 6H)

<Example 24> Preparation of 2-((2-((2-methoxy-4-((5-((S)-3-acetamidopyrrolidin-1-carbonyl) adamantan-2-yl)amino)phenyl)amino)-5-(trifluoromethyl) pyrimidin-4-yl)amino)-N,3-dimethylbenzamide (compound 24)

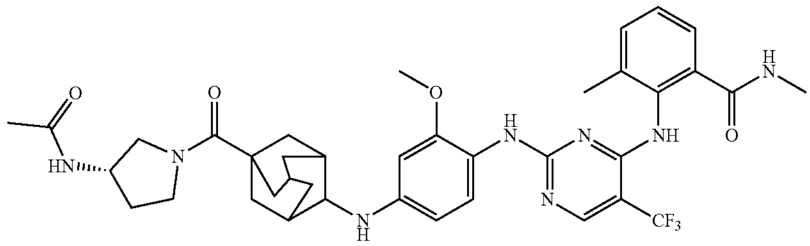 [SMILES: CNC(=O)c1cccc(C)c1Nc1nc(Nc2ccc(NC3C4CC5CC3CC(C(=O)N3CC[C@H](NC(C)=O)C3)(C5)C4)cc2OC)ncc1C(F)(F)F]

[Step 1] Preparation of 2-((2-((2-methoxy-4-((5-((S)-3-acetamidopyrrolidin-1-carbonyl) adamantan-2-yl)amino)phenyl)amino)-5-(trifluoromethyl)pyrimidin-4-yl)amino)-N,3-dimethylbenzamide

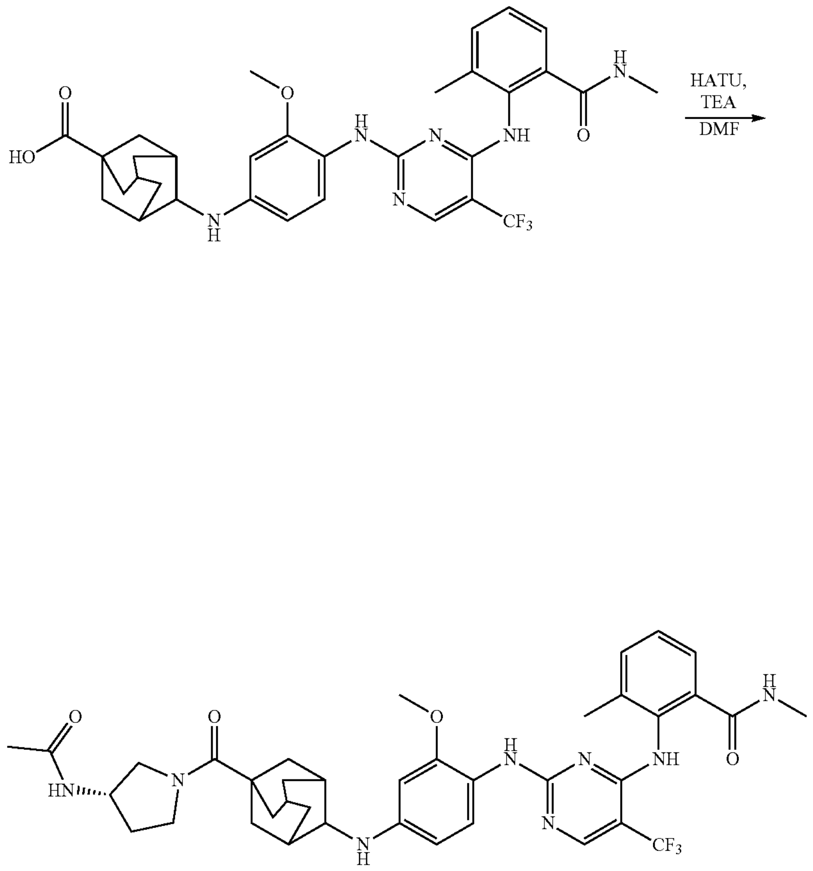

The title compound was synthesized in the same manner as in Example 22 by using (S)-N-(pyrrolidin-3-yl)acetamide instead of morpholine in step 6 of Example 22.

$^1$H NMR (400 MHz, $CDCl_3$): δ 8.24 (s, 1H), 8.14 (s, 1H), 7.45-7.32 (m, 3H), 7.32-7.26 (m, 1H), 6.13 (d, J=2.2 Hz, 1H), 6.07 (s, 1H), 5.74 (s, 1H), 5.62 (m, 1H), 4.42 (m, 1H), 3.86 (s, 1H), 3.78 (s, 3H), 3.63 (m, 3H), 3.41 (s, 1H), 2.83 (d, J=4.5 Hz, 3H), 2.21 (s, 3H), 2.18-2.03 (m, 8H), 1.98 (m, 4H), 1.83 (m, 6H)

<Example 25> Preparation of N-(3-methoxy-4-((4-((2-methyl-6-(methylcarbamoyl)phenyl)amino)-5-(trifluoromethyl)pyrimidin-2-yl)amino)phenyl)-4-morpholinoadamantan-1-carboxamide (compound 25)

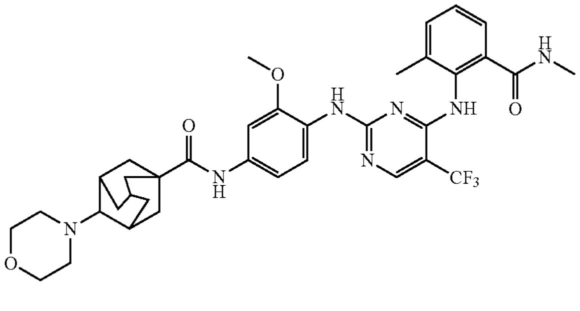 [SMILES: CNC(=O)c1cccc(C)c1Nc1nc(Nc2ccc(NC(=O)C34CC5CC(C3)C(N3CCOCC3)C(C5)C4)cc2OC)ncc1C(F)(F)F]

[Step 1] Preparation of N-(3-methoxy-4-nitrophenyl)-4-oxoadamantan-1-carboxamide

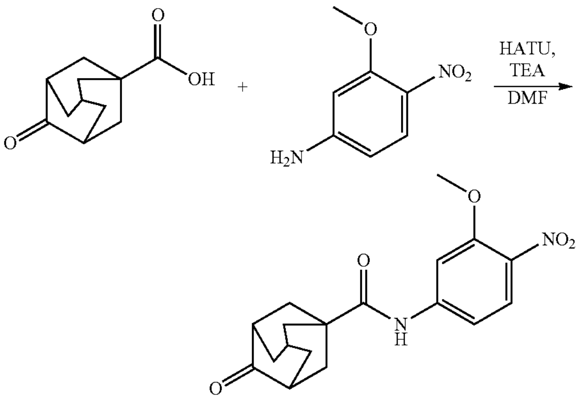

4-Oxoadamantan-1-carboxylic acid, 3-methoxy-4-nitroaniline, and 1-[bis(dimethylamino)methylene]-1H-1,2,3-triazolo[4,5-b]pyridinium 3-oxide hexafluorophosphate were dissolved in N,N-dimethylformamide, after which triethylamine was added and stirred at room temperature for five hours. After completion of the reaction, distilled water was added to the reaction solution, followed by extraction with ethyl acetate. The resulting solution was dried over anhydrous magnesium sulfate, and filtered, after which the filtrate was concentrated and purified by column chromatography to obtain the title compound.

[Step 2] Preparation of N-(4-amino-3-methoxyphenyl)-4-oxoadamantan-1-carboxamide

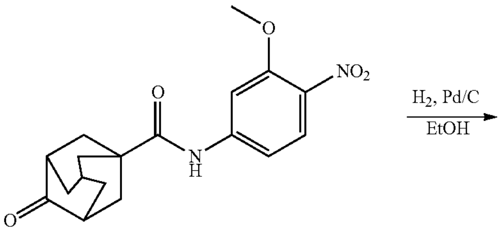

-continued

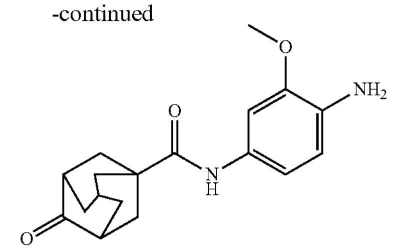

The title compound was synthesized in the same manner as in Example 1 by using N-(3-methoxy-4-nitrophenyl)-4-oxoadamantan-1-carboxamide instead of (trans)-4-((3-methoxy-4-nitrophenyl)amino) adamantan-1-ol in step 2 of Example 1.

[Step 3] Preparation of N-(4-((4-chloro-5-(trifluoromethyl)pyrimidin-2-yl)amino)-3-methoxyphenyl)-4-oxoadamantan-1-carboxamide

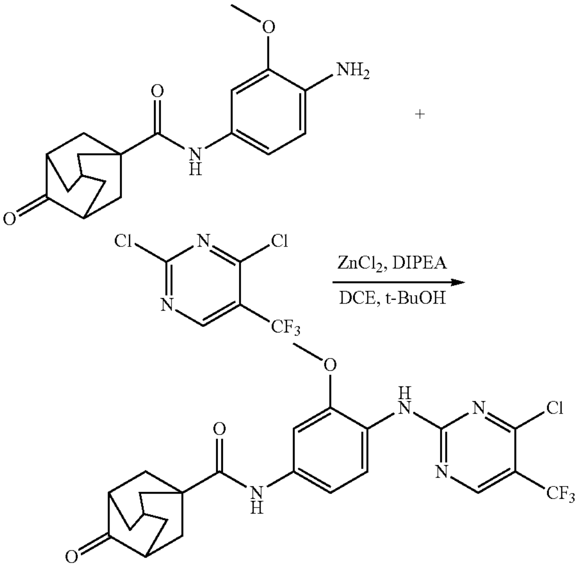

The title compound was synthesized in the same manner as in Example 1 by using N-(4-amino-3-methoxyphenyl)-4-oxoadamantan-1-carboxamide instead of (trans)-4-((4-amino-3-methoxyphenyl)amino) adamantan-1-ol in step 3 of Example 1.

[Step 4] Preparation of N-(3-methoxy-4-((4-((2-methyl-6-(methylcarbamoyl)phenyl)amino)-5-(trifluoromethyl)pyrimidin-2-yl)amino)phenyl)-4-oxoadamantan-1-carboxamide

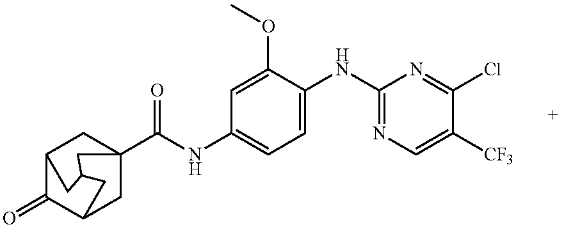

-continued

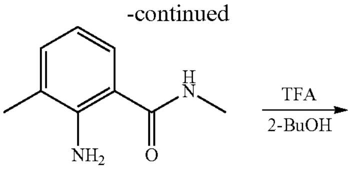

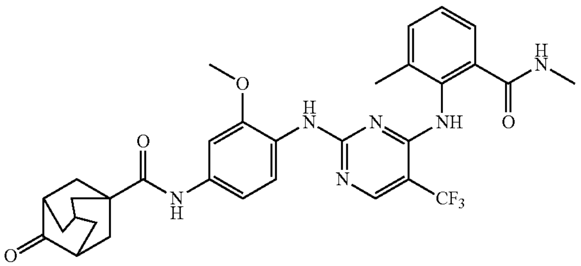

The title compound was synthesized in the same manner as in Example 1 by using N-(4-((4-chloro-5-(trifluoromethyl)pyrimidin-2-yl)amino)-3-methoxyphenyl)-4-oxoadamantan-1-carboxamide instead of (trans)-4-((4-((4-chloro-5-(trifluoromethyl)pyrimidin-2-yl)amino)-3-methoxyphenyl)amino) adamantan-1-ol in step 4 of Example 1.

[Step 5] Preparation of N-(3-methoxy-4-((4-((2-methyl-6-(methylcarbamoyl)phenyl)amino)-5-(trifluoromethyl)pyrimidin-2-yl)amino)phenyl)-4-morpholinoadamantan-1-carboxamide The title compound was synthesized in the same manner as in Example 12 by using N-(3-methoxy-4-((4-((2-methyl-6-(methylcarbamoyl)phenyl)amino)-5-(trifluoromethyl)pyrimidin-2-yl)amino)phenyl)-4-oxoadamantan-1-carboxamide instead of 2-((2-((2-methoxy-4-((4-oxoadamantan-1-yl)oxy)phenyl)amino)-5-(trifluoromethyl)pyrimidin-4-yl)amino)-N,3-dimethylbenzamide in step 1 of Example 12.

$^1$H NMR (400 MHz, $CDCl_3$): δ 8.40 (s, 1H), 8.29 (s, 1H), 7.69 (s, 1H), 7.53 (s, 1H), 7.41 (m, 2H), 7.32 (t, J=7.9 Hz, 1H), 7.19 (s, 1H), 6.34 (s, 1H), 6.01 (s, 1H), 3.86 (s, 3H), 3.75 (m, 4H), 2.88 (m, 3H), 2.45 (s, 3H), 2.21 (s, 3H), 2.16-2.01 (m, 6H), 1.93 (m, 4H), 1.58 (s, 3H), 1.40 (m, 2H)

<Example 26> Preparation of N-(3-methoxy-4-((4-((2-methyl-6-(methylcarbamoyl)phenyl)amino)-5-(trifluoromethyl)pyrimidin-2-yl)amino)phenyl)-4-(4-methylpiperazin-1-yl) adamantan-1-carboxamide (compound 26)

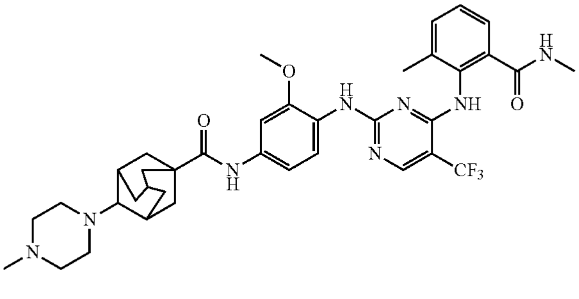

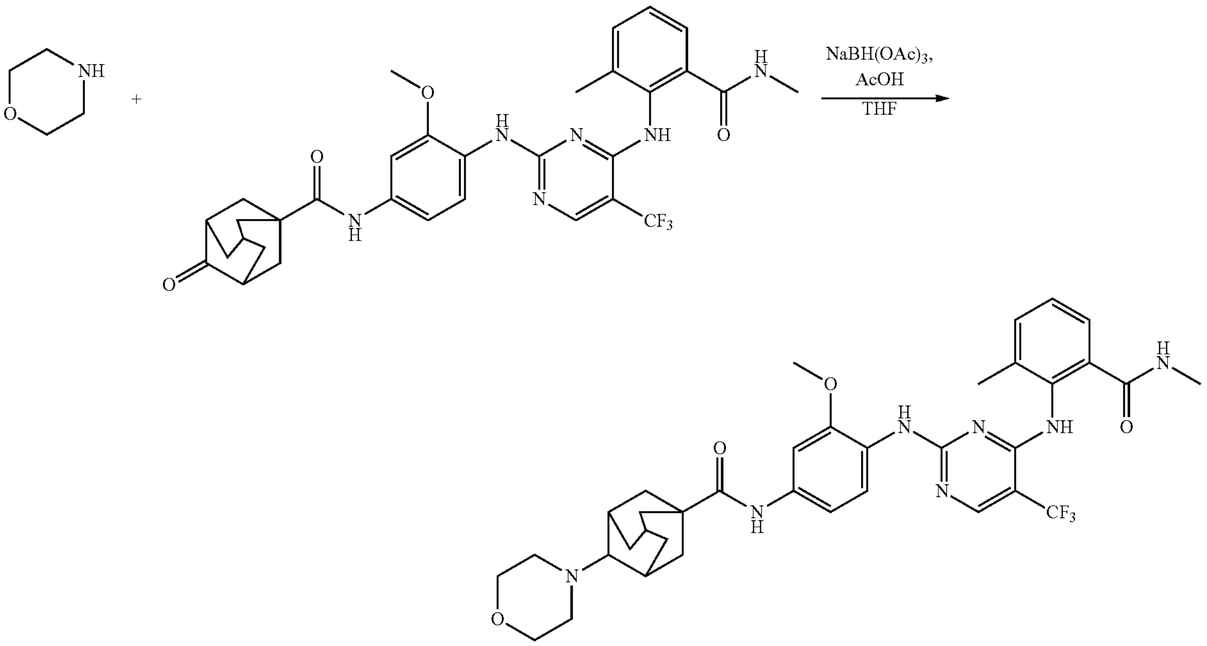

[Step 1] Preparation of N-(3-methoxy-4-((4-((2-methyl-6-(methylcarbamoyl)phenyl)amino)-5-(trifluoromethyl)pyrimidin-2-yl)amino)phenyl)-4-(4-methylpiperazin-1-yl) adamantan-1-carboxamide

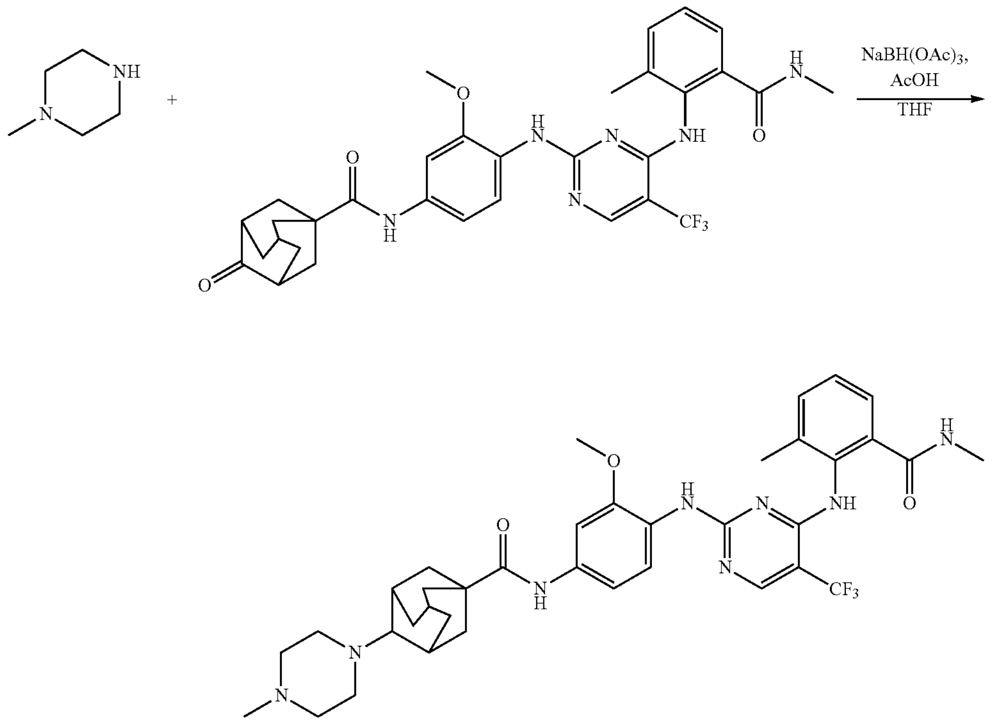

The title compound was synthesized in the same manner as in Example 25 by using 4-methylpiperazine instead of morpholine in step 5 of Example 25.

$^1$H NMR (400 MHz, $CDCl_3$): δ 8.39 (s, 1H), 8.29 (s, 1H), 7.69 (s, 1H), 7.53 (s, 1H), 7.40 (m, 2H), 7.35-7.29 (m, 1H), 7.18 (s, 1H), 6.34 (s, 1H), 6.00 (s, 1H), 3.86 (s, 3H), 2.87 (d, J=4.8 Hz, 3H), 2.48 (s, 4H), 2.30 (s, 3H), 2.24 (s, 1H), 2.21 (s, 3H), 2.07 (m, 5H), 1.92 (m, 3H), 1.68 (s, 7H), 1.38 (m, 2H)

<Example 27> Preparation of (trans)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide (compound 27)

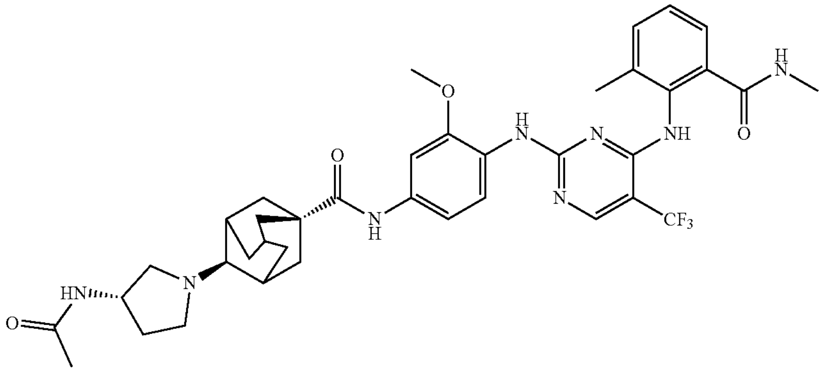 [SMILES: CNC(=O)c1cccc(C)c1Nc1nc(Nc2ccc(NC(=O)[C@]34CC5CC(C3)[C@@H](N3CC[C@H](NC(C)=O)C3)C(C5)C4)cc2OC)ncc1C(F)(F)F]

[Step 1] Preparation of (trans)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide

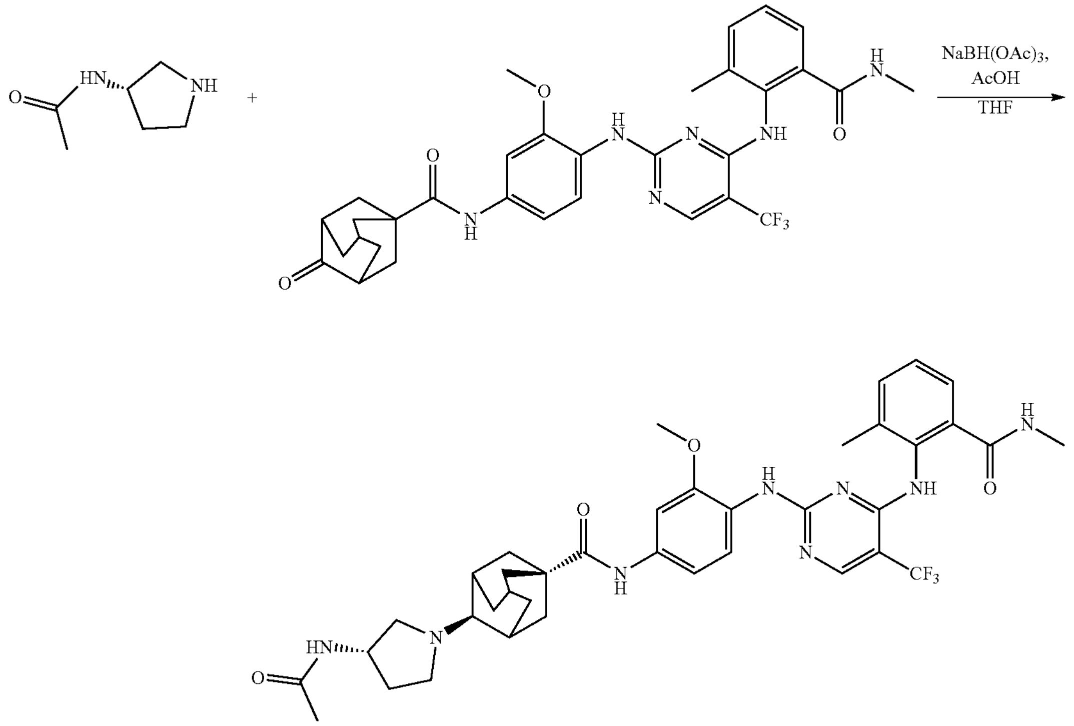

The title compound was synthesized in the same manner as in Example 25 by using (S)-N-(pyrrolidin-3-yl)acetamide instead of morpholine in step 5 of Example 25.

$^1$H NMR (400 MHz, $CDCl_3$): δ 8.45 (s, ill), 8.28 (s, ill), 7.69 (s, ill), 7.52 (s, 1H), 7.46-7.28 (m, 4H), 6.23 (s, 1H), 6.06 (s, 1H), 4.59 (s, 1H), 3.85 (s, 3H), 2.85 (d, J=4.7 Hz, 3H), 2.46 (m, 4H), 2.26-2.08 (m, 6H), 2.09-1.83 (m, 12H), 1.71 (m, 5H)

<Example 28> Preparation of (cis)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide (compound 28)

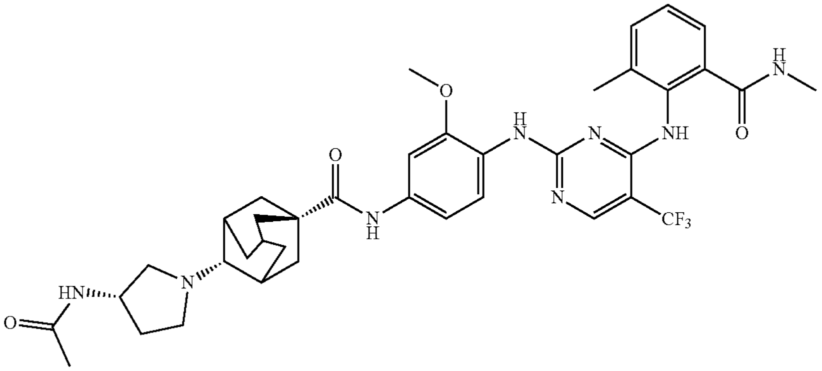 [SMILES: CNC(=O)c1cccc(C)c1Nc1nc(Nc2ccc(NC(=O)[C@]34CC5CC(C3)[C@H](N3CC[C@H](NC(C)=O)C3)C(C5)C4)cc2OC)ncc1C(F)(F)F]

[Step 1] Preparation of (cis)-4-((S)-3-acetamidopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide

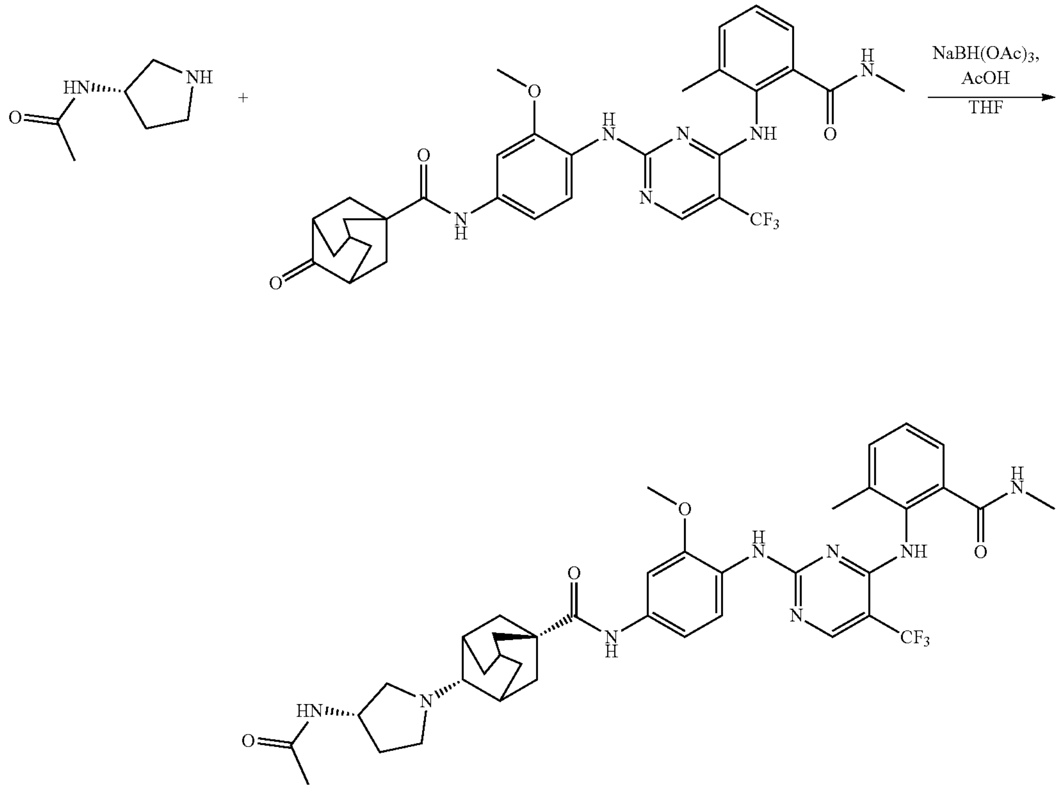

The title compound was synthesized in the same manner as in Example 25 by using (S)-N-(pyrrolidin-3-yl)acetamide instead of morpholine in step 5 of Example 25.

$^1$H NMR (400 MHz, $CDCl_3$): δ 8.43 (s, 1H), 8.29 (s, 1H), 7.69 (s, 1H), 7.50 (s, 1H), 7.40 (m, 2H), 7.31 (t, J=7.4 Hz, 1H), 7.20 (s, 1H), 6.35 (s, 1H), 6.07 (d, J=5.0 Hz, $^1$H), 4.49 (s, 1H), 3.86 (s, 3H), 2.87 (d, J=4.9 Hz, 3H), 2.55 (s, 1H), 2.29 (s, 1H), 2.24-1.87 (m, 17H), 1.70 (s, 6H), 1.45 (d, 2H)

<Example 29> Preparation of 4-hydroxy-N-(3-methoxy-4-((4-((2-methyl-6-(methylcarbamoyl)phenyl)amino)-5-(trifluoromethyl)pyrimidin-2-yl)amino)phenyl) adamantan-1-carboxamide (compound 29)

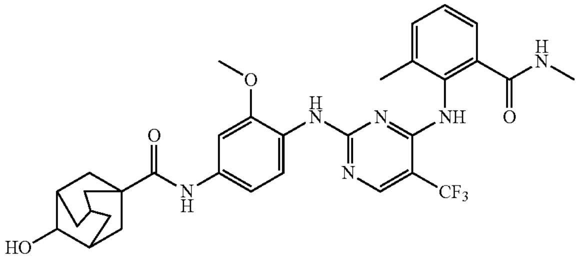 [SMILES: CNC(=O)c1cccc(C)c1Nc1nc(Nc2ccc(NC(=O)C34CC5CC(C3)C(O)C(C5)C4)cc2OC)ncc1C(F)(F)F]

[Step 1] Preparation of 4-hydroxy-N-(3-methoxy-4-((4-((2-methyl-6-(methylcarbamoyl)phenyl)amino)-5-(trifluoromethyl)pyrimidin-2-yl)amino)phenyl) adamantan-1-carboxamide

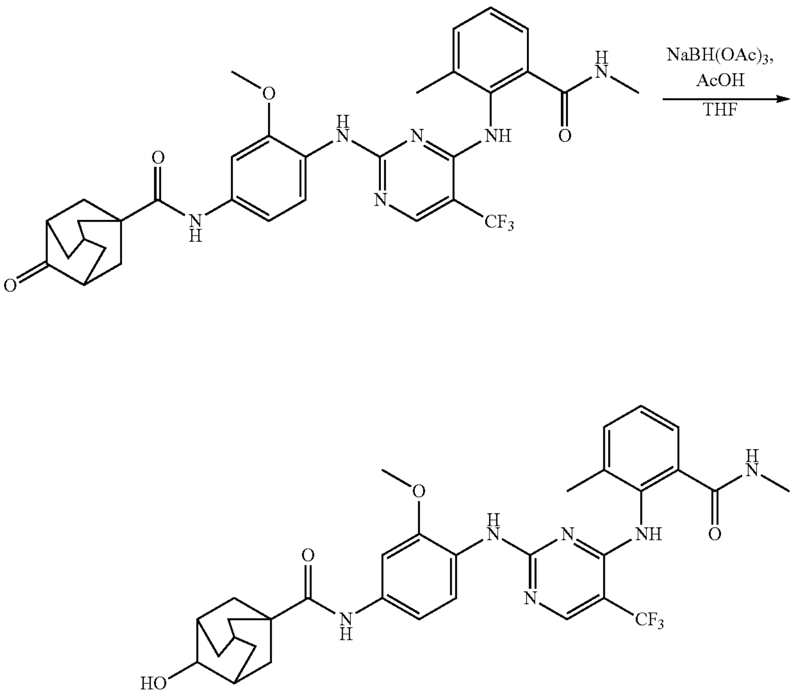

The title compound was synthesized in the same manner as in Example 11 by using N-(3-methoxy-4-((4-((2-methyl-6-(methylcarbamoyl)phenyl)amino)-5-(trifluoromethyl)pyrimidin-2-yl)amino)phenyl)-4-oxoadamantan-1-carboxamide instead of 2-((2-((2-methoxy-4-((4-oxoadamantan-1-yl)oxy)phenyl)amino)-5-(trifluoromethyl)pyrimidin-4-yl)amino)-N,3-dimethylbenzamide in step 1 of Example 11.

$^1$H NMR (400 MHz, DMSO-$d_6$): δ 9.10 (s, 1H), 8.96-8.85 (m, 1H), 8.27-8.20 (m, 2H), 7.90 (s, 1H), 7.41-7.23 (m, 5H), 6.86 (br s, 1H), 4.59 (m, 1H), 3.69 (s, 3H), 3.68-3.54 (m, 1H), 2.63 (d, J=4.5, 3H), 2.15-1.96 (m, 5H), 1.88-1.74 (m, 7H), 1.68 (m, 1H), 1.56 (m, 1H), 1.35-1.27 (m, 2H)

<Example 30> Preparation of (trans)-4-((S)-3-aminopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide (compound 30)

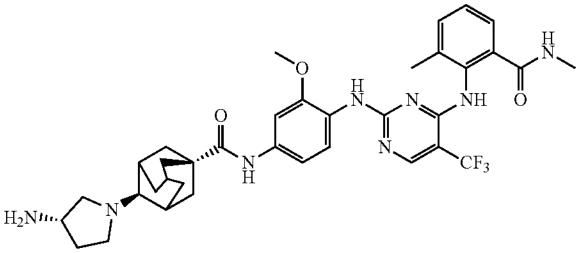 [SMILES: CNC(=O)c1cccc(C)c1Nc1nc(Nc2ccc(NC(=O)[C@]34CC5CC(C3)[C@@H](N3CC[C@H](N)C3)C(C5)C4)cc2OC)ncc1C(F)(F)F]

[Step 1] Preparation of tert-butyl ((3S)-1-((trans)-5-((3-methoxy-4-((4-((2-methyl-6-(methylcarbamoyl)phenyl)amino)-5-(trifluoromethyl)pyrimidin-2-yl)amino)phenyl)carbamoyl) adamantan-2-yl) pyrrolidin-3-yl)carbamate

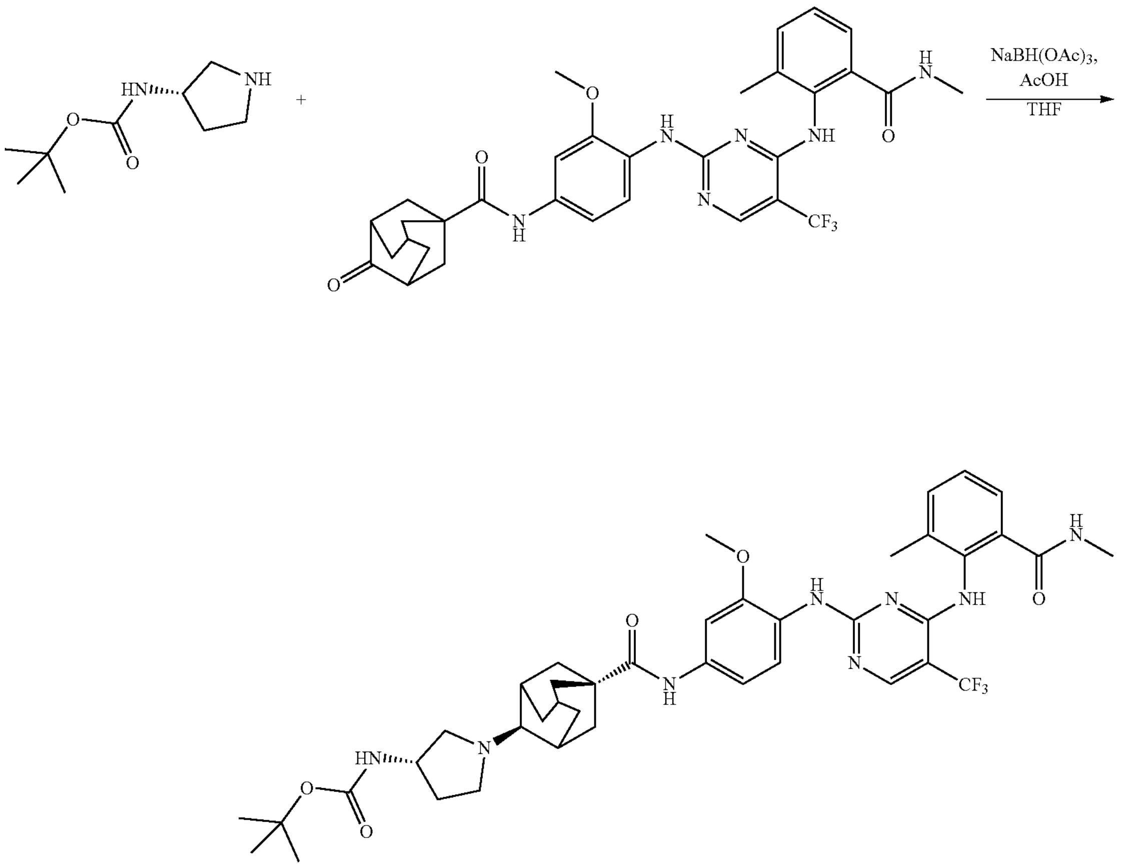

The title compound was synthesized in the same manner as in Example 25 by using tert-butyl (S)-pyrrolidin-3-ylcarbamate instead of morpholine in step 5 of Example 25.

[Step 2] Preparation of (trans)-4-((S)-3-aminopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide

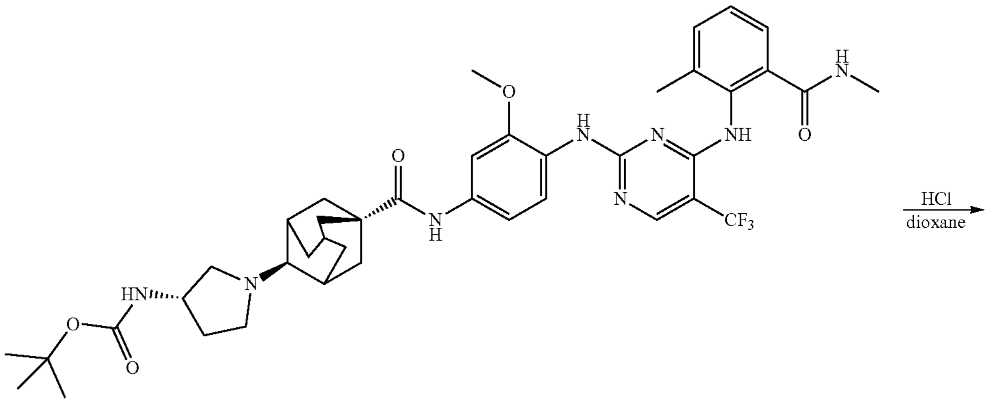

-continued

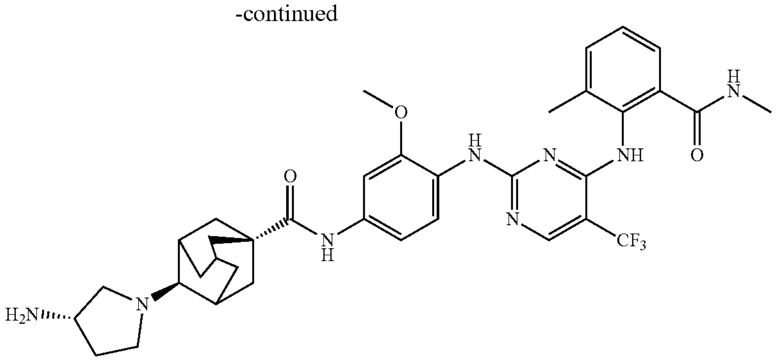

tert-Butyl ((3S)-1-((trans)-5-((3-methoxy-4-((4-((2-methyl-6-(methylcarbamoyl)phenyl)amino)-5-(trifluoromethyl)pyrimidin-2-yl)amino)phenyl)carbamoyl) adamantan-2-yl)pyrrolidin-3-yl)carbamate prepared in above step 1 was dissolved in 4 M hydrochloric acid dioxane solution and stirred at room temperature. After completion of the reaction was confirmed by TLC, a saturated aqueous solution of $NaHCO_3$ was added to the reaction solution, followed by extraction with ethyl acetate. The resulting solution was dried over anhydrous magnesium sulfate, and filtered, after which the filtrate was concentrated and purified by column chromatography to obtain the title compound.

$^1H$ NMR (400 MHz, $CDCl_3$): δ 8.46 (s, 1H), 8.30 (s, 1H), 7.70 (s, 1H), 7.53 (s, 1H), 7.46-7.20 (m, 4H), 6.37 (m, 1H), 6.14 (m, 1H), 3.52 (s, 1H), 3.86 (s, 3H), 2.87 (d, J=4.8 Hz, 3H), 2.85-1.25 (m, 24H)

<Example 31> Preparation of (cis)-4-((S)-3-amino-pyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide (compound 31)

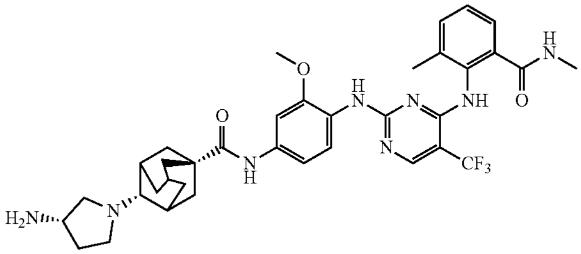

[Step 1] Preparation of tert-butyl ((3S)-1-((trans)-5-((3-methoxy-4-((4-((2-methyl-6-(methylcarbamoyl)phenyl)amino)-5-(trifluoromethyl)pyrimidin-2-yl)amino)phenyl)carbamoyl) adamantan-2-yl) pyrrolidin-3-yl)carbamate

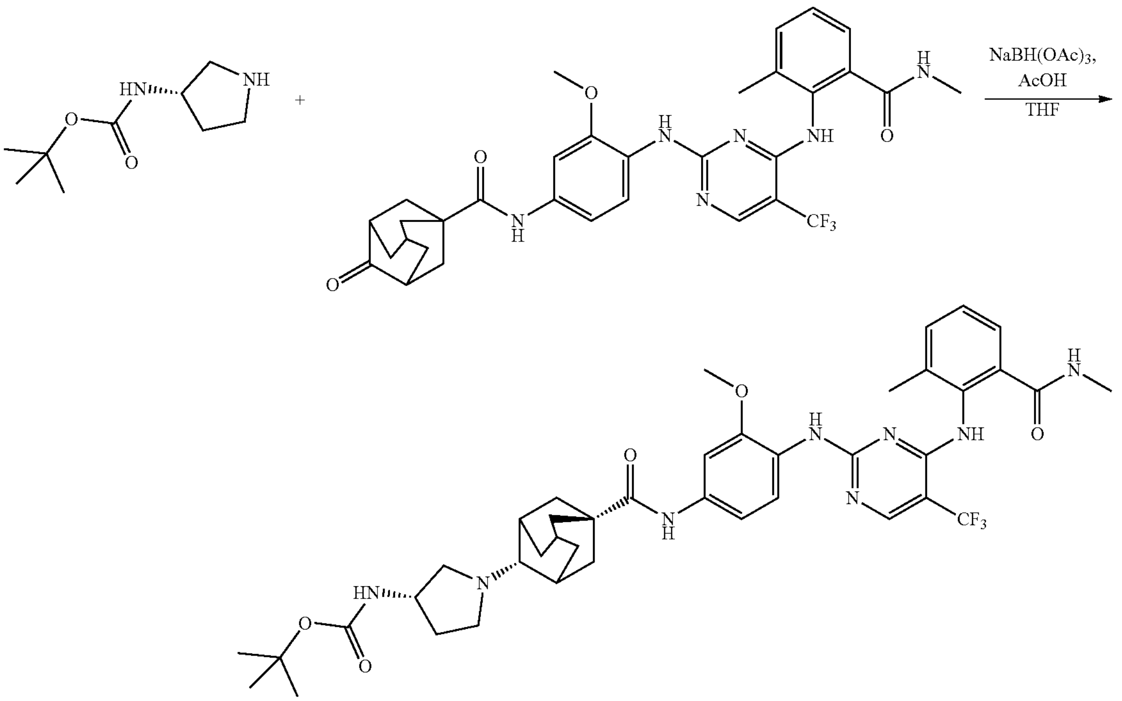

The title compound was synthesized in the same manner as in Example 25 by using tert-butyl (S)-pyrrolidin-3-ylcarbamate instead of morpholine in step 5 of Example 25.

[Step 2] Preparation of (cis)-4-((S)-3-aminopyrrolidin-1-yl)-N-(3-methoxy-4-((4-((2-methyl-6-(methylcarbamoyl)phenyl)amino)-5-(trifluoromethyl)pyrimidin-2-yl)amino)phenyl) adamantan-1-carboxamide

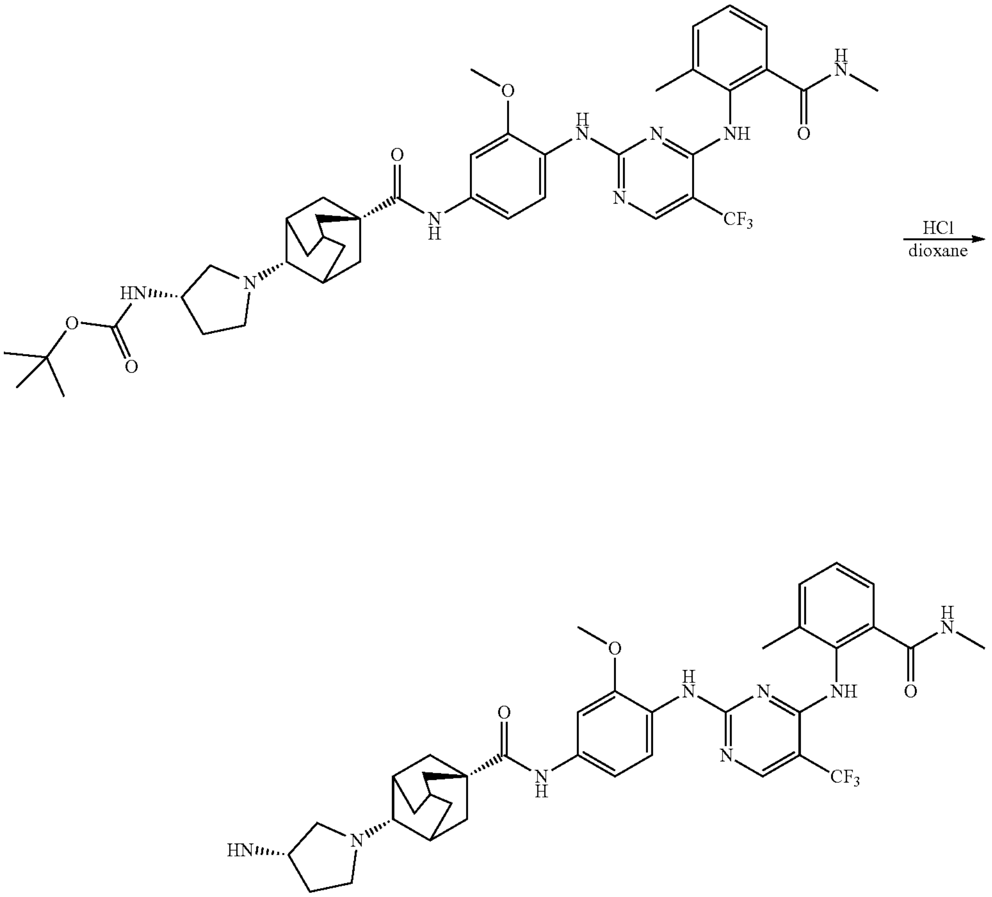

tert-Butyl ((3S)-1-((cis)-5-((3-methoxy-4-((4-((2-methyl-6-(methylcarbamoyl)phenyl)amino)-5-(trifluoromethyl)pyrimidin-2-yl)amino)phenyl)carbamoyl) adamantan-2-yl) pyrrolidin-3-yl)carbamate prepared in above step 1 was dissolved in 4 M hydrochloric acid dioxane solution and stirred at room temperature. After completion of the reaction was confirmed by TLC, a saturated aqueous solution of $NaHCO_3$ was added to the reaction solution, followed by extraction with ethyl acetate. The resulting solution was dried over anhydrous magnesium sulfate, and filtered, after which the filtrate was concentrated and purified by column chromatography to obtain the title compound.

$^1$H NMR (400 MHz, $CDCl_3$): δ 8.45 (s, 1H), 8.29 (s, 1H), 7.70 (s, 1H), 7.53 (s, 1H), 7.46-7.20 (m, 4H), 6.36 (m, 1H), 6.14 (m, 1H), 3.52 (s, 1H), 3.86 (s, 3H), 2.87 (d, J=4.8 Hz, 3H), 2.85-1.25 (m, 24H)

<Example 32> Preparation of 2-((2-((4-(1-((trans)-5-hydroxyadamantan-2-yl)piperidin-4-yl)-2-methoxyphenyl)amino)-5-(trifluoromethyl)pyrimidin-4-yl)amino)-N,3-dimethylbenzamide (compound 32)

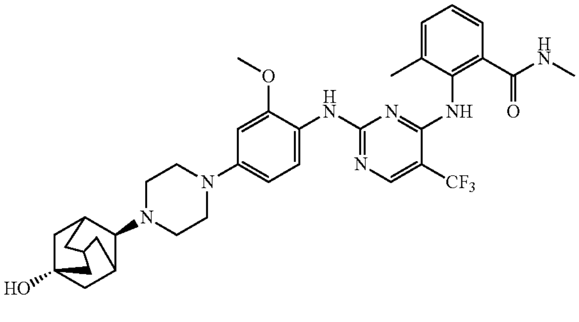 [SMILES: CNC(=O)c1cccc(C)c1Nc1nc(Nc2ccc(N3CCN([C@H]4C5CC6CC4C[C@](O)(C6)C5)CC3)cc2OC)ncc1C(F)(F)F]

[Step 1] Preparation of 2-((2-((4-(1-((trans)-5-hydroxyadamantan-2-yl)piperidin-4-yl)-2-methoxyphenyl)amino)-5-(trifluoromethyl)pyrimidin-4-yl) amino)-N,3-dimethylbenzamide

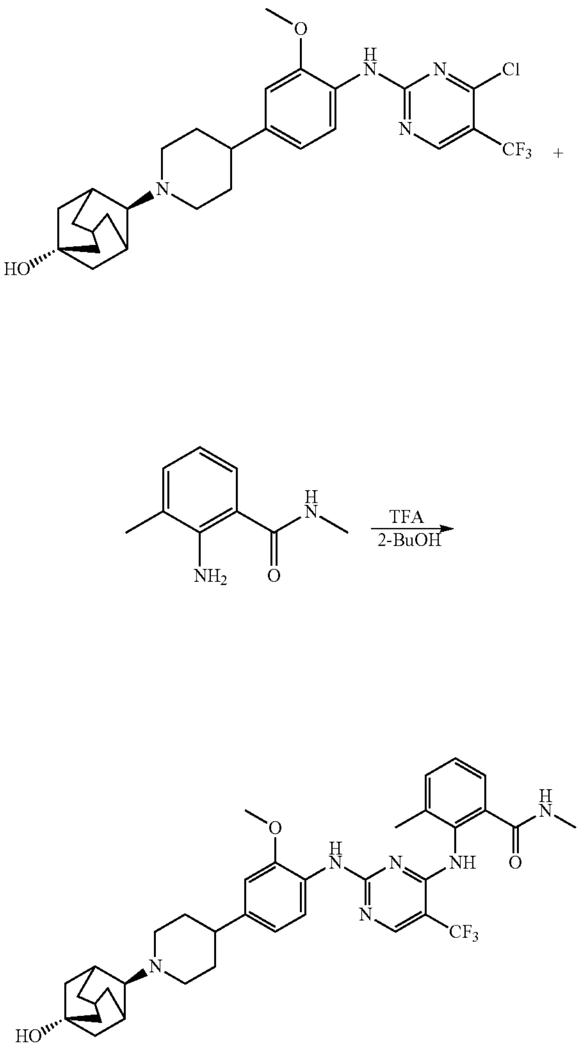

The title compound was synthesized in the same manner as in Example 1 by using (trans)-4-(4-(4-((4-chloro-5-(trifluoromethyl)pyrimidin-2-yl)amino)-3-methoxyphenyl)piperidin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.38 (s, 1H), 8.29 (s, 1H), 7.69 (br s, 1H), 7.46-7.28 (m, 3H), 6.70 (d, J=7.0 Hz, 1H), 6.41 (br s, 1H), 6.06 (br s, 1H), 5.98 (s, 1H), 3.85 (s, 3H), 3.09 (m, 2H), 2.89 (m, 2H), 2.86 (d, J=4.9 Hz, 3H), 2.72-2.59 (m, 2H), 2.53 (m, 1H), 2.37 (m, 1H), 2.31 (m, 1H), 2.24 (m, 1H), 2.22 (s, 3H), 2.13-1.20 (m, 13H)

<Example 33> Preparation of 2-((2-((4-(1-((cis)-5-hydroxyadamantan-2-yl)piperidin-4-yl)-2-methoxyphenyl)amino)-5-(trifluoromethyl)pyrimidin-4-yl) amino)-N,3-dimethylbenzamide (compound 33)

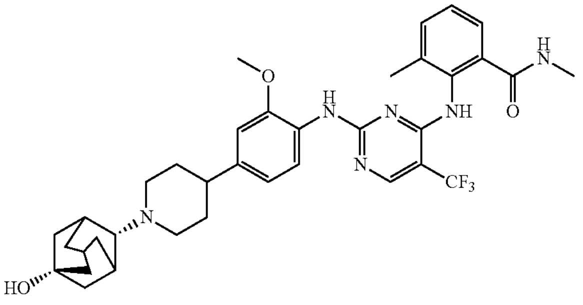 [SMILES: CNC(=O)c1cccc(C)c1Nc1nc(Nc2ccc(C3CCN([C@H]4C5CC6CC4C[C@@](O)(C6)C5)CC3)cc2OC)ncc1C(F)(F)F]

[Step 1] Preparation of 2-((2-((4-(1-((cis)-5-hydroxyadamantan-2-yl)piperidin-4-yl)-2-methoxyphenyl)amino)-5-(trifluoromethyl)pyrimidin-4-yl) amino)-N,3-dimethylbenzamide

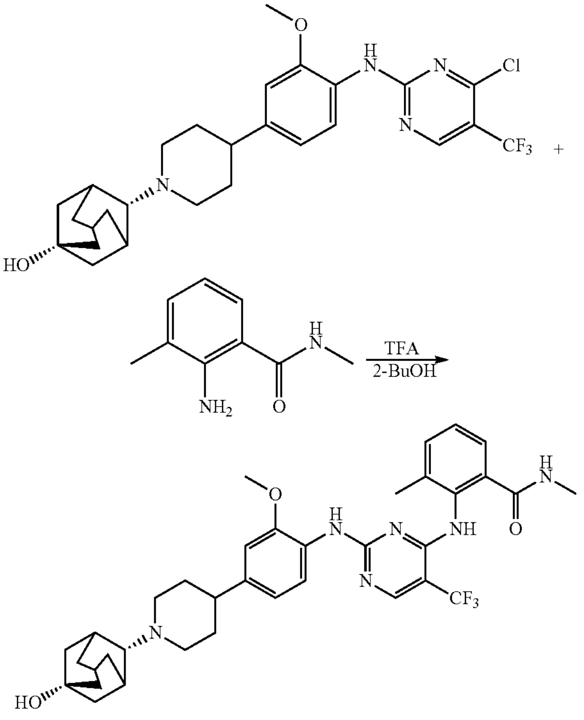

The title compound was synthesized in the same manner as in Example 1 by using (cis)-4-(4-(4-((4-chloro-5-(trifluoromethyl)pyrimidin-2-yl)amino)-3-methoxyphenyl)piperidin-1-yl) adamantan-1-ol instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.38 (s, 1H), 8.29 (s, 1H), 7.69 (br s, 1H), 7.46-7.28 (m, 3H), 6.70 (d, J=7.0 Hz, 1H), 6.41 (br s, 1H), 6.06 (br s, 1H), 5.99 (s, 1H), 3.85 (s, 3H), 3.09 (m, 2H), 2.89 (m, 2H), 2.87 (d, J=4.9 Hz, 3H), 2.72-2.59 (m, 2H), 2.53 (m, 1H), 2.38 (m, 1H), 2.31 (m, 1H), 2.24 (m, 1H), 2.21 (s, 3H), 2.13-1.20 (m, 13H)

<Example 34> Preparation of 2-((2-((4-(1-((trans)-5-hydroxyadamantan-2-yl)piperidin-4-yl)-2-methoxyphenyl)amino)-5-(trifluoromethyl)pyrimidin-4-yl)amino)-3-methylbenzamide (compound 34)

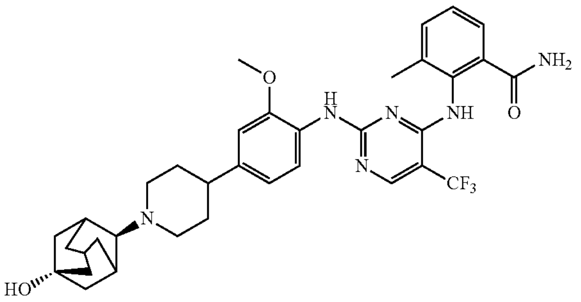 [SMILES: COc1cc(C2CCN([C@H]3C4CC5CC3C[C@](O)(C5)C4)CC2)ccc1Nc1ncc(C(F)(F)F)c(Nc2c(C)cccc2C(N)=O)n1]

[Step 1] Preparation of 2-((2-((4-(1-((trans)-5-hydroxyadamantan-2-yl)piperidin-4-yl)-2-methoxyphenyl)amino)-5-(trifluoromethyl)pyrimidin-4-yl)amino)-3-methylbenzamide

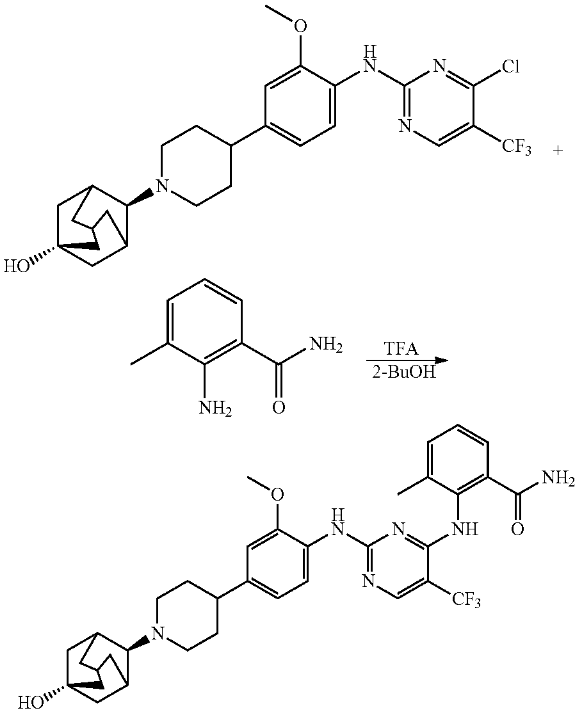

The title compound was synthesized in the same manner as in Example 32 by using 2-amino-3-methylbenzamide instead of 2-amino-N,3-dimethylbenzamide in step 1 of Example 32.

$^1$H NMR (400 MHz, $CDCl_3$): δ 8.39 (s, 1H), 8.30 (s, 1H), 7.70 (br s, 1H), 7.54-7.43 (m, 2H), 7.35 (m, 1H), 6.70 (s, 1H), 6.41 (br s, 1H), 6.04 (br s, 1H), 5.57 (s, 1H), 3.85 (s,

3H), 3.09 (m, 2H), 2.87 (m, 2H), 2.63 (m, 2H), 2.53 (m, 1H), 2.37 (m, 1H), 2.31 (m, 1H), 2.23 (s, 3H), 2.13-1.20 (m, 14H)

<Example 35> Preparation of 2-((2-((4-(1-((cis)-5-hydroxyadamantan-2-yl)piperidin-4-yl)-2-methoxyphenyl)amino)-5-(trifluoromethyl)pyrimidin-4-yl)amino)-3-methylbenzamide (compound 35)

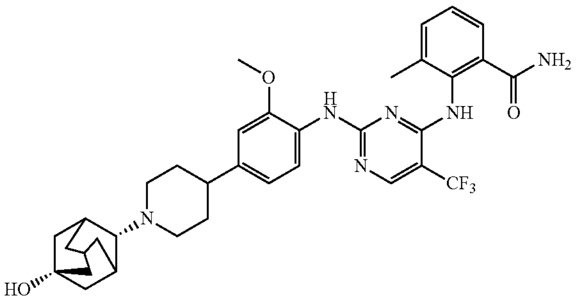 [SMILES: COc1cc(C2CCN([C@H]3C4CC5CC3C[C@@](O)(C5)C4)CC2)ccc1Nc1ncc(C(F)(F)F)c(Nc2c(C)cccc2C(N)=O)n1]

[Step 1] Preparation of 2-((2-((4-(1-((cis)-5-hydroxyadamantan-2-yl)piperidin-4-yl)-2-methoxyphenyl)amino)-5-(trifluoromethyl)pyrimidin-4-yl)amino)-3-methylbenzamide

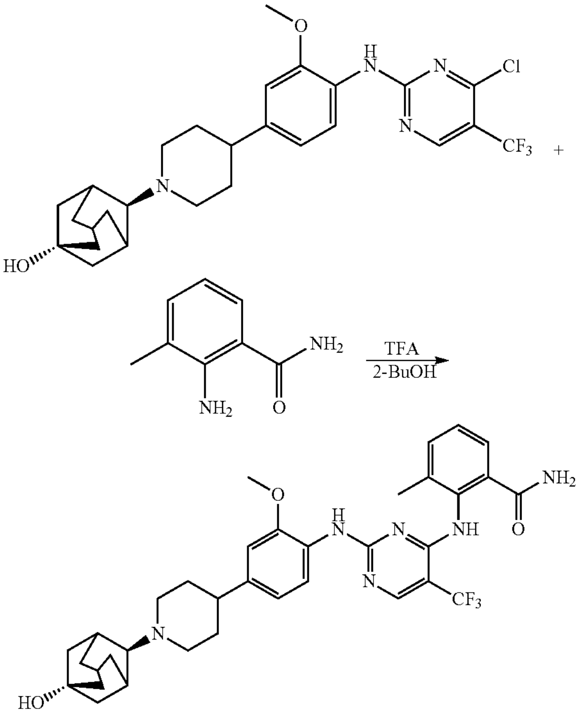

The title compound was synthesized in the same manner as in Example 33 by using 2-amino-3-methylbenzamide instead of 2-amino-N,3-dimethylbenzamide in step 1 of Example 33.

$^1$H NMR (400 MHz, $CDCl_3$): δ 8.41 (s, 1H), 8.30 (s, 1H), 7.70 (br s, 1H), 7.53-7.44 (m, 2H), 7.35 (t, J=7.6 Hz, 1H), 6.69 (s, 1H), 6.41 (br s, 1H), 6.03 (br s, 1H), 5.59 (s, 1H), 3.85 (s, 3H), 3.09 (m, 2H), 2.87 (m, 2H), 2.63 (m, 2H), 2.53 (m, 1H), 2.37 (m, 1H), 2.31 (m, 1H), 2.23 (s, 3H), 2.13-1.20 (m, 14H)

<Example 36> Preparation of 2-((5-chloro-2-((4-(4-((trans)-5-hydroxyadamantan-2-yl)piperazin-1-yl)-2-methoxyphenyl)amino)-pyrimidin-4-yl)amino)-N,3-dimethylbenzamide (compound 36)

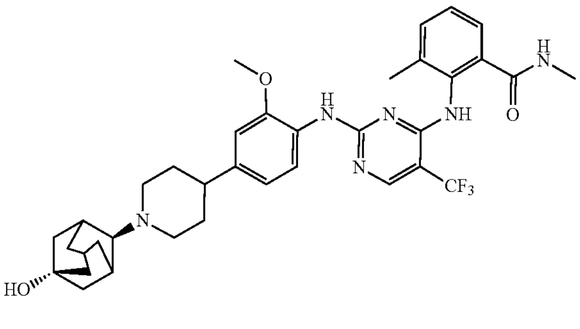 [SMILES: CNC(=O)c1cccc(C)c1Nc1nc(Nc2ccc(C3CCN([C@H]4C5CC6CC4C[C@](O)(C6)C5)CC3)cc2OC)ncc1C(F)(F)F]

[Step 1] Preparation of 2-((2,5-dichloropyrimidin-4-yl)amino)-N,3-dimethylbenzamide

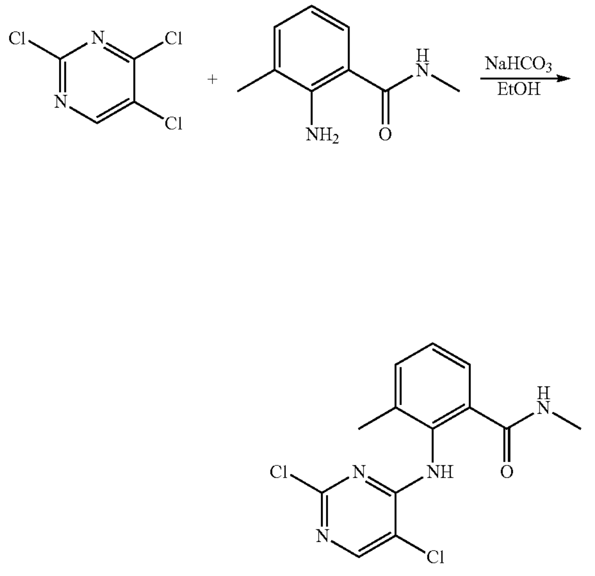

After dissolving 2-amino-N,3-dimethylbenzamide and $NaHCO_3$ in ethanol, 2,4,5-trichloropyrimidine was added and stirred at 80° C. After completion of the reaction was confirmed by TLC, a solvent was concentrated, and the resulting solid was dissolved in ethyl acetate and wiped with distilled water. The resulting solution was dried over anhydrous magnesium sulfate, and filtered, after which the filtrate was concentrated and recrystallized with acetonitrile: distilled water=20: 1 to obtain the title compound.

[Step 2] Preparation of 2-((5-chloro-2-((4-(4-((trans)-5-hydroxyadamantan-2-yl)piperazin-1-yl)-2-methoxyphenyl)amino)-pyrimidin-4-yl)amino)-N,3-dimethylbenzamide

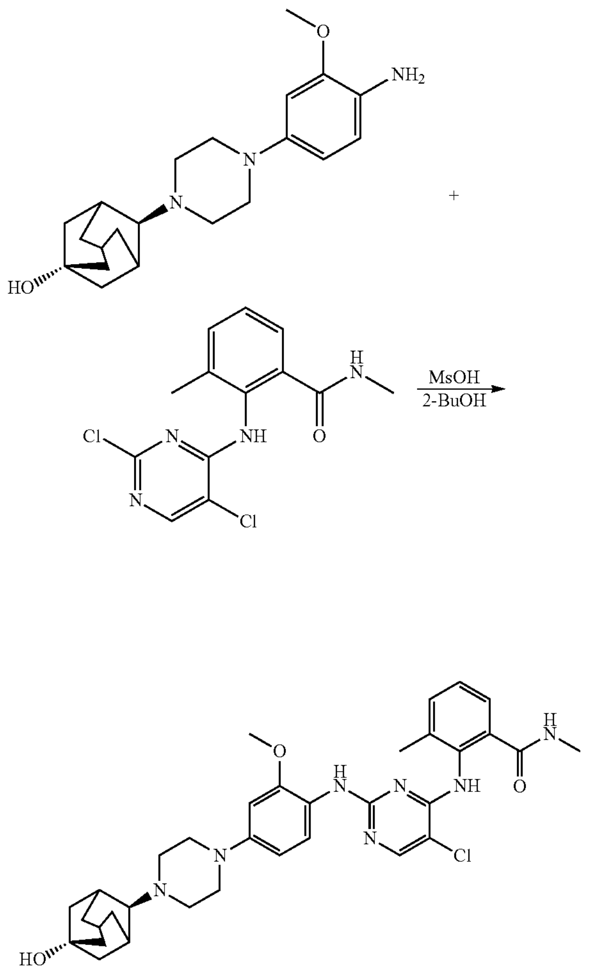

4-(4-(4-Amino-3-methoxyphenyl)piperazin-1-yl) adamantan-1-ol and 2-((2,5-dichloropyrimidin-4-yl)amino)-N, 3-dimethylbenzamide prepared in above step 1 were dissolved in 2-butanol, after which methanesulfonic acid was added and stirred at 120° C. After completion of the reaction, distilled water was added to the reaction solution, followed by extraction with ethyl acetate. The resulting solution was dried over anhydrous magnesium sulfate, and filtered, after which the filtrate was concentrated and purified by column chromatography to obtain the title compound.

$^1$H NMR (400 MHz, $CDCl_3$): δ 8.66 (s, 1H), 8.01 (s, 1H), 7.67 (m, 2H), 7.45-7.16 (m, 5H), 6.48 (m, 2H), 6.18 (m, 1H), 6.07 (br s, 1H), 3.81 (s, 3H), 3.09 (m, 4H), 2.87 (d, J=4.8 Hz, 3H), 2.62 (m, 4H), 2.34-2.26 (m, 1H), 2.22 (s, 3H), 2.14-1.98 (m, 4H), 1.83-1.61 (m, 5H), 1.42-1.24 (m, 3H)

<Example 37> Preparation of methyl (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate (compound 37)

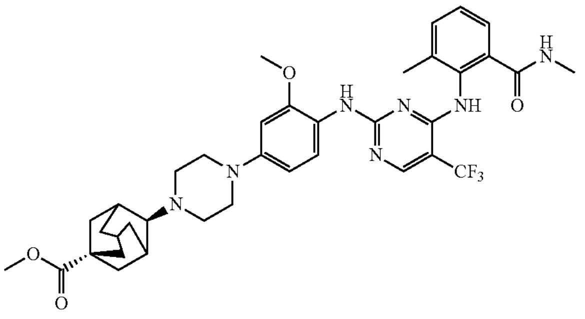

[Step 1] Preparation of methyl (trans)-4-(4-(4-((4-chloro-5-(trifluoromethyl)pyrimidin-2-yl)amino)-3-methoxyphenyl)piperazin-1-yl) adamantan-1-carboxylate

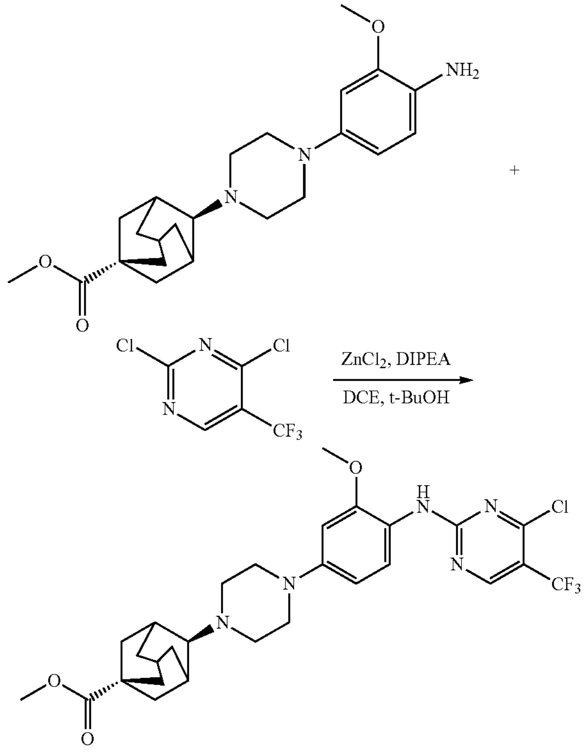

The title compound was synthesized in the same manner as in Example 1 by using methyl (trans)-4-(4-(4-amino-3-methoxyphenyl)piperazin-1-yl) adamantan-1-carboxylate instead of (trans)-4-((4-amino-3-methoxyphenyl)amino) adamantan-1-ol in step 3 of Example 1.

[Step 2] Preparation of methyl (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate

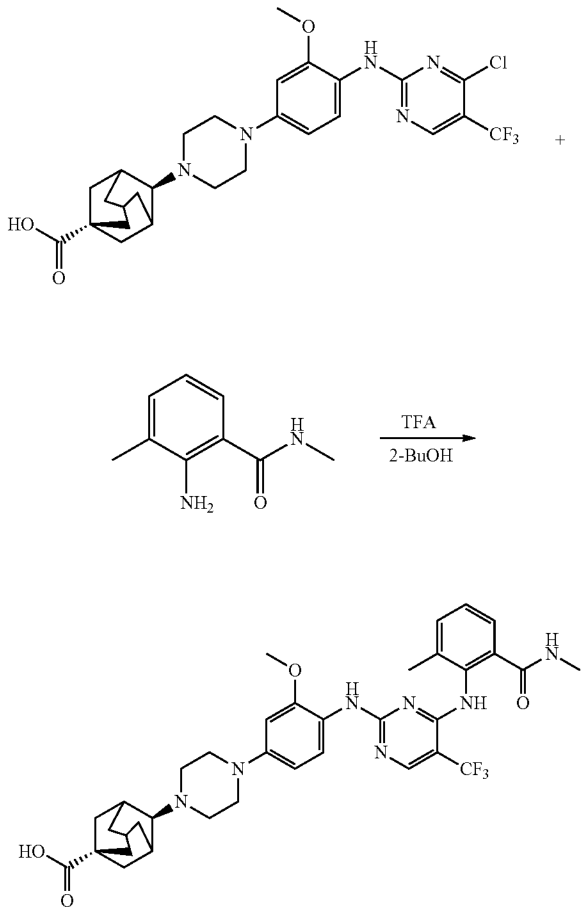

The title compound was synthesized in the same manner as in Example 1 by using methyl (trans)-4-(4-(4-((4-chloro-5-(trifluoromethyl)pyrimidin-2-yl)amino)-3-methoxyphenyl)piperazin-1-yl) adamantan-1-carboxylate instead of (trans)-4-((4-((4-chloro-5-(trifluoromethyl)pyrimidin-2-yl)amino)-3-methoxyphenyl)amino) adamantan-1-ol in step 4 of Example 1.

$^{1}$H NMR (400 MHz, $CDCl_3$): δ 8.28 (s, 1H), 8.26 (s, 1H), 7.40 (d, J=7.3 Hz, $^{1}$H), 7.36 (d, J=7.5 Hz, 1H), 7.31-7.26 (m, 1H), 6.47 (d, J=2.0 Hz, 1H), 6.15-5.95 (m, 2H), 3.82 (s, 3H), 3.66 (s, 3H), 3.09 (m, 4H), 2.84 (d, J=4.8 Hz, 3H), 2.60 (m, 4H), 2.25-2.14 (m, 4H), 2.13-2.05 (m, 2H), 2.04-1.92 (m, 2H), 1.91-1.82 (m, 3H), 1.73-1.62 (m, 2H), 1.40-1.33 (m, 2H), 1.31-1.20 (m, 2H)

<Example 38> Preparation of methyl (cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate (compound 38)

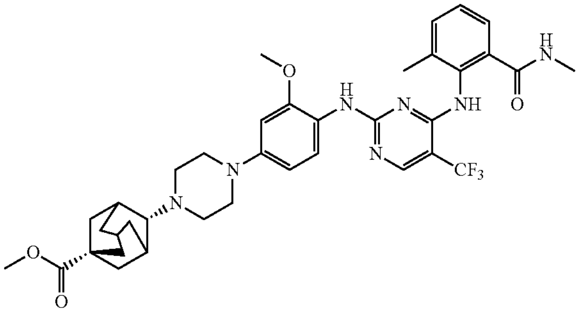

[Step 1] Preparation of methyl (cis)-4-(4-(4-((4-chloro-5-(trifluoromethyl)pyrimidin-2-yl)amino)-3-methoxyphenyl)piperazin-1-yl) adamantan-1-carboxylate

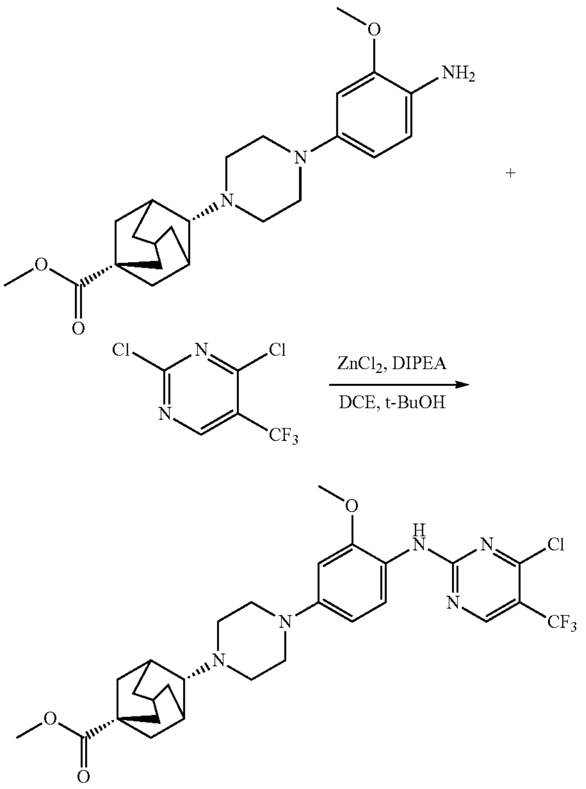

The title compound was synthesized in the same manner as in Example 1 by using methyl (cis)-4-(4-(4-amino-3-methoxyphenyl)piperazin-1-yl) adamantan-1-carboxylate instead of (trans)-4-((4-amino-3-methoxyphenyl)amino) adamantan-1-ol in step 3 of Example 1.

[Step 2] Preparation of methyl (cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate

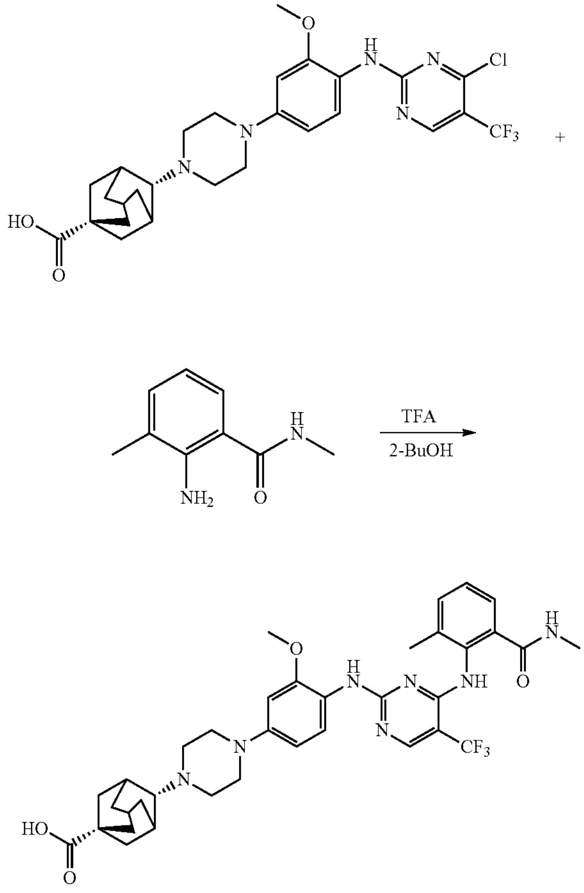

The title compound was synthesized in the same manner as in Example 1 by using methyl (cis)-4-(4-(4-((4-chloro-5-(trifluoromethyl)pyrimidin-2-yl)amino)-3-methoxyphenyl)piperazin-1-yl) adamantan-1-carboxylate instead of (trans)-4-((4-((4-chloro-5-(trifluoromethyl)pyrimidin-2-yl)amino)-3-methoxyphenyl)amino) adamantan-1-ol in step 4 of Example 1.

$^1$H NMR (400 MHz, $CDCl_3$): δ 8.27 (s, 1H), 8.26 (s, 1H), 7.41 (d, J=7.3 Hz, 1H), 7.37 (d, J=7.5 Hz, 1H), 7.31-7.26 (m, 1H), 6.47 (d, J=2.0 Hz, 1H), 6.15-5.95 (m, 2H), 3.82 (s, 3H), 3.66 (s, 3H), 3.09 (m, 4H), 2.84 (d, J=4.8 Hz, 3H), 2.60 (m, 4H), 2.28-2.13 (m, 5H), 2.07 (m, 1H), 1.98 (m, 1H), 1.90-1.77 (m, 4H), 1.75-1.48 (m, 6H)

<Example 39> Preparation of (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylic acid (compound 39)

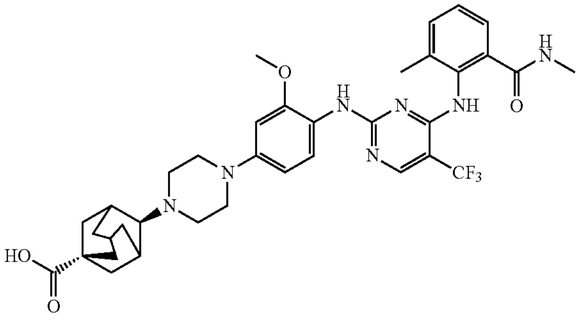 [SMILES: CNC(=O)c1cccc(C)c1Nc1nc(Nc2ccc(N3CCN([C@H]4C5CC6CC4C[C@](C(=O)O)(C6)C5)CC3)cc2OC)ncc1C(F)(F)F]

[Step 1] Preparation of (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylic acid

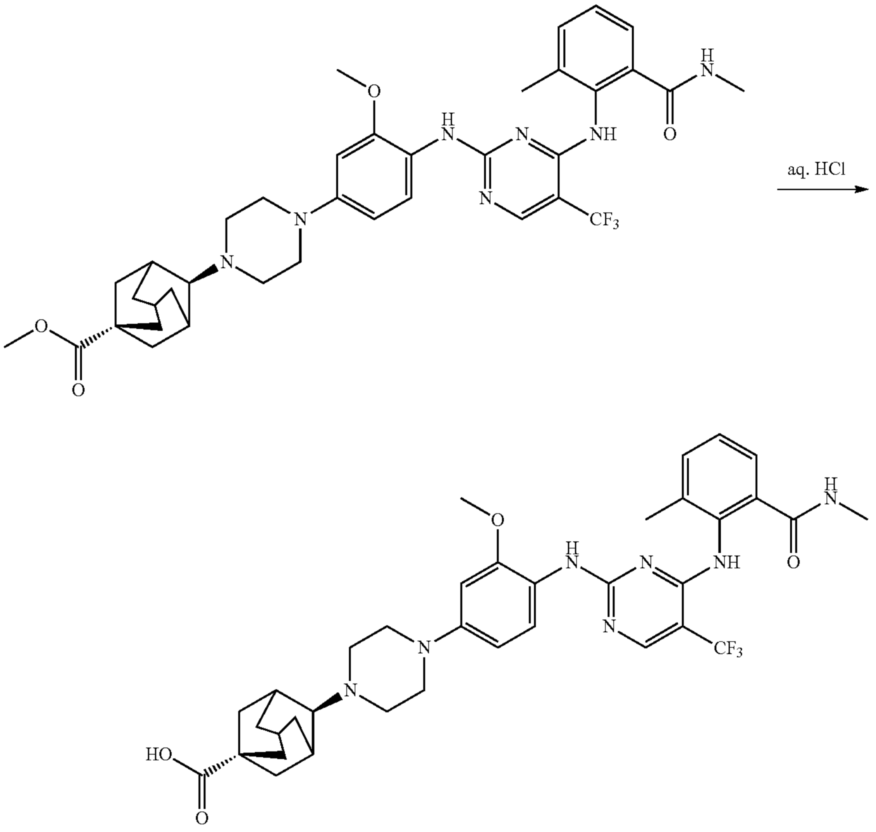

The title compound was synthesized in the same manner as in Example 17 by using methyl (trans)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate instead of 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate in step 1 of Example 17.

$^1$H NMR (400 MHz, $CD_3OD$): δ 8.20 (s, 1H), 7.48-7.32 (m, 3H), 6.56 (d, J=2.4 Hz, 1H), 6.12 (m, 2H), 3.83 (s, 3H), 3.13 (m, 4H), 2.79 (s, 3H), 2.71 (m, 4H), 2.30-2.22 (m, 3H), 2.21 (s, 3H), 2.15-2.08 (m, 2H), 2.06-1.99 (m, 2H), 1.96-1.84 (m, 5H), 1.48-1.40 (m, 2H)

<Example 40> Preparation of (cis)-4-(4-(3-methoxy-4-((4-((2-methyl-6-(methylcarbamoyl)phenyl)amino)-5-(trifluoromethyl)pyrimidin-2-yl) amino)phenyl)piperazin-1-yl) adamantan-1-carboxylic acid (compound 40)

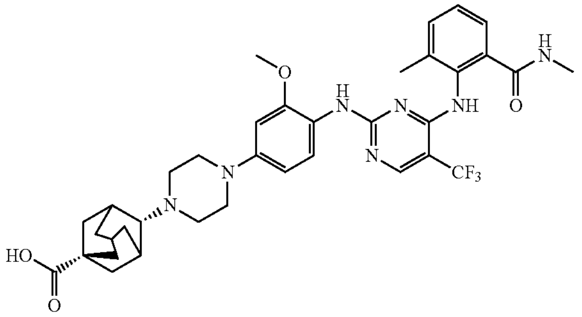 [SMILES: CNC(=O)c1cccc(C)c1Nc1nc(Nc2ccc(N3CCN([C@H]4C5CC6CC4C[C@](C(=O)O)(C6)C5)CC3)cc2OC)ncc1C(F)(F)F]

[Step 1] Preparation of (cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylic acid

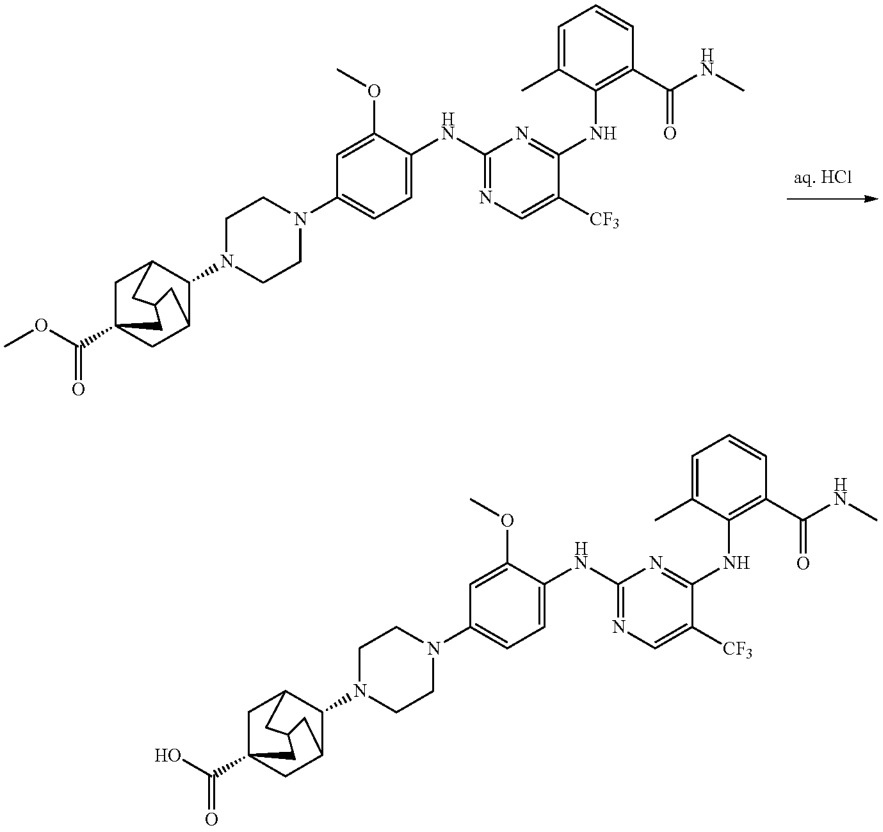

The title compound was synthesized in the same manner as in Example 17 by using methyl (cis)-4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-carboxylate instead of 4-(3-methoxy-4-((4-((2-methyl-6-(methylcarbamoyl)phenyl)amino)-5-(trifluoromethyl)pyrimidin-2-yl)amino)phenoxy) adamantan-1-methyl carboxylate in step 1 of Example 17.

$^{1}H$ NMR (400 MHz, $CD_3OD$): δ 8.21 (s, 1H), 7.49-7.33 (m, 3H), 6.57 (d, J=2.4 Hz, 1H), 6.13 (m, 2H), 3.84 (s, 3H), 3.14 (m, 4H), 2.80 (s, 3H), 2.72 (m, 4H), 2.31-2.23 (m, 3H), 2.22 (s, 3H), 2.16-2.09 (m, 2H), 2.07-2.00 (m, 2H), 1.97-1.85 (m, 5H), 1.49-1.41 (m, 2H)

<Example 41> Preparation of 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)-N-methyladamantane-1-carboxamide (compound 41)

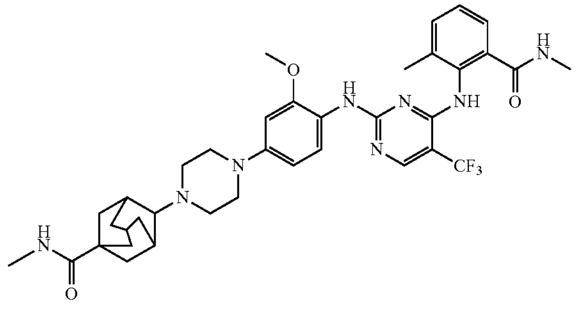

[Step 1] Preparation of 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)-N-methyladamantane-1-carboxamide

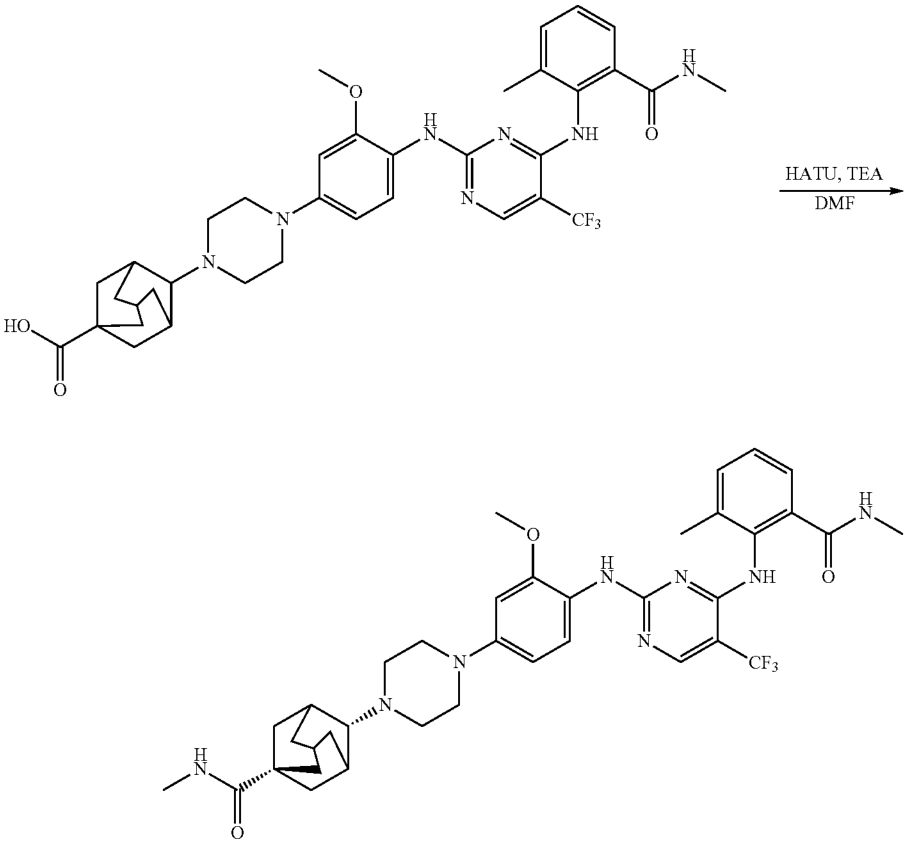

The title compound was synthesized in the same manner as in Example 18 by using 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantane-1-carboxylic acid instead of 4-(3-methoxy-4-((4-((2-methyl-6-(methylcarbamoyl)phenyl)amino)-5-(trifluoromethyl)pyrimidin-2-yl)amino)phenoxy) adamantan-1-carboxylic acid in step 1 of Example 18.

$^1$H NMR (400 MHz, $CD_3OD$): δ 8.19 (s, 1H), 7.47-7.31 (m, 3H), 6.55 (d, J=2.4 Hz, 1H), 6.11 (m, 2H), 3.82 (s, 3H), 3.12 (m, 4H), 2.80 (s, 3H), 2.78 (s, 3H), 2.70 (m, 4H), 2.29-2.21 (m, 3H), 2.20 (s, 3H), 2.14-2.07 (m, 2H), 2.05-1.98 (m, 2H), 1.95-1.83 (m, 5H), 1.47-1.39 (m, 2H)

<Example 42> Preparation of 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantane-1-carboxamide (compound 42)

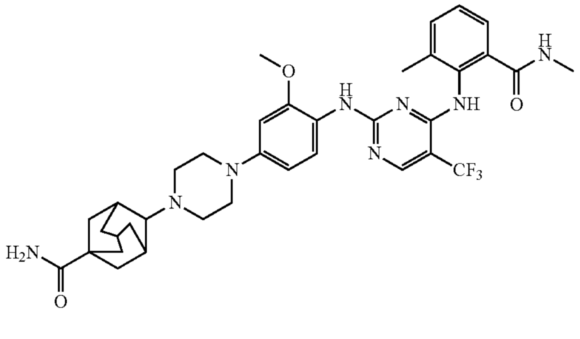 [SMILES: CNC(=O)c1cccc(C)c1Nc1nc(Nc2ccc(N3CCN(C4C5CC6CC4CC(C(N)=O)(C6)C5)CC3)cc2OC)ncc1C(F)(F)F]

[Step 1] Preparation of 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)adamantane-1-carboxamide

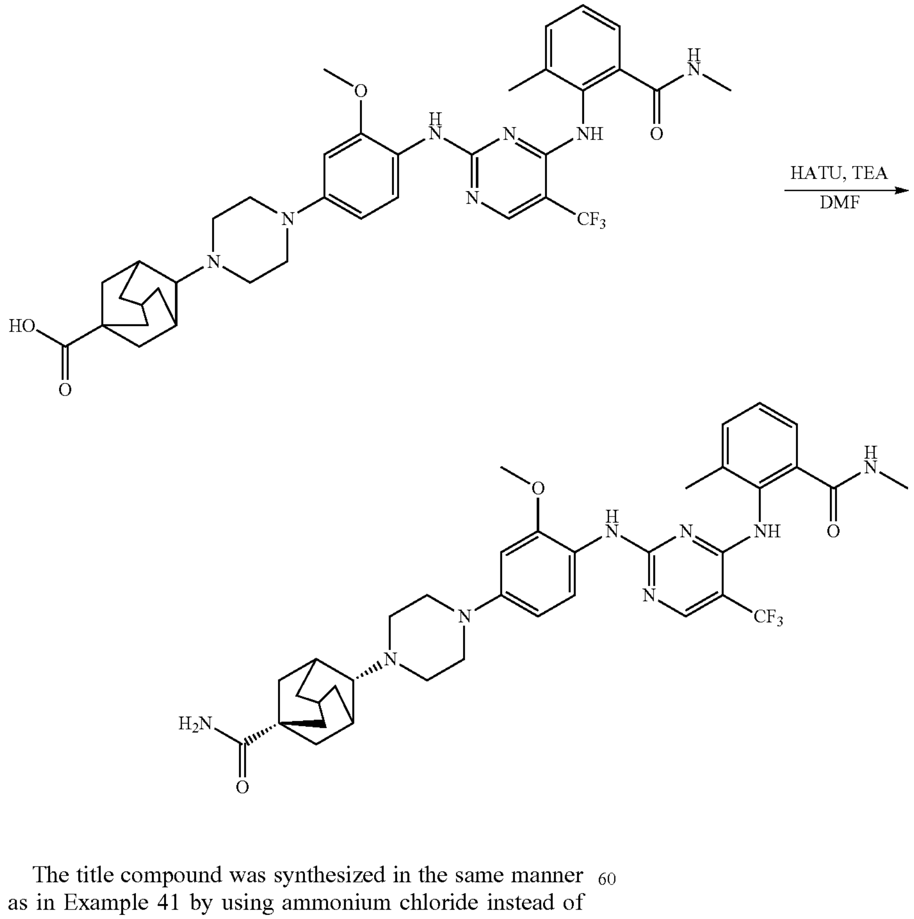

The title compound was synthesized in the same manner as in Example 41 by using ammonium chloride instead of methylamine hydrochloride in step 1 of Example 41.

$^1$H NMR (400 MHz, $CD_3OD$): δ 8.19 (s, 1H), 7.47-7.31 (m, 3H), 6.55 (d, J=2.4 Hz, 1H), 6.11 (m, 2H), 3.82 (s, 3H), 3.12 (m, 4H), 2.78 (s, 3H), 2.70 (m, 4H), 2.29-2.21 (m, 3H), 2.20 (s, 3H), 2.14-2.07 (m, 2H), 2.05-1.98 (m, 2H), 1.95-1.83 (m, 5H), 1.47-1.39 (m, 2H)

<Example 43> Preparation of 4-(4-(3-methoxy-4-((4-((2-methyl-6-(methylcarbamoyl)phenyl)amino)-5-(trifluoromethyl)pyrimidin-2-yl)amino)phenyl) piperazin-1-yl)-N,N-dimethyladamantane-1-carboxamide (compound 43)

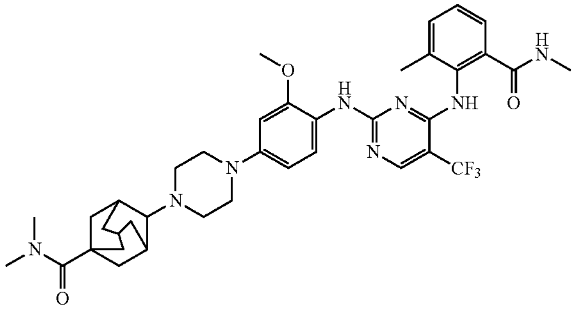

[Step 1] Preparation of 4-(4-(3-methoxy-4-((4-((2-methyl-6-(methylcarbamoyl)phenyl)amino)-5-(trifluoromethyl)pyrimidin-2-yl)amino)phenyl)piperazin-1-yl)-N,N-adamantane-1-carboxamide

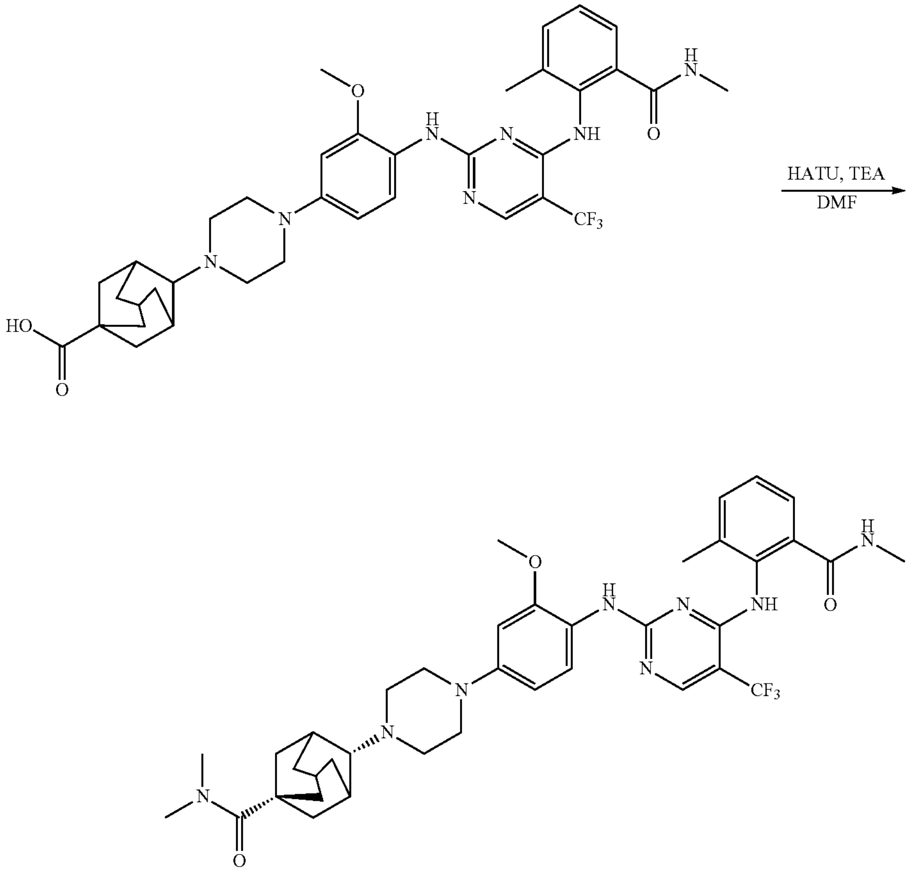

The title compound was synthesized in the same manner as in Example 41 by using dimethylamine hydrochloride instead of methylamine hydrochloride in step 1 of Example 41.

$^1$H NMR (400 MHz, $CD_3OD$): δ 8.19 (s, 1H), 7.47-7.31 (m, 3H), 6.55 (d, J=2.4 Hz, 1H), 6.11 (m, 2H), 3.82 (s, 3H), 3.12 (m, 4H), 2.98, (s, 3H), 2.78 (s, 3H), 2.70 (m, 4H), 2.29-2.21 (m, 3H), 2.20 (s, 3H), 2.14-2.07 (m, 2H), 2.05-1.98 (m, 2H), 1.95-1.83 (m, 5H), 1.47-1.39 (m, 2H)

<Example 44> Preparation of 2-((2-((4-(4-(5-aminoadamantan)-2-yl)piperazin-1-yl)-2-methoxyphenyl)amino)-5-(trifluoromethyl)pyrimidin-4-yl) amino)-N,3-dimethylbenzamide (compound 44)

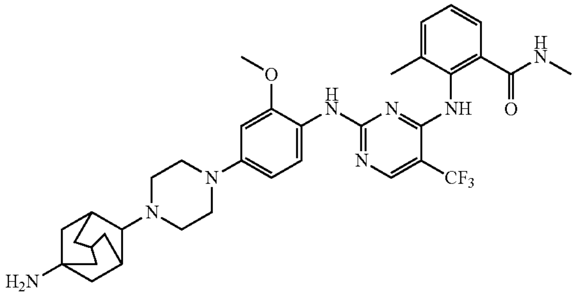 [SMILES: CNC(=O)c1cccc(C)c1Nc1nc(Nc2ccc(N3CCN(C4C5CC6CC4CC(N)(C6)C5)CC3)cc2OC)ncc1C(F)(F)F]

[Step 1] Preparation of (9H-fluoren-9-yl)methyl (4-(4-(4-((4-chloro-5-(trifluoromethyl)pyrimidin-2-yl)amino)-3-methoxyphenyl)piperazin-1-yl) adamantan-1-yl)carbamate

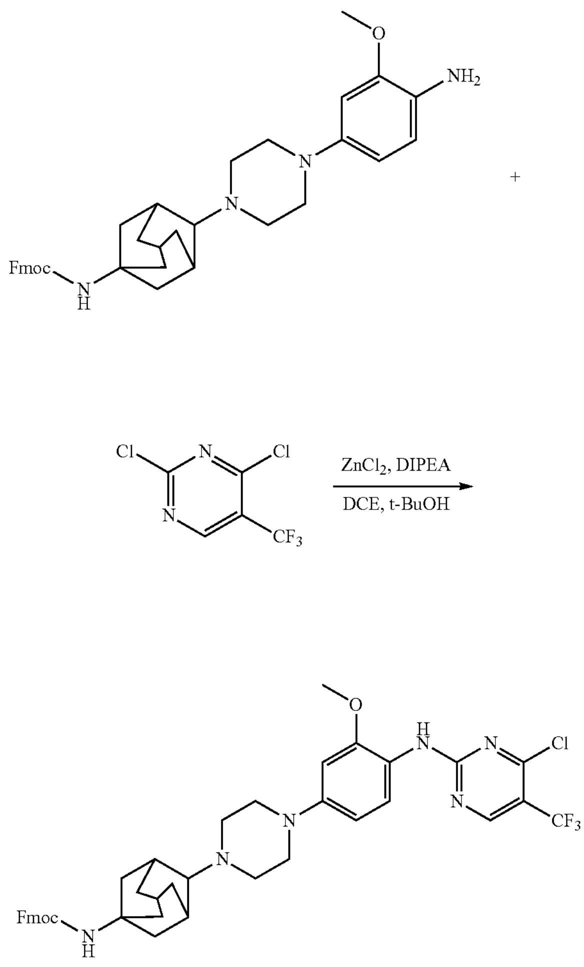

The title compound was synthesized in the same manner as in Example 1 by using (9H-fluoren-9-yl)methyl (4-(4-(4-amino-3-methoxyphenyl)piperazin-1-yl) adamantan-1-yl) carbamate instead of (trans)-4-((4-amino-3-methoxyphenyl) amino) adamantan-1-ol in step 3 of Example 1.

[Step 2] Preparation of (9H-fluoren-9-yl)methyl (4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-yl)carbamate

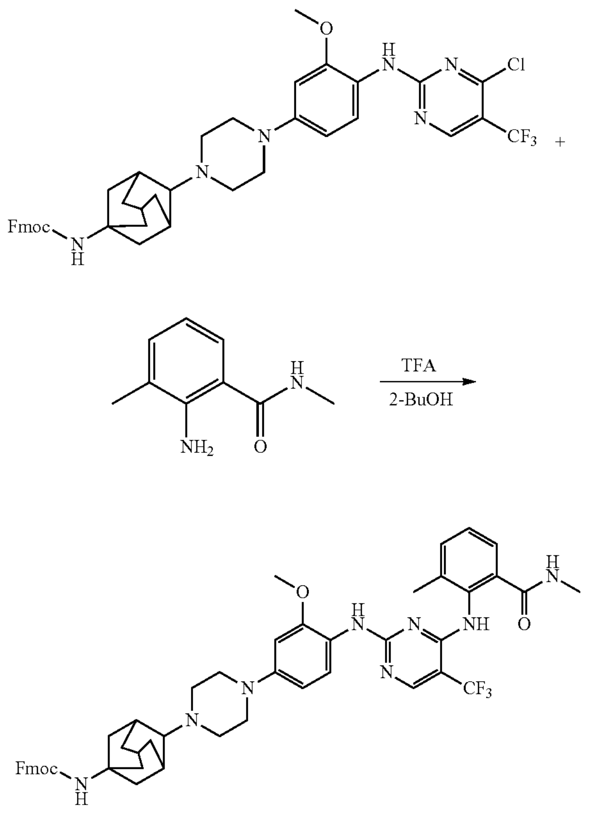

The title compound was synthesized in the same manner as in Example 1 by using methyl (trans)-4-(4-(4-((4-chloro-5-(trifluoromethyl)pyrimidin-2-yl)amino)-3-methoxyphenyl)piperazin-1-yl) adamantan-1-carboxylate instead of (trans)-4-((4-((4-chloro-5-(trifluoromethyl)pyrimidin-2-yl) amino)-3-methoxyphenyl)amino) adamantan-1-ol in step 4 of Example 1.

[Step 3] Preparation of 2-((2-((4-(4-(5-aminoadamantan-2-yl)piperazin-1-yl)-2-methoxyphenyl) amino)-5-(trifluoromethyl)pyrimidin-4-yl)amino)-N, 3-dimethylbenzamide

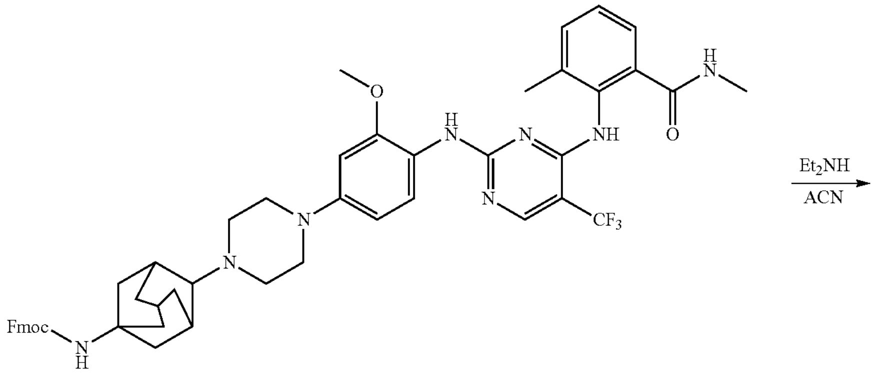

-continued

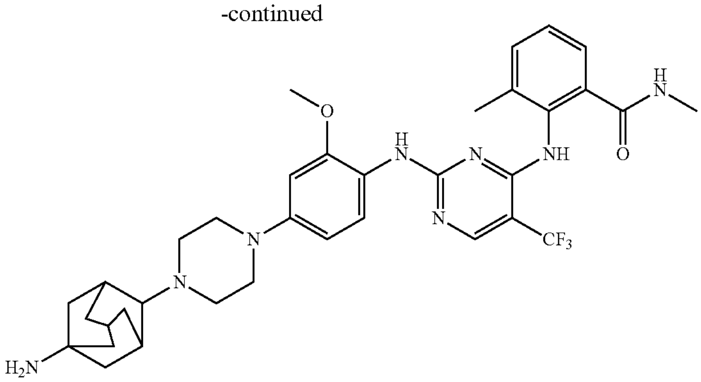

The (9H-fluoren-9-yl)methyl (4-(4-(3-methoxy-4-((4-((2-methyl-6-(methylcarbamoyl)phenyl)amino)-5-(trifluoromethyl)pyrimidin-2-yl)amino)phenyl)piperazin-1-yl) adamantan-1-yl)carbamate prepared in above step 2 was dissolved in acetonitrile and cooled in an ice bath. Diethylamine was slowly added dropwise. The resulting solution was stirred at 0° C. for one hour and stirred at room temperature for 15 hours. The solvent was concentrated under reduced pressure and purified by column chromatography to obtain the title compound.

$^1$H NMR (400 MHz, $CDCl_3$): δ 8.27 (s, 2H, overlapped), 7.42 (d, J=7.3 Hz, 1H), 7.35 (d, J=7.5 Hz, 1H), 7.32-7.27 (m, 1H), 6.48 (d, J=2.0 Hz, 1H), 6.10 (br s, 1H), 6.01 (s, 1H), 3.83 (s, 3H), 3.10 (m, 4H), 2.85 (d, J=4.8 Hz, 3H), 2.62 (m, 4H), 2.34-2.26 (m, 1H), 2.22 (s, 3H), 2.14-1.98 (m, 4H), 1.83-1.61 (m, 5H), 1.42-1.24 (m, 3H)

<Example 45> Preparation of 2-((2-((4-(4-(5-methylaminoadamantan)-2-yl)piperazin-1-yl)-2-methoxyphenyl)amino)-5-(trifluoromethyl)pyrimidin-4-yl) amino)-N,3-dimethylbenzamide (compound 45)

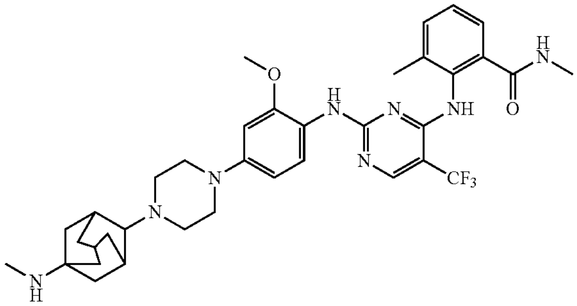

[Step 1] Preparation of 2-((2-((4-(4-(5-methylaminoadamantan-2-yl)piperazin-1-yl)-2-methoxyphenyl) amino)-5-(trifluoromethyl)pyrimidin-4-yl)amino)-N, 3-dimethylbenzamide

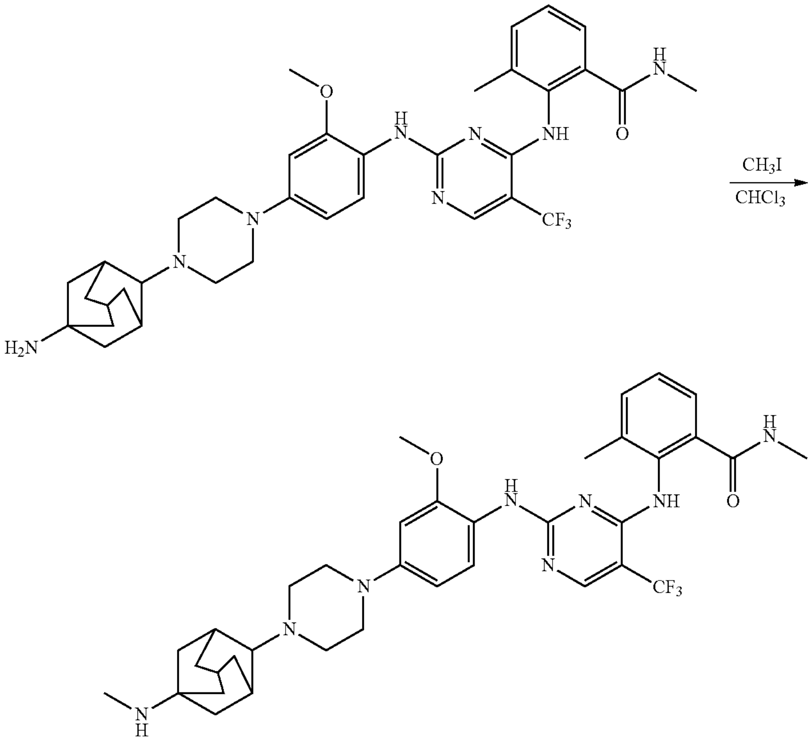

2-((2-((4-(4-(5-Aminoadamantan)-2-yl)piperazin-1-yl)-2-methoxyphenyl)amino)-5-(trifluoromethyl)pyrimidin-4-yl)amino)-N,3-dimethylbenzamide prepared in above Example 44 was dissolved in chloroform, after which potassium carbonate was added and stirred. 1 equivalent of iodomethane was slowly added and stirred at room temperature. The solvent was concentrated under reduced pressure and purified by column chromatography to obtain the title compound.

$^1$H NMR (400 MHz, $CDCl_3$): δ 8.27 (s, 2H, overlapped), 7.42 (d, J=7.3 Hz, 1H), 7.35 (d, J=7.5 Hz, 1H), 7.32-7.27 (m, 1H), 6.48 (d, J=2.0 Hz, 1H), 6.10 (br s, 1H), 6.01 (s, 1H), 3.83 (s, 3H), 3.10 (m, 4H), 2.85 (d, J=4.8 Hz, 3H), 2.62 (m, 4H), 2.55 (s, 3H), 2.34-2.26 (m, 1H), 2.22 (s, 3H), 2.14-1.98 (m, 4H), 1.83-1.61 (m, 5H), 1.42-1.24 (m, 3H)

<Example 46> Preparation of 2-((2-((4-(4-(5-dimethylaminoadamantan)-2-yl)piperazin-1-yl)-2-methoxyphenyl)amino)-5-(trifluoromethyl)pyrimidin-4-yl)amino)-N,3-dimethylbenzamide (compound 46)

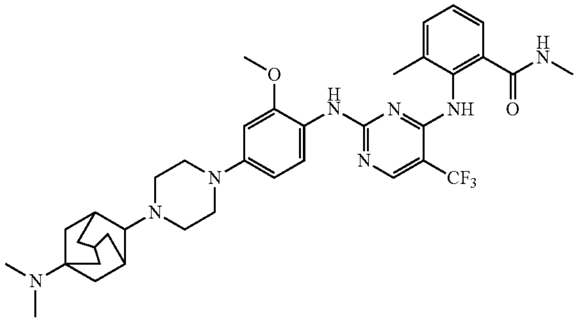

[Step 1] Preparation of 2-((2-((4-(4-(5-dimethylaminoadamantan-2-yl)piperazin-1-yl)-2-methoxyphenyl)amino)-5-(trifluoromethyl)pyrimidin-4-yl)amino)-N,3-dimethylbenzamide

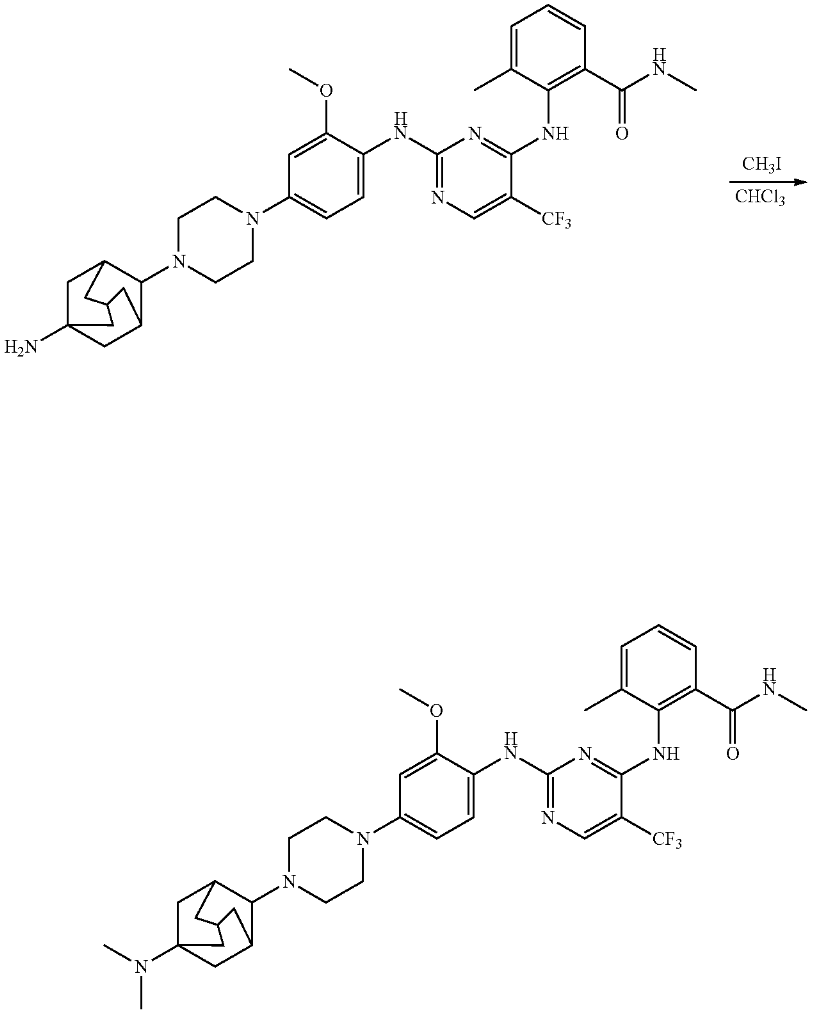

2-((2-((4-(4-(5-Aminoadamantan)-2-yl)piperazin-1-yl)-2-methoxyphenyl)amino)-5-(trifluoromethyl)pyrimidin-4-yl)amino)-N,3-dimethylbenzamide prepared in above Example 44 was dissolved in chloroform, after which potassium carbonate was added and stirred. Iodomethane (2 equiv.) was slowly added and stirred at room temperature. The solvent was concentrated under reduced pressure and purified by column chromatography to obtain the title compound.

$^1$H NMR (400 MHz, $CDCl_3$): δ 8.27 (s, 2H, overlapped), 7.42 (d, J=7.3 Hz, 1H), 7.35 (d, J=7.5 Hz, 1H), 7.32-7.27 (m, 1H), 6.48 (d, J=2.0 Hz, 1H), 6.10 (br s, 1H), 6.01 (s, 1H), 3.83 (s, 3H), 3.10 (m, 4H), 2.85 (d, J=4.8 Hz, 3H), 2.62 (m, 4H), 2.34-2.26 (m, 1H), 2.24 (s, 6H), 2.22 (s, 3H), 2.14-1.98 (m, 4H), 1.83-1.61 (m, 5H), 1.42-1.24 (m, 3H)

<Example 47> Preparation of 2-((2-((4-(4-(5-acrylamidoadamantan)-2-yl)piperazin-1-yl)-2-methoxyphenyl)amino)-5-(trifluoromethyl)pyrimidin-4-yl)amino)-N,3-dimethylbenzamide (compound 47)

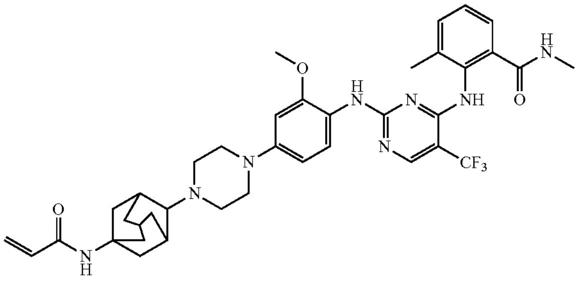 [SMILES: C=CC(=O)NC12CC3CC(C1)C(N1CCN(c4ccc(Nc5ncc(C(F)(F)F)c(Nc6c(C)cccc6C(=O)NC)n5)c(OC)c4)CC1)C(C3)C2]

[Step 1] Preparation of 2-((2-((4-(4-(5-acrylamidoadamantan-2-yl)piperazin-1-yl)-2-methoxyphenyl)amino)-5-(trifluoromethyl)pyrimidin-4-yl)amino)-N,3-dimethylbenzamide

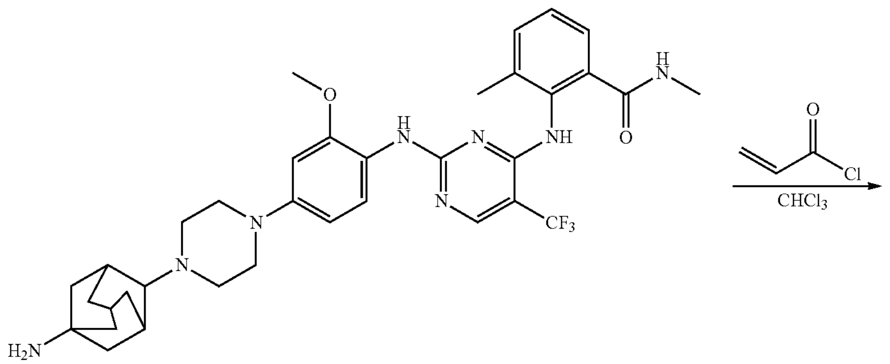

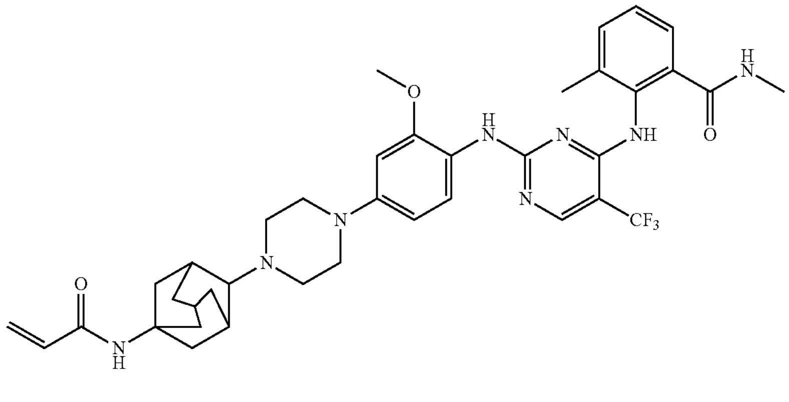

2-((2-((4-(4-(5-Aminoadamantan)-2-yl)piperazin-1-yl)-2-methoxyphenyl)amino)-5-(trifluoromethyl)pyrimidin-4-yl)amino)-N,3-dimethylbenzamide prepared in above Example 44 was dissolved in chloroform, after which potassium carbonate was added and stirred. Acryloyl chloride was slowly added and stirred at room temperature. The solvent was concentrated under reduced pressure and purified by column chromatography to obtain the title compound.

$^1$H NMR (400 MHz, $CDCl_3$): δ 8.27 (s, 2H, overlapped), 7.42 (d, J=7.3 Hz, 1H), 7.35 (d, J=7.5 Hz, 1H), 7.32-7.27 (m, 1H), 6.52 (m, 1H), 6.48 (d, J=2.0 Hz, 1H), 6.10 (br s, 1H), 6.06 (m, 1H), 6.01 (s, 1H), 5.74 (m, 1H), 3.83 (s, 3H), 3.10 (m, 4H), 2.85 (d, J=4.8 Hz, 3H), 2.62 (m, 4H), 2.34-2.26 (m, 1H), 2.22 (s, 3H), 2.14-1.98 (m, 4H), 1.83-1.61 (m, 5H), 1.42-1.24 (m, 3H)

Test Example

<Experimental Example 1> Measurement of FAK, Pyk2 and InsR inhibitory activity of compound The inhibitory activity of the adamantane derivative compounds of the present invention to FAK, Pyk2 and InsR was confirmed through a biochemical kinase analysis, and table 1 below shows the $IC_{50}$ values for each kinase inhibitory activity of each compound. Briefly, a kinase test was performed and quantified according to the manufacturer's instructions after treating the adamantane derivative compound of the present invention by using the ADP-Glo™ Kinase Assay Kit (FAK, Promega, V1971; Pyk2, Promega, V4083; InsR, Promega, V9401) containing each kinase of Promega.

TABLE 1

| Compound # | FAK $IC_{50}$ (nM) | Pyk2 $IC_{50}$ (nM) | InsR $IC_{50}$ (nM) |
|---|---|---|---|
| 1 | 82.9 | 124.5 | >10,000 |
| 2 | 205.5 | — | >10,000 |
| 3 | 154.2 | 255.9 | >10,000 |
| 4 | 46.2 | 150.5 | 5,666 |
| 5 | 69.9 | — | 4,685 |
| 6 | 96.5 | 157.0 | >10,000 |
| 7 | 46.9 | 108.1 | 6,148 |
| 8 | 53.3 | — | >10,000 |
| 9 | 98.1 | — | >10,000 |
| 10 | 96.7 | — | >10,000 |
| 11 | 65.1 | 231.0 | >10,000 |
| 14 | 57.0 | — | — |
| 18 | 92.9 | — | — |
| 19 | 126.8 | — | — |
| 20 | 98.9 | — | — |
| 22 | 57.0 | — | — |
| 23 | 77.5 | — | — |
| 25 | 45.5 | 90.6 | >10,000 |
| 27 | 39.5 | 81.4 | >10,000 |
| 28 | 29.0 | 64.5 | >10,000 |
| 30 | — | 18.2 | 3,804 |
| 32 | — | 153.6 | 2,153 |
| 33 | — | 100.6 | 2,054 |
| 34 | — | 427.0 | 1,636 |
| 35 | — | 417.6 | 1,437 |
| 36 | 61.4 | — | — |
| 37 | 43.6 | — | — |
| 38 | 70.0 | — | — |
| 39 | 58.0 | — | — |
| 40 | 58.3 | — | — |

Referring to above table 1, it could be seen that the adamantane derivative according to the present invention has an excellent inhibitory activity to FAK and Pyk2(FAK2). Furthermore, it could be seen that the adamantane derivative does not inhibit the activity of insulin receptor (Ins-R) while selectively inhibiting the activity of FAK and Pyk2(FAK2).

<Experimental Example 2> Measurement of FAK inhibitory activity of compound in human triple-negative breast cancer cell line MDA-MB-231

In order to measure the inhibitory activity of the adamantane derivative compounds of the present invention to the FAK in vitro, an FAK [pY397] enzyme-linked immunosorbent assay test was performed on MDA-MB-231, a human triple-negative breast cancer cell line, and table 2 below shows the $IC_{50}$ values of each compound.

Briefly, an enzyme-linked immunosorbent assay test was performed according to the manufacturer's instructions by using the FAK (Phospho) [pY397] Human ELISA Kit (Thermo Fisher Scientific, KH00441) after dispensing $1\times10^6$ MDA-MB-231 cells into each well of a 6-well plate, inducing cell stabilization for 24 hours, and treating each compound at different concentrations (o, 1, 5, 10, 50, 100, 500, 1000 nM) for one hour.

TABLE 2

| Compound # | FAK inhibitory activity ($IC_{50}$, nM) |
|---|---|
| 1 | 83 |
| 2 | 111 |
| 3 | 92 |
| 4 | 34 |
| 5 | 32 |
| 6 | 118 |
| 7 | 38 |
| 8 | 121 |
| 10 | 382 |
| 11 | 118 |
| 20 | 153 |
| 23 | 234 |
| 25 | 27 |
| 27 | 55 |

Referring to above table 2, it could be seen that the adamantane derivative according to the present invention has excellent FAK inhibitory activity in MDA-MB-231, a human triple-negative breast cancer cell line.

<Experimental Example 3> Measurement of FAK inhibitory activity in various human triple-negative breast cancer cell line The inhibitory activity of compound 4, which is the adamantane derivative compound of the present invention, to the FAK in vitro was confirmed in various triple-negative breast cancer cell lines through the FAK [pY397] enzyme-linked immunosorbent assay as described above, and table 3 below shows the $IC_{50}$ values of each cell line.

TABLE 3

| FAK inhibitory activity ($IC_{50}$, nM) | | | | | | |
|---|---|---|---|---|---|---|
| | Cell line | | | | | |
| Compound | MDA-MB-231 | MDA-MB-453 | HCC70 | BT-20 | BT-549 | Hs578T |
| 4 | 34 | 20 | 59 | 63 | 49 | 20 |

The inhibitory activity ability of the compound 4 of the present invention on various kinases is as follows.

The data on this kinase activity inhibition were obtained from the results of screening and profiling kinases performed by Eurofins, and table 4 below shows a degree of inhibitory activity (% inhibition rate) and $IC_{50}$ values of the corresponding kinases that inhibit at least 70% of the 107 screened kinases at a single concentration (1 PM) of the compound.

TABLE 4

| Kinase | FAK | Pyk2 | Met | ALK |
|---|---|---|---|---|
| % inhibition rate (at 1 μM) | 97 | 96 | 79 | 72 |
| $IC_{50}$ [nM] | 78 | 301 | 542 | 802 |

Referring to above table 3, it could be seen that the adamantane derivative according to the present invention has an excellent FAK inhibitory activity in MDA-MB-231, MDA-MB-453, HCC70, BT-20, BT-549 and Hs578T, which are various triple-negative breast cancer cell lines.

<Experimental Example 4> Measurement of growth inhibitory activity in various human triple-negative breast cancer cell line A 3D spheroid assay was performed as a method for measuring the growth of cancer cells under three-dimensional (3D) culture conditions. Briefly, the $5\times10^3$ triple-negative breast cancer cells in each well of a 96-well flat plate were three-dimensionally cultured for three days by using MammoCult™ Human Medium Kit (Stemcell Technologies, #05620) and the formed cancer cell spheroids were treated with compound 4 at different concentrations (o, 0.2, 0.5, 1, 2, 5, 10, 20 PM) for 96 hours. The cancer cell growth inhibitory effect of the compound was quantified according to the manufacturer's instructions by using CellTiter-Glo® 3D Cell Viability Assay Kit (Promega, G9681).

FIG. 1 shows a degree of growth inhibition of cancer cell spheroids by treatment with the compound at different concentrations in MDA-MB-231 cells as a representative example of a 3D spheroid assay.

Table 5 below shows $IC_{50}$ values for the cancer cell spheroid growth inhibitory activity of compound 4, an adamantane derivative compound of the present invention in various triple-negative breast cancer cell lines including MDA-MB-231.

TABLE 5

| Cancer cell growth inhibitory activity ($IC_{50}$, nM) | | | | | | |
|---|---|---|---|---|---|---|
| | Cell line | | | | | |
| Compound | MDA-MB-231 | MDA-MB-453 | HCC70 | BT-20 | BT-549 | Hs578T |
| 4 | 742 | 1,040 | 1,449 | 2,533 | 4,709 | >10,000 |

Referring to FIG. 1, it could be seen that the adamantane derivative according to the present invention has excellent cancer cell spheroid inhibitory activity at all the concentrations. In addition, referring to above table 5, it could be seen that the adamantane derivative according to the present invention has excellent cancer cell spheroid growth inhibitory activity in MDA-MB-231, MDA-MB-453, HCC70, BT-20, BT-549 and Hs578T, which are various triple-negative breast cancer cell lines.

<Experimental Example 5>3D invasion inhibitory effect in human triple-negative breast cancer cell line MDA-MB-231

A cell invasion assay was performed and quantified according to a 3D invasion assay. Briefly, MDA-MB-231 cells were cultured in a 96-well round plate ($5\times10^3$/well) for three days to form cancer cell spheroids, then fixed in a mixture of semi-solid Matrigel and type I collagen, and then treated with compound 4 at different concentrations (1, 5 μM). A degree of infiltration was analyzed by using a microscope (see FIG. 2) and an imaging software ImageJ in 72 hours later, and an obtained area value was quantified based on a following equation (Equation 1) and shown in a graph (see FIG. 3).

Relative invasion=(total area of compound treated group−spheroid area of compound treated group)/(total area of control−spheroid area of control) [Equation 1]

Figure 2:
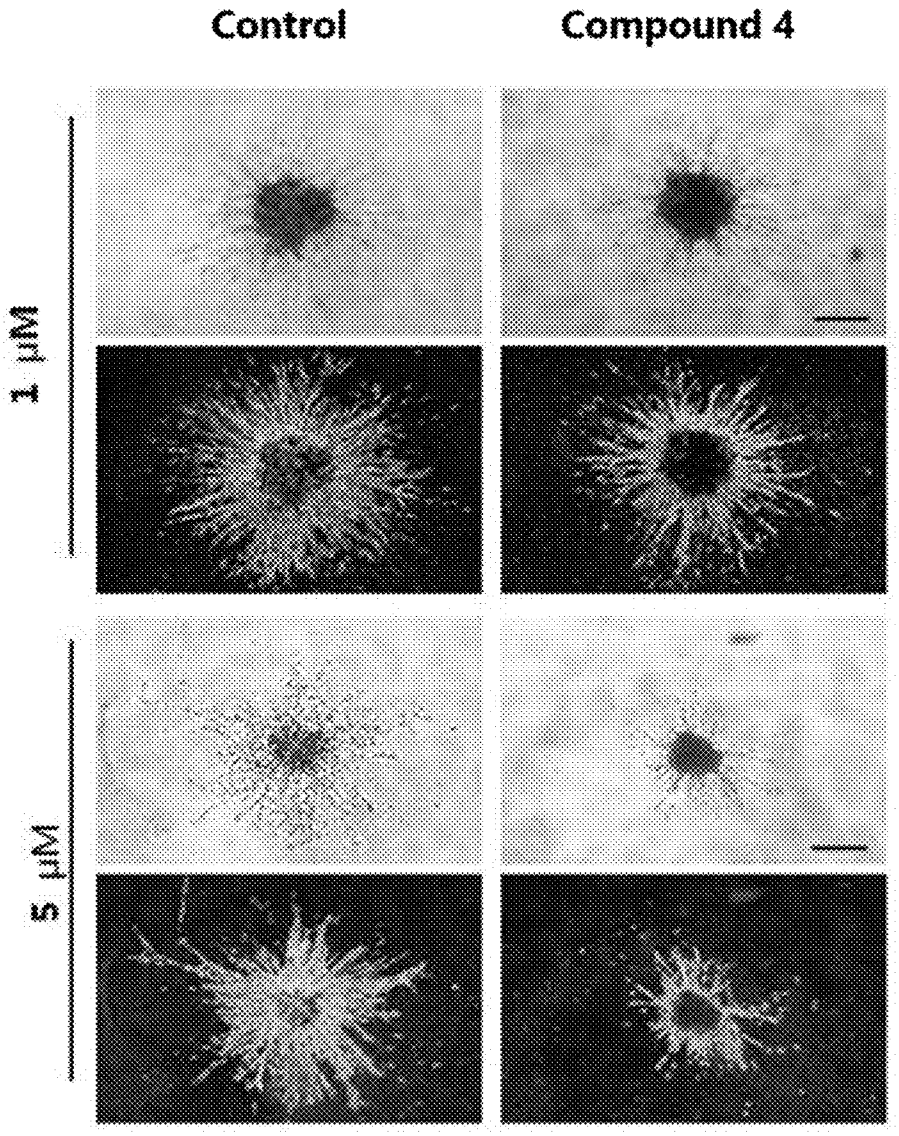
FIG. 2 shows the results of a microscopic analysis on a degree of 3D invasion inhibition of MDA-MB-231, a human triple-negative breast cancer cell line by the adamantane derivative compound of the present invention.
Figure 3:
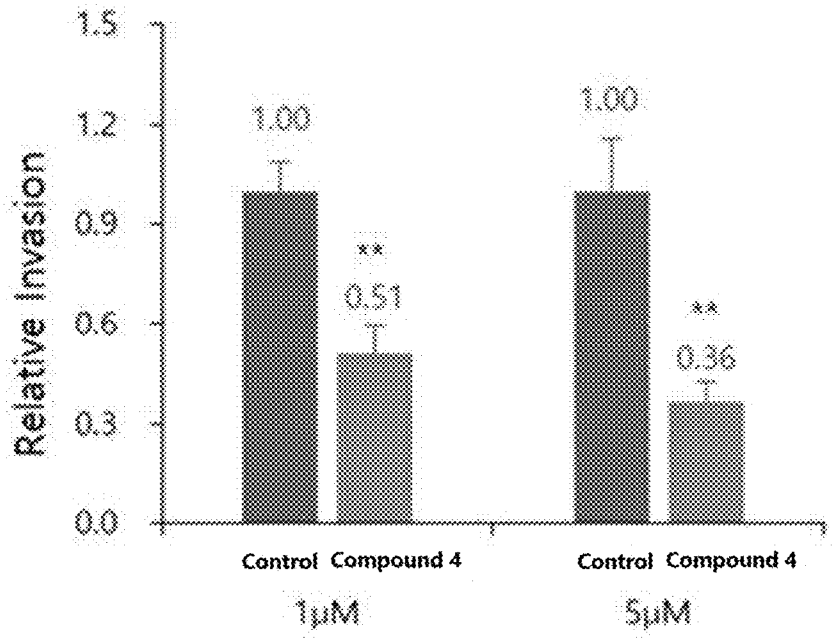
FIG. 3 shows the results of analyzing a degree of 3D invasion inhibition of MDA-MB-231, a human triple-negative breast cancer cell line by the adamantane derivative compound of the present invention.

Referring to FIGS. 2 and 3, it could be seen that the adamantane derivative according to the present invention has excellent invasion inhibitory activity in MDA-MB-231, a human triple-negative breast cancer cell line.

Figure 4:
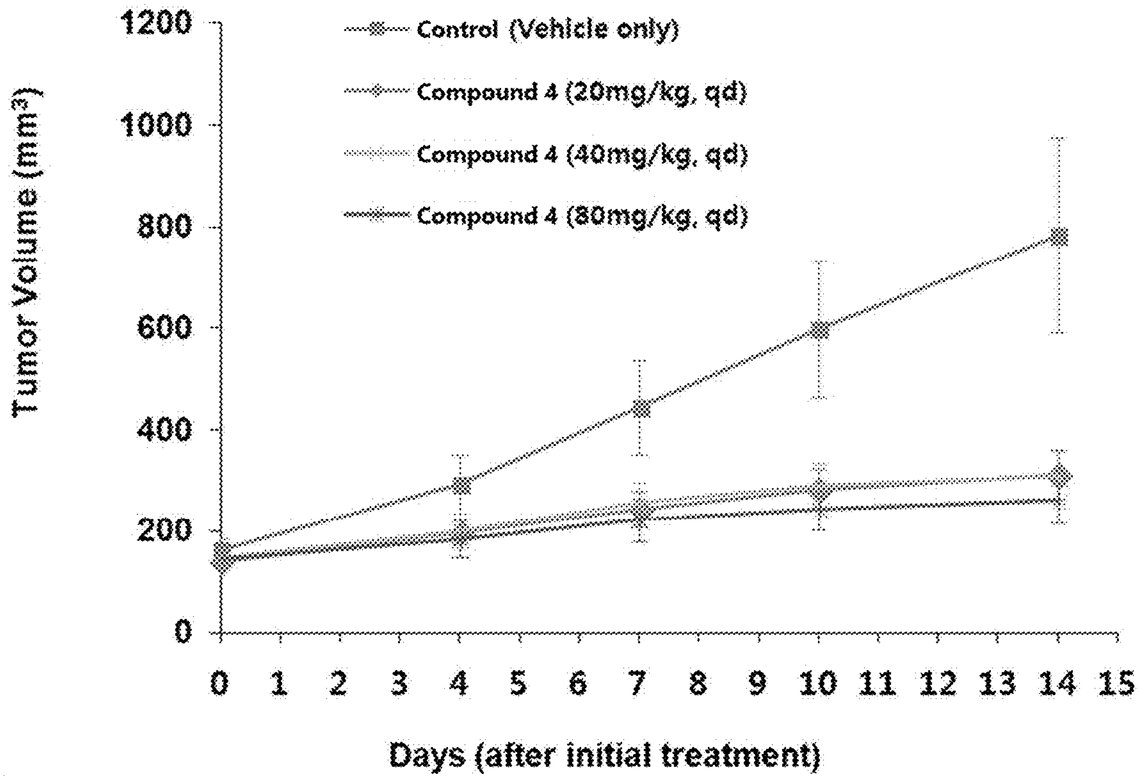
FIG. 4 shows the results of analyzing a degree of tumor growth inhibition by the adamantane derivative compound of the present invention in a triple-negative breast cancer xenograft mouse model.

<Experimental Example 6> Tumor growth inhibitory effect on triple-negative breast cancer xenograft mouse model In one week after acclimatization of five-week-old male nude mice, $1\times10^6$ MDA-MB-231 cells were subcutaneously inoculated into the mice and observed until a tumor volume reached about 100 $mm^3$ after 14 days. In order to confirm a tumor growth inhibitory effect of derived candidate materials in the triple-negative breast cancer xenograft mouse model, eight mice for each group were divided into a control group and three experimental groups at different concentrations (4-20 mg/kg, 4-40 mg/kg and 4-80 mg/kg), and each compound was treated once daily. A tumor volume of the mice was measured three times a week on every other day, and the mice were sacrificed on day 29 after cell inoculation. FIG. 4 is a graph showing the tumor volume calculated based on the following formula (Equation 2) with a starting date of drug treatment as day 1.

Tumor volume ($mm^3$)=[(tumor short diameter$^2$×tumor long diameter)/2] [Equation 2]

Table 6 below shows the comparison of average tumor growth of each compound treated group compared to an average tumor growth of the control group by calculating a tumor growth inhibition rate (% TGI) based on the following formula (Equation 3).

$$\% TGI=100\times[1-(TV_{final\ treated}-TV_{initial\ treated})/(TV_{final\ control}-TV_{initial\ control})]$$ [Equation 3]

TABLE 6

| | Control | Compound 4 (20 mg/kg) | Compound 4 (40 mg/kg) | Compound 4 (80 mg/kg) |
|---|---|---|---|---|
| % TGI | — | 72.11 | 74.03 | 81.28 |

Referring to FIG. 4 and Table 6, it could be seen that the adamantane derivative according to the present invention has excellent tumor growth inhibitory activity in a triple-negative breast cancer xenograft mouse model.

From the results of above Experimental Examples 1 to 6, it could be seen that the adamantane derivative according to the present invention has an excellent therapeutic effect on FAK activity-associated diseases.

The present invention has been described with reference to preferred exemplary embodiments herein, but it will be understood by those skilled in the art that the present invention may be variously changed and modified without departing from the spirit and field of the present invention, as described in the following scope of patent claims.

The invention claimed is:

1. An adamantane derivative represented by formula 1 below, a pharmaceutically acceptable salt thereof, stereoisomer thereof, hydrate or solvate thereof:

[Formula 1]

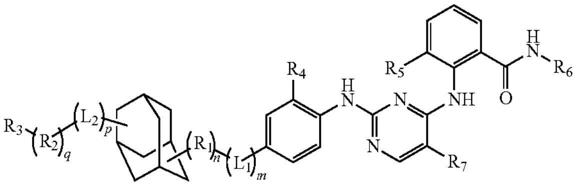

wherein in above formula 1, $L_1$ and $L_2$ are each independently a single bond, $C_{1-10}$ alkylene, $C_{2-10}$ alkenylene, $C_{2-10}$ alkynylene, —N(Ra)—, —C(═O)—N(Ra)—, —N(Ra)—C(═O)—, —C(═O)—, —O—, —C(═O)—O—, —N(Ra)— C(═O)—O—, —N(Ra)—S(═O)—, —N(Ra)—S(═O)$_2$—, —S(═O)(═N—Ra)—, or —S—;

$R_1$ and $R_2$ are each independently $C_{1-10}$ heterocycloalkylene, $C_{3-10}$ cycloalkylene, $C_{5-16}$ arylene or $C_{4-10}$ heteroarylene;

$R_3$ is H, $C_{1-10}$ alkyl, $C_{2-10}$ alkenyl, —O—Ra, ═O, —NH—Ra, —NH(C═O)—Ra or $C_{1-10}$ heterocycloalkyl;

$R_4$ is —O—Ra;

$R_5$ and $R_6$ are each independently H or $C_{1-10}$ alkyl;

$R_7$ is —$CF_3$ or a halogen atom;

Ra is H, —$CF_3$ or $C_{1-10}$ alkyl; and m, n, p and q are each independently 0 or 1.

2. The adamantane derivative, pharmaceutically acceptable salt thereof, stereoisomer thereof, hydrate or solvate thereof according to claim 1:

wherein in the above formula 1, $R_1$ and $R_2$ are each independently

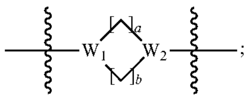;

$R_3$ is H, $C_{1-10}$ alkyl, $C_{2-10}$ alkenyl, —O—Ra, ═O, —NH—Ra, —NH(C═O)—Ra or

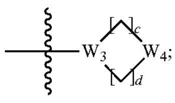;

$W_1$, $W_2$ and $W_3$ are each independently CH or N;

$W_4$ is $CH_2$, NH or O;

Ra is H, —$CF_3$ or $C_{1-10}$ alkyl; and a, b, c and d are each independently 1, 2 or 3.

3. The adamantane derivative, pharmaceutically acceptable salt thereof, stereoisomer thereof, hydrate or solvate thereof according to claim 1:

wherein in the above formula 1, $R_1$ and $R_2$ are each independently

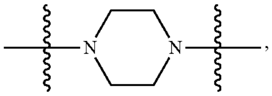,

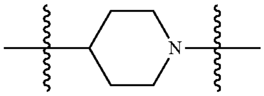 or

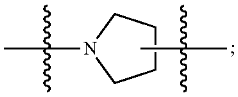;

$R_3$ is H, $C_{1-10}$ alkyl, $C_{2-10}$ alkenyl, —O—Ra, ═O, —NH—Ra, —NH(C═O)—Ra or

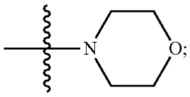 [SMILES: *N1CCOCC1];

Ra is H, —$CF_3$ or $C_{1-10}$ alkyl.

4. The adamantane derivative, pharmaceutically acceptable salt thereof, stereoisomer thereof, hydrate or solvate thereof according to claim 1, wherein the adamantane derivative represented by the above formula 1 is a compound represented by formula 2 below:

[Formula 2]

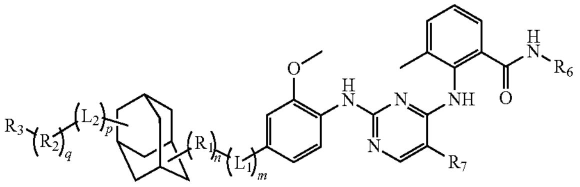

wherein in the above formula 2, $L_1$ is —N(Ra)—, —C(═O)—N(Ra)— or —O—;

$L_2$ is —N(Ra)—, —C(═O)—N(Ra)—, —N(Ra)—C(═O)—, —C(═O)— or —C(═O)—O—;

$R_1$ and $R_2$ are each independently

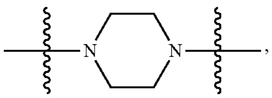,

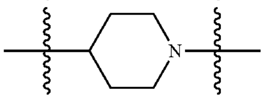 or

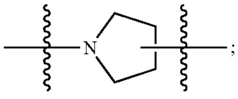;

$R_3$ is H, $C_{1-10}$ alkyl, $C_{2-10}$ alkenyl, —O—Ra, ═O, —NH—Ra, —NH(C═O)—Ra or morphoridinyl;

$R_6$ is H or $C_{1-10}$ alkyl;

$R_7$ is —$CF_3$ or Cl;

Ra is H, —$CF_3$ or $C_{1-10}$ alkyl; and m, n, p and q are each independently 0 or 1.

5. The adamantane derivative, pharmaceutically acceptable salt thereof, stereoisomer thereof, hydrate or solvate thereof according to claim 1, wherein the adamantane derivative represented by the above formula 1 is a compound selected from the group consisting of the compounds shown in the following table:
| Example # | Structure |
| --- | --- |
| 1 | 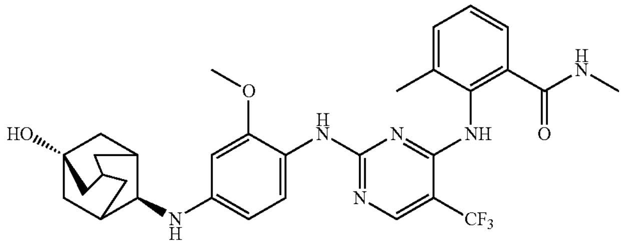 |
| 2 | 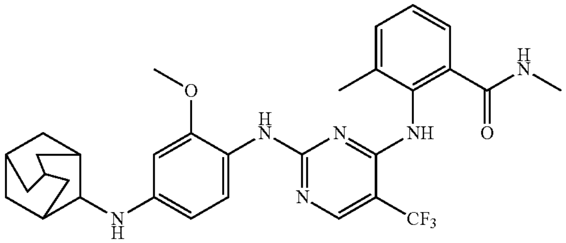 [SMILES: CNC(=O)c1cccc(C)c1Nc1nc(Nc2ccc(NC3C4CC5CC(C4)CC3C5)cc2OC)ncc1C(F)(F)F] |
| 3 | 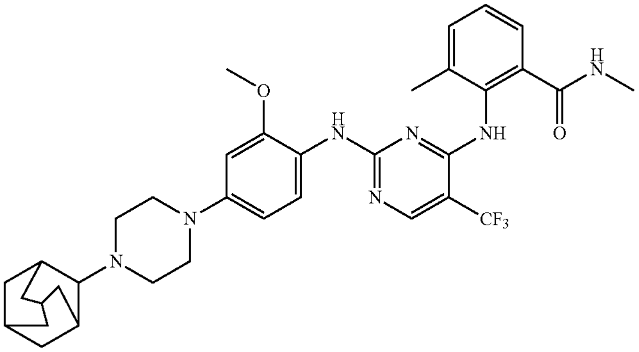 [SMILES: CNC(=O)c1cccc(C)c1Nc1nc(Nc2ccc(N3CCN(C4C5CC6CC(C5)CC4C6)CC3)cc2OC)ncc1C(F)(F)F] |
| 4 | 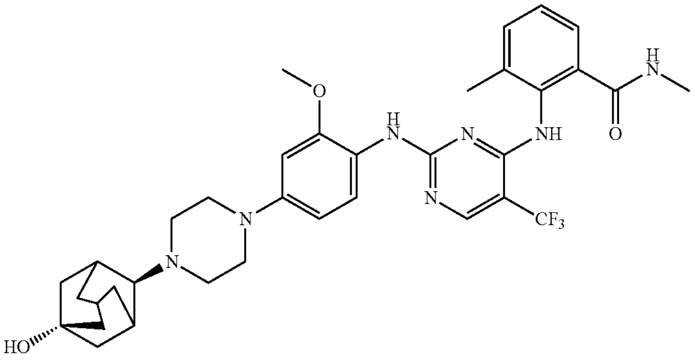 |

-continued
| Example # | Structure |
| --- | --- |
| 5 | 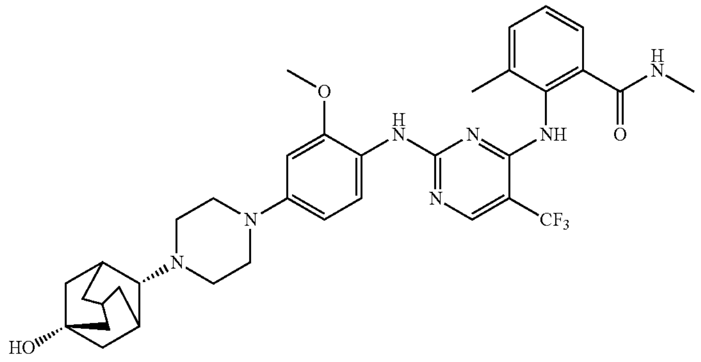 |
| 6 | 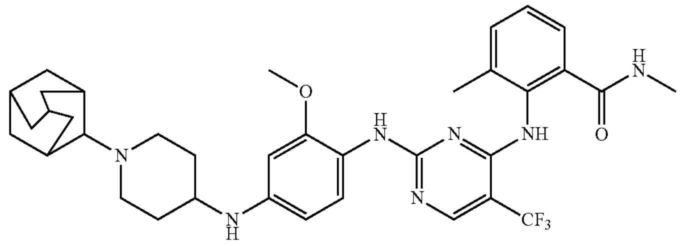 [SMILES: CNC(=O)c1cccc(C)c1Nc1nc(Nc2ccc(NC3CCN(C4C5CC6CC(C5)CC4C6)CC3)cc2OC)ncc1C(F)(F)F] |
| 7 | 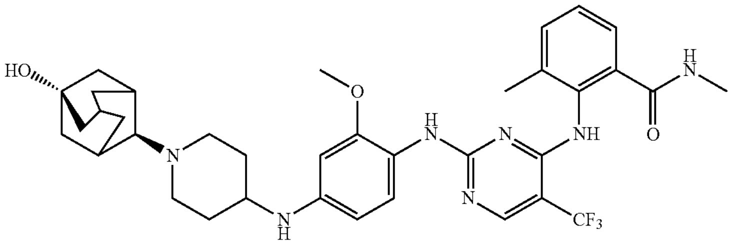 [SMILES: CNC(=O)c1cccc(C)c1Nc1nc(Nc2ccc(NC3CCN([C@H]4C5CC6CC4C[C@](O)(C6)C5)CC3)cc2OC)ncc1C(F)(F)F] |
| 8 | 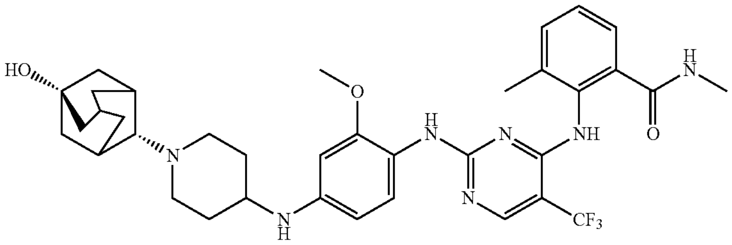 [SMILES: CNC(=O)c1cccc(C)c1Nc1nc(Nc2ccc(NC3CCN([C@H]4C5CC6CC4C[C@@](O)(C6)C5)CC3)cc2OC)ncc1C(F)(F)F] |
| 9 | 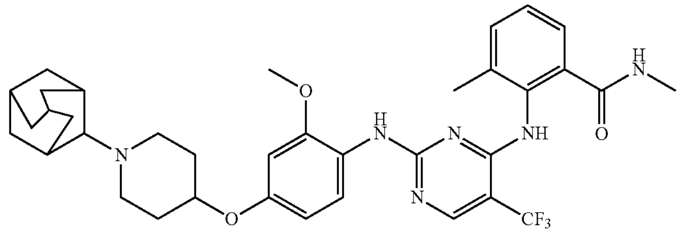 [SMILES: CNC(=O)c1cccc(C)c1Nc1nc(Nc2ccc(OC3CCN(C4C5CC6CC(C5)CC4C6)CC3)cc2OC)ncc1C(F)(F)F] |
| 10 | 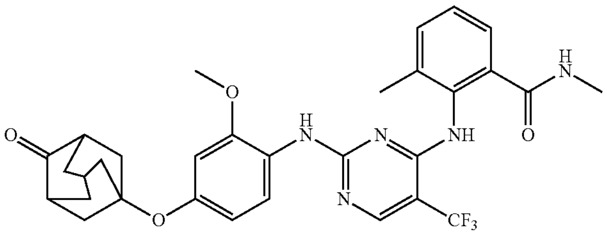 [SMILES: CNC(=O)c1cccc(C)c1Nc1nc(Nc2ccc(OC34CC5CC(C3)C(=O)C(C5)C4)cc2OC)ncc1C(F)(F)F] |

-continued
| Example # | Structure |
|---|---|
| 11 | 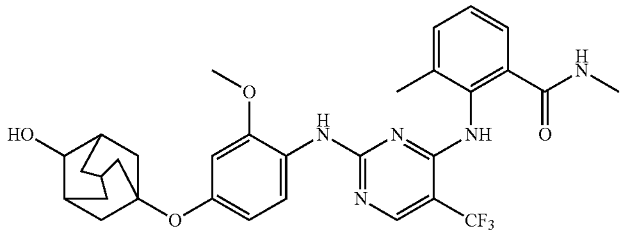 [SMILES: CNC(=O)c1cccc(C)c1Nc1nc(Nc2ccc(OC34CC5CC(C3)C(O)C(C5)C4)cc2OC)ncc1C(F)(F)F] |
| 12 | 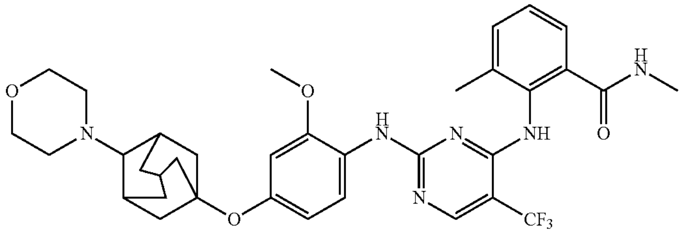 [SMILES: CNC(=O)c1cccc(C)c1Nc1nc(Nc2ccc(OC34CC5CC(C3)C(N3CCOCC3)C(C5)C4)cc2OC)ncc1C(F)(F)F] |
| 13 | 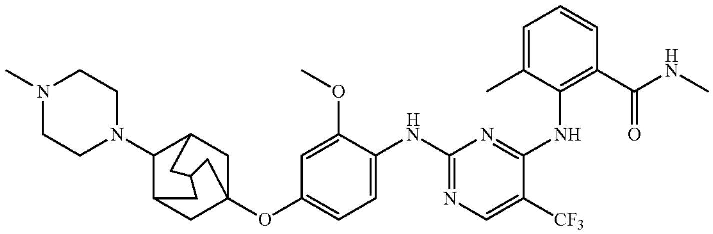 |
| 14 | 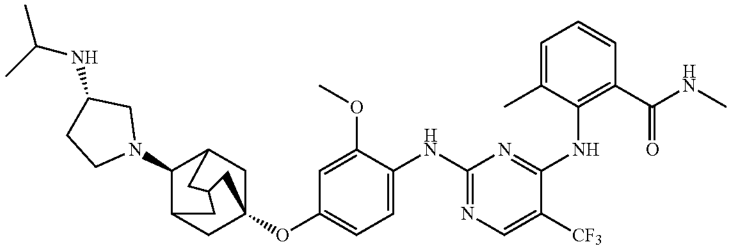 [SMILES: CNC(=O)c1cccc(C)c1Nc1nc(Nc2ccc(O[C@]34CC5CC(C3)[C@@H](N3CC[C@H](NC(C)C)C3)C(C5)C4)cc2OC)ncc1C(F)(F)F] |
| 15 | 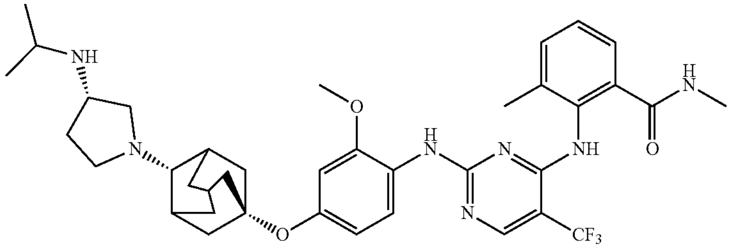 [SMILES: CNC(=O)c1cccc(C)c1Nc1nc(Nc2ccc(O[C@]34CC5CC(C3)[C@H](N3CC[C@H](NC(C)C)C3)C(C5)C4)cc2OC)ncc1C(F)(F)F] |
| 16 | 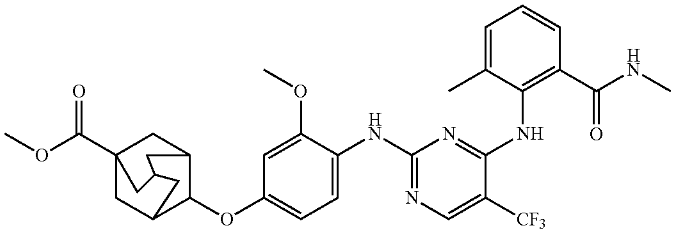 |

-continued
| Example # | Structure |
| --- | --- |
| 17 | 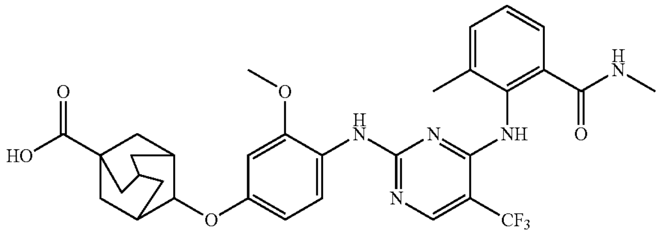 [SMILES: CNC(=O)c1cccc(C)c1Nc1nc(Nc2ccc(OC3C4CC5CC3CC(C(=O)O)(C5)C4)cc2OC)ncc1C(F)(F)F] |
| 18 | 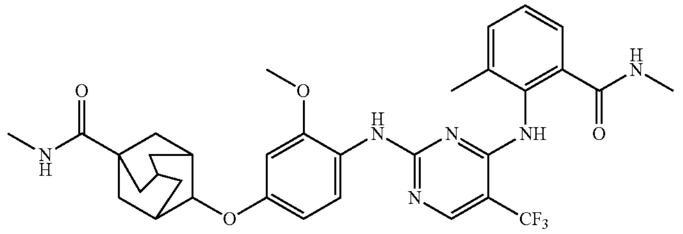 |
| 19 | 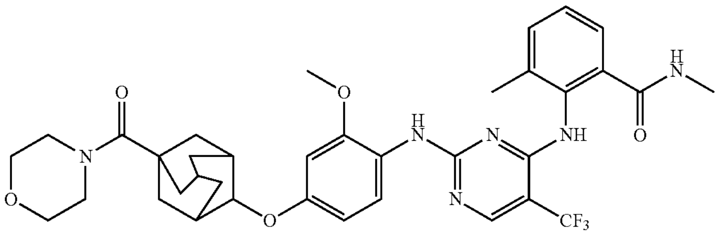 [SMILES: CNC(=O)c1cccc(C)c1Nc1nc(Nc2ccc(OC3C4CC5CC3CC(C(=O)N3CCOCC3)(C5)C4)cc2OC)ncc1C(F)(F)F] |
| 20 | 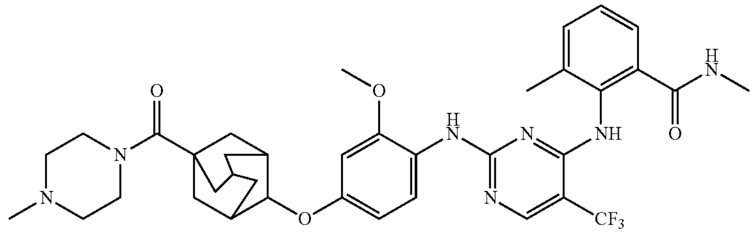 |
| 21 | 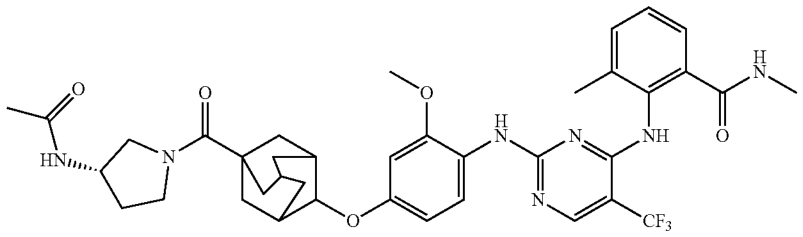 [SMILES: CNC(=O)c1cccc(C)c1Nc1nc(Nc2ccc(OC3C4CC5CC3CC(C(=O)N3CC[C@H](NC(C)=O)C3)(C5)C4)cc2OC)ncc1C(F)(F)F] |
| 22 | 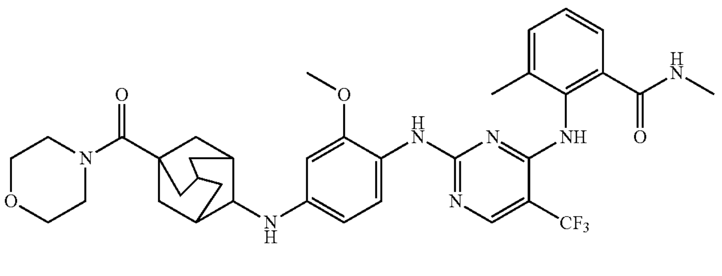 [SMILES: CNC(=O)c1cccc(C)c1Nc1nc(Nc2ccc(NC3C4CC5CC3CC(C(=O)N3CCOCC3)(C5)C4)cc2OC)ncc1C(F)(F)F] |

-continued
| Example # | Structure |
|---|---|
| 23 | 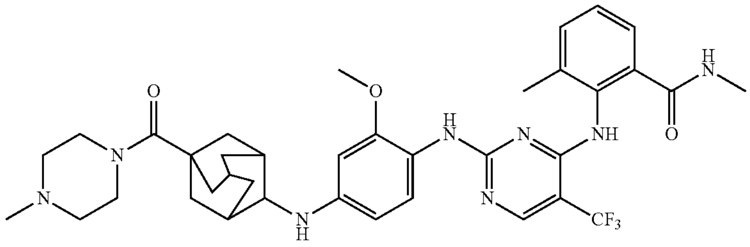 |
| 24 | 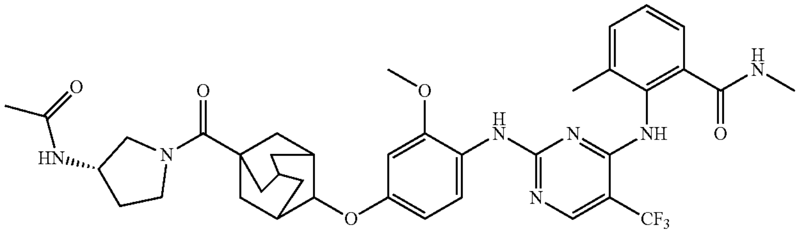 [SMILES: CNC(=O)c1cccc(C)c1Nc1nc(Nc2ccc(OC3C4CC5CC3CC(C(=O)N3CC[C@H](NC(C)=O)C3)(C5)C4)cc2OC)ncc1C(F)(F)F] |
| 25 | 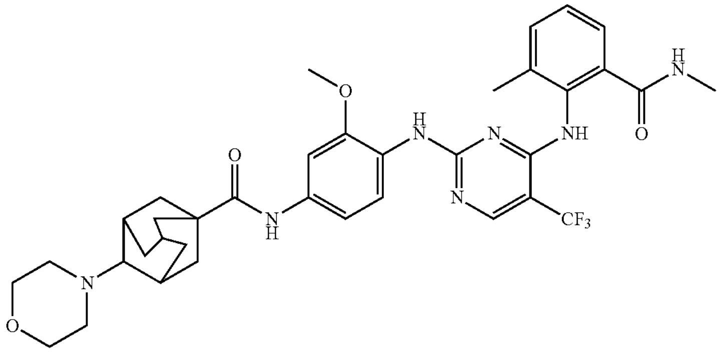 [SMILES: CNC(=O)c1cccc(C)c1Nc1nc(Nc2ccc(NC(=O)C34CC5CC(C3)C(N3CCOCC3)C(C5)C4)cc2OC)ncc1C(F)(F)F] |
| 26 | 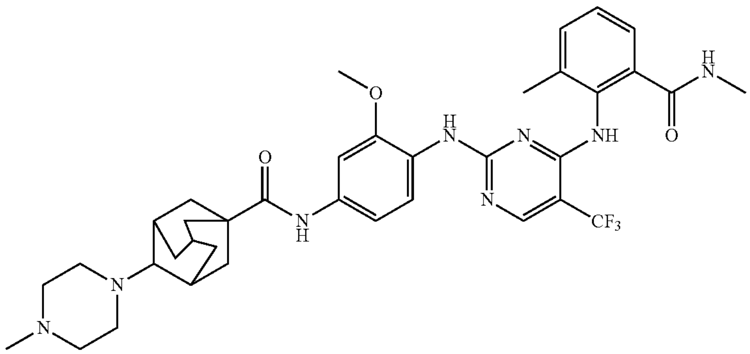 |
| 27 | 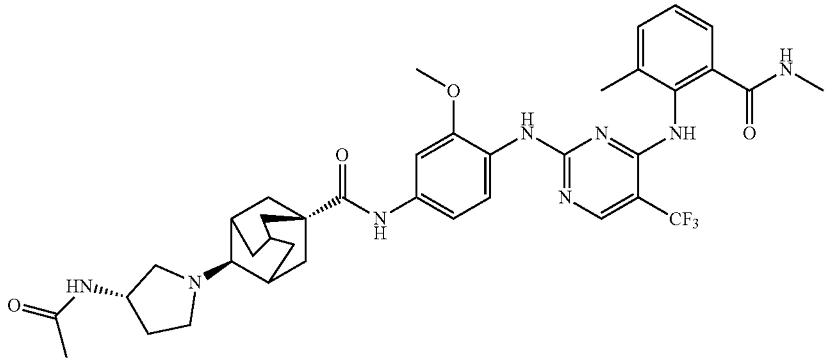 [SMILES: CNC(=O)c1cccc(C)c1Nc1nc(Nc2ccc(NC(=O)[C@]34CC5CC(C3)[C@@H](N3CC[C@H](NC(C)=O)C3)C(C5)C4)cc2OC)ncc1C(F)(F)F] |

-continued
| Example # | Structure |
|---|---|
| 28 | 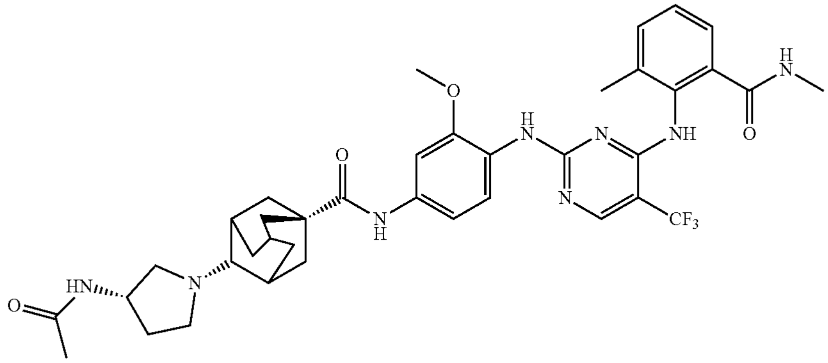 |
| 29 | 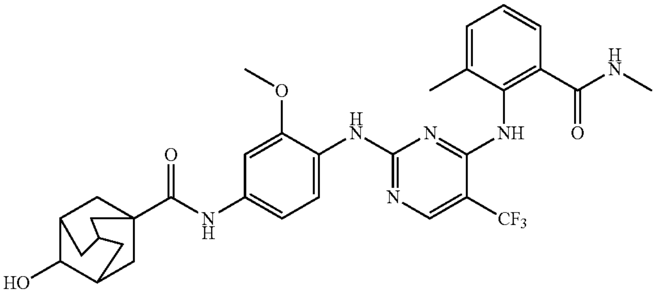 [SMILES: CNC(=O)c1cccc(C)c1Nc1nc(Nc2ccc(NC(=O)C34CC5CC(C3)C(O)C(C5)C4)cc2OC)ncc1C(F)(F)F] |
| 30 | 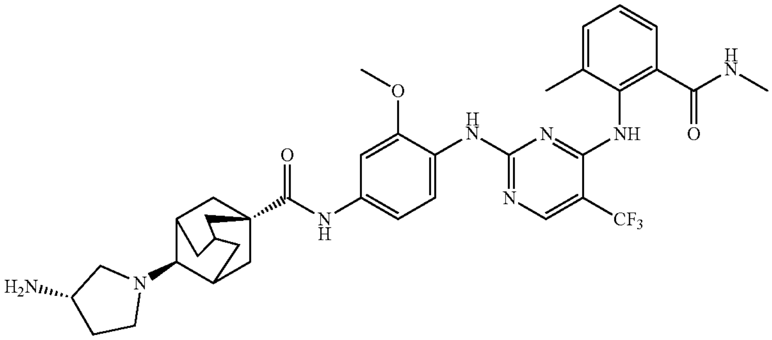 [SMILES: CNC(=O)c1cccc(C)c1Nc1nc(Nc2ccc(NC(=O)[C@]34CC5CC(C3)[C@@H](N3CC[C@H](N)C3)C(C5)C4)cc2OC)ncc1C(F)(F)F] |
| 31 | 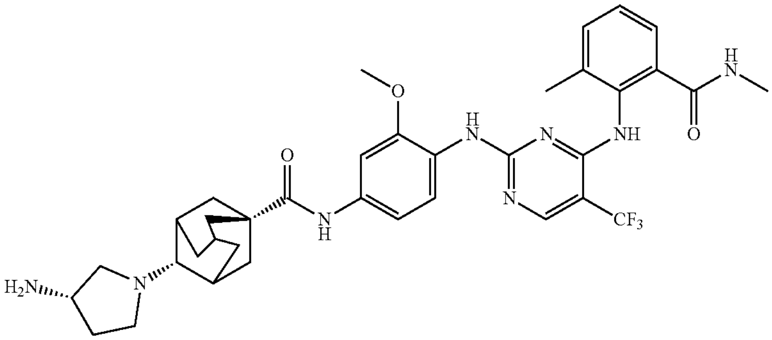 [SMILES: CNC(=O)c1cccc(C)c1Nc1nc(Nc2ccc(NC(=O)[C@]34CC5CC(C3)[C@H](N3CC[C@H](N)C3)C(C5)C4)cc2OC)ncc1C(F)(F)F] |

-continued
| Example # | Structure |
|---|---|
| 32 | 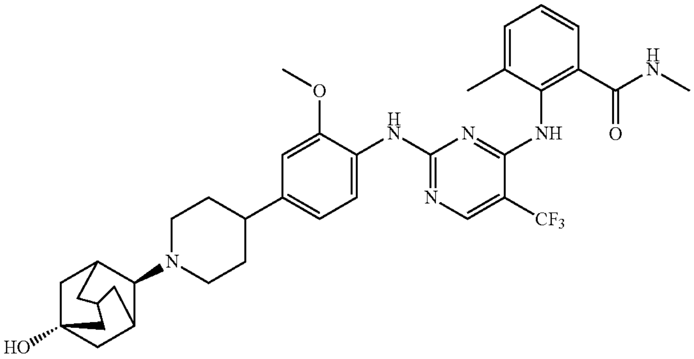 |
| 33 | 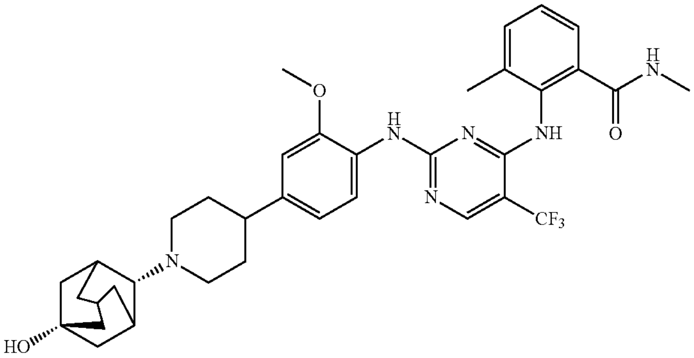 [SMILES: CNC(=O)c1cccc(C)c1Nc1nc(Nc2ccc(C3CCN([C@H]4C5CC6CC4C[C@@](O)(C6)C5)CC3)cc2OC)ncc1C(F)(F)F] |
| 34 | 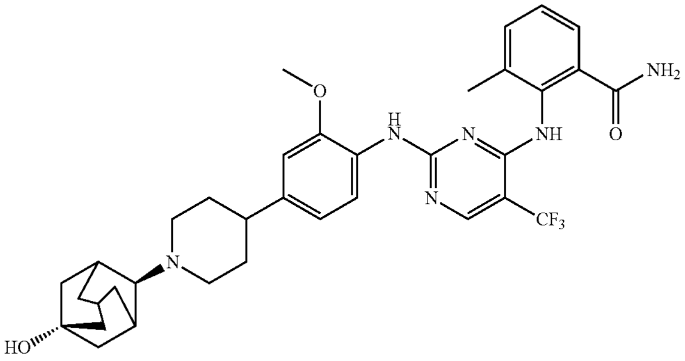 |
| 35 | 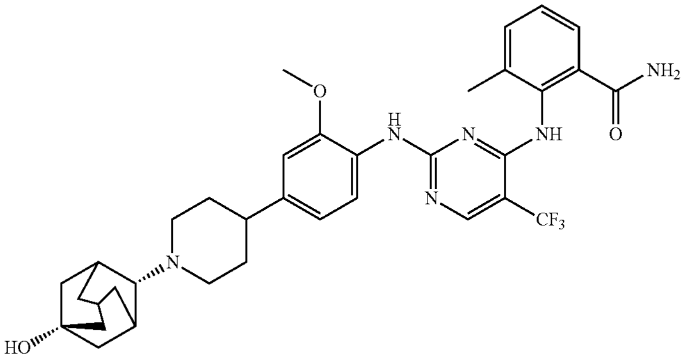 [SMILES: COc1cc(C2CCN([C@H]3C4CC5CC3C[C@@](O)(C5)C4)CC2)ccc1Nc1ncc(C(F)(F)F)c(Nc2c(C)cccc2C(N)=O)n1] |

-continued
| Example # | Structure |
| --- | --- |
| 36 | 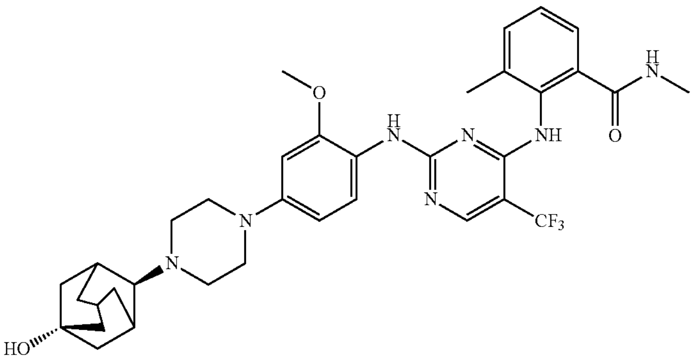 |
| 37 | 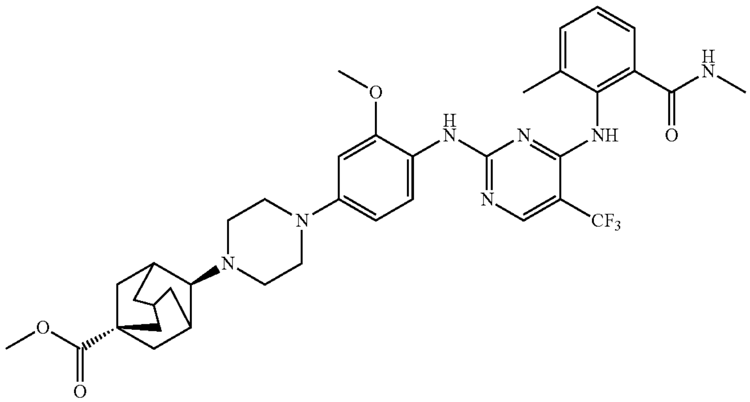 |
| 38 | 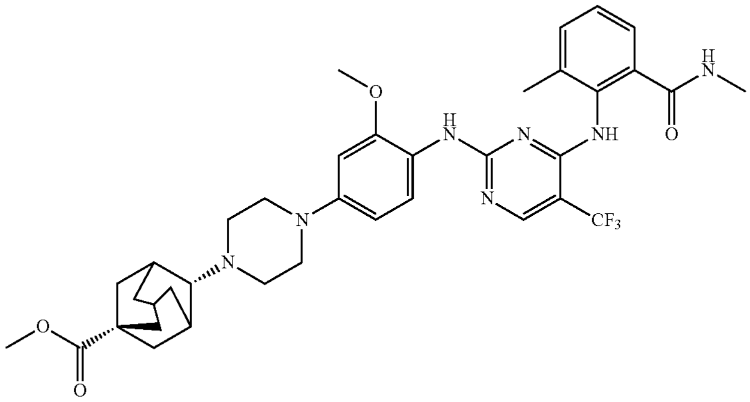 |
| 39 | 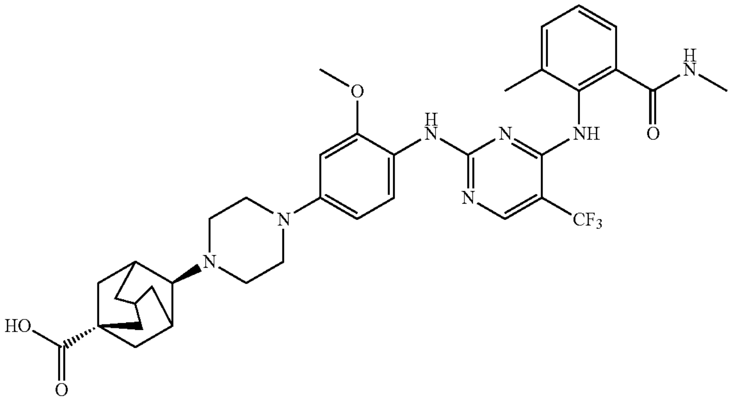 |

-continued
| Example # | Structure |
|---|---|
| 40 | 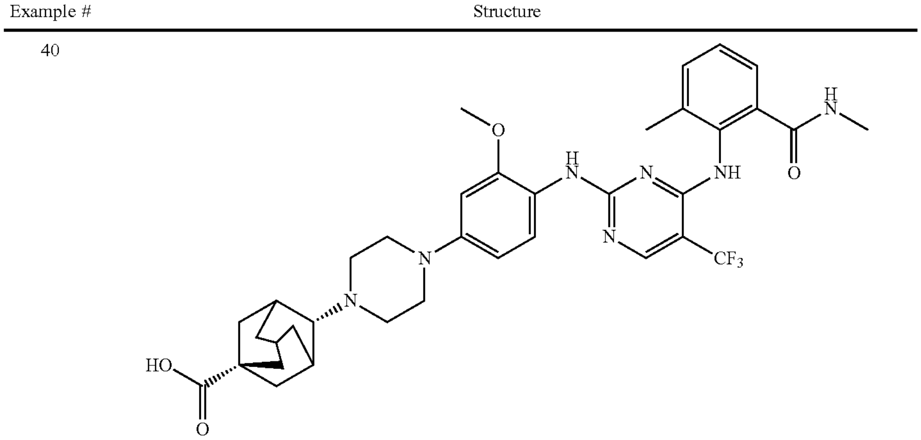 |
| 41 | 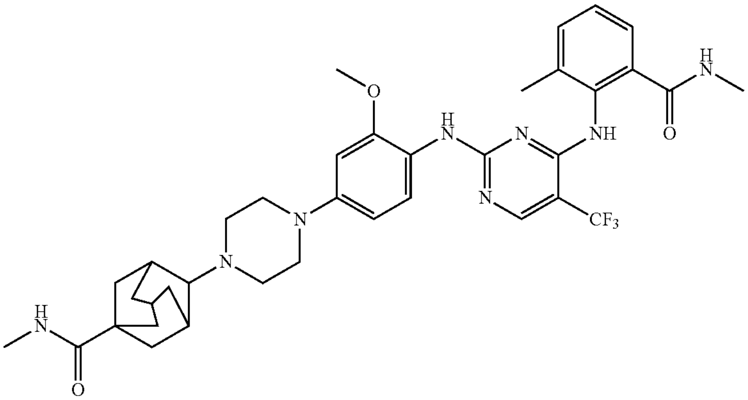 |
| 42 | 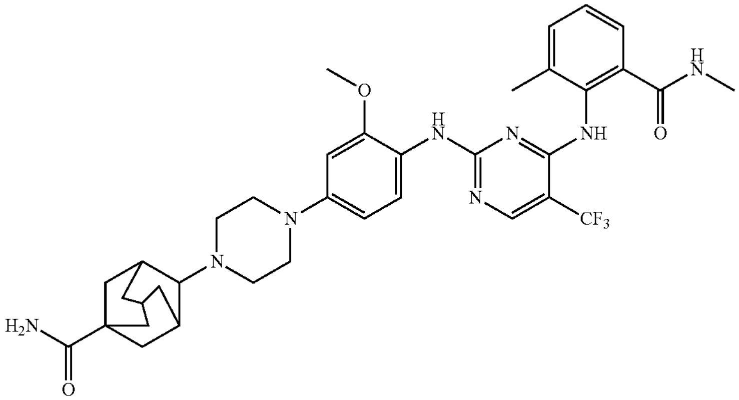 [SMILES: CNC(=O)c1cccc(C)c1Nc1nc(Nc2ccc(N3CCN(C4C5CC6CC4CC(C(N)=O)(C6)C5)CC3)cc2OC)ncc1C(F)(F)F] |
| 43 | 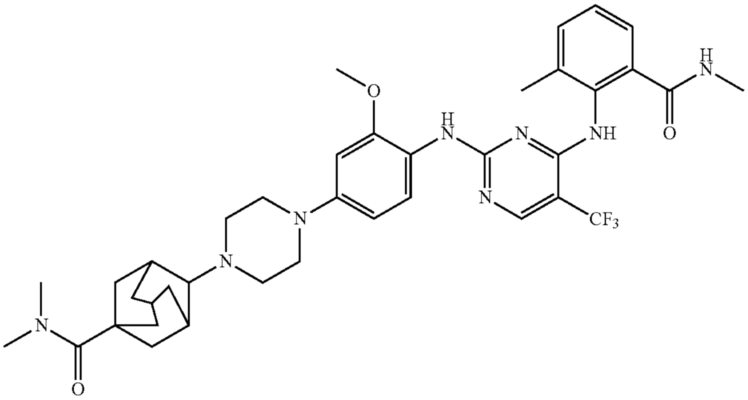 |

-continued
| Example # | Structure |
|---|---|
| 44 | 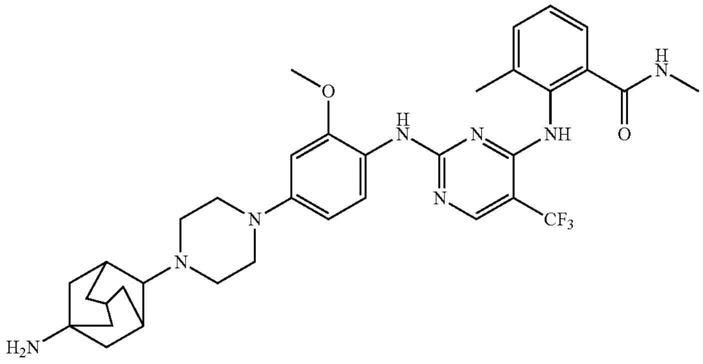 [SMILES: CNC(=O)c1cccc(C)c1Nc1nc(Nc2ccc(N3CCN(C4C5CC6CC4CC(N)(C6)C5)CC3)cc2OC)ncc1C(F)(F)F] |
| 45 | 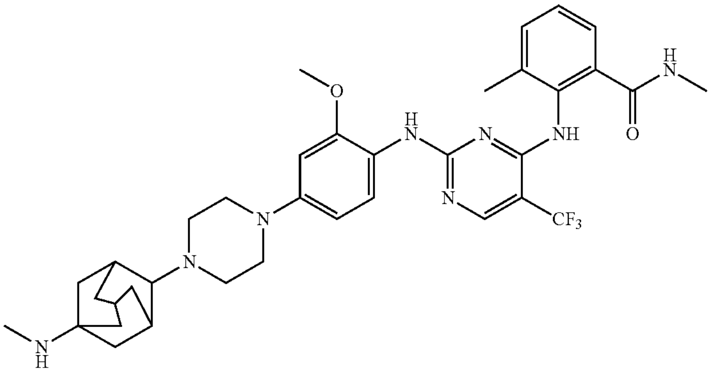 |
| 46 | 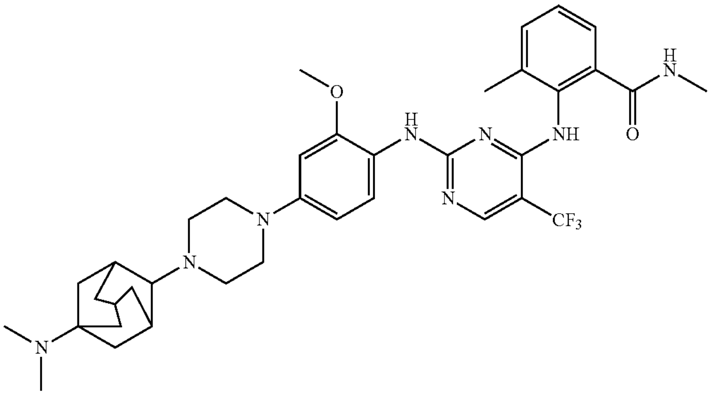 |
| 47 | 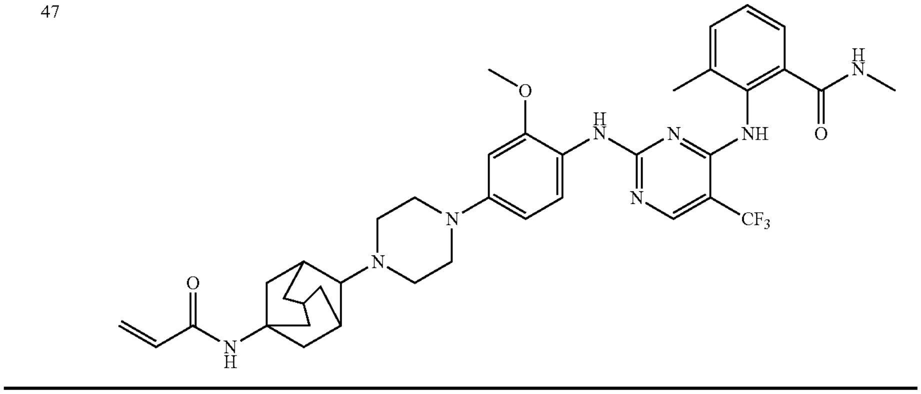 |

6. A pharmaceutical composition comprising the adamantane derivative, pharmaceutically acceptable salt thereof, stereoisomer thereof, hydrate or solvate thereof according to claim 1, as an active ingredient.

7. A method for treating an FAK activity-associated disease, comprising administering a therapeutically effective amount of the adamantane derivative, pharmaceutically acceptable salt thereof, stereoisomer thereof, hydrate or solvate thereof according to claim 1 into an individual.

8. The method of claim 7, wherein the FAK activity-associated disease is a cancer.

9. The method of claim 7, wherein the cancer is at least one selected from the group consisting of solid cancers and blood cancers.

10. The method of claim 8, wherein the cancer is at least one selected from the group consisting of gastric cancer, lung cancer, liver cancer, colorectal cancer, small intestine cancer, pancreatic cancer, brain cancer, bone cancer, melanoma, breast cancer, uterine cancer, cervical cancer, ovarian cancer, head and neck cancer, thyroid cancer, parathyroid cancer, kidney cancer, prostate cancer, urethral cancer, bladder cancer, mesothelioma, leukemia, multiple myeloma and lymphoma.

11. A method for treating an FAK activity-associated disease, comprising administering a therapeutically effective amount of the adamantane derivative, pharmaceutically acceptable salt thereof, stereoisomer thereof, hydrate or solvate thereof according to claim 5 into an individual.

12. The method of claim 11, wherein the FAK activity-associated disease is a cancer.

13. The method of claim 11, wherein the cancer is at least one selected from the group consisting of solid cancers and blood cancers.

14. The method of claim 12, wherein the cancer is at least one selected from the group consisting of gastric cancer, lung cancer, liver cancer, colorectal cancer, small intestine cancer, pancreatic cancer, brain cancer, bone cancer, melanoma, breast cancer, uterine cancer, cervical cancer, ovarian cancer, head and neck cancer, thyroid cancer, parathyroid cancer, kidney cancer, prostate cancer, urethral cancer, bladder cancer, mesothelioma, leukemia, multiple myeloma and lymphoma.

15. A method for inhibiting FAK and/or FAK2 activities, comprising administering the adamantane derivative, pharmaceutically acceptable salt thereof, stereoisomer thereof, hydrate or solvate thereof according to claim 1 into an individual.

16. A method for inhibiting FAK and/or FAK2 activities, comprising administering the adamantane derivative, pharmaceutically acceptable salt thereof, stereoisomer thereof, hydrate or solvate thereof according to claim 5 into an individual.

17. A pharmaceutical composition comprising the adamantane derivative, pharmaceutically acceptable salt thereof, stereoisomer thereof, hydrate or solvate thereof according to claim 5, as an active ingredient.

* * * * *